United States Patent [19]
Chua et al.

[11] Patent Number: 5,831,007
[45] Date of Patent: Nov. 3, 1998

[54] HUMAN RECEPTOR FOR INTERLEUKIN-12

[75] Inventors: Anne On Chua, Wayne; Ulrich Andreas Gubler, Glen Ridge, both of N.J.

[73] Assignee: Hoffmann-La Roche Inc., Nutley, N.J.

[21] Appl. No.: 419,652

[22] Filed: Apr. 11, 1995

Related U.S. Application Data

[60] Division of Ser. No. 248,532, May 31, 1994, Pat. No. 5,536,657, which is a continuation-in-part of Ser. No. 94,713, Jul. 19, 1993, abandoned.

[51] Int. Cl.$^6$ .................................................. C07K 14/715
[52] U.S. Cl. .............................. 530/350; 530/351; 514/2; 514/8
[58] Field of Search ........................... 514/2, 8; 530/350, 530/351

[56] References Cited

U.S. PATENT DOCUMENTS

| | | | |
|---|---|---|---|
| 4,578,335 | 3/1986 | Urdal et al. | 435/70.4 |
| 4,675,285 | 6/1987 | Clark et al. | 435/6 |
| 4,816,565 | 3/1989 | Honjo et al. | 530/351 |
| 5,180,812 | 1/1993 | Dower et al. | 530/351 |
| 5,198,359 | 3/1993 | Taniguchi et al. | 435/252.3 |

OTHER PUBLICATIONS

Chan, S.H., et al., *J. Exp. Med.*, 173:869 (1991).
Chizzonite, R., et al., *J. Immunol.*, 148:3117 (1992).
Cosman, David, *Cytokine*, vol. 5, No. 2, pp. 95–106 (Mar., 1993).
Desai, B., et al., *J. Immunol.*, 148:3125 (1992).
Desai, B., et al., *J. Immunol.*, 150:207A (1993).
Doherty, G.M. et al. *J. Immunol.*, 149:1666 (1992).
Fanslow, et al., *Science*, 248:739–41 (May 11, 1990).
Gately, M., et al., *Cell Immunology*, 143:127 (1992).
Gately, M.K., et al., *J. Immunol.*, 147:874 (1991).
Gearing, D.P. et al., *Cell*, 66:9 (1991).
Gubler, U., et al., *Proc. Natl. Acad. Sci (USA)*, 88:4143 (1991).
Hsieh, C. –S., et al., *Science*, 260:547 (1993).
Kobayashi, M., et al., *J. Exp. Med.*, 170:827 (1989).
Manetti, R., et al., *J. Exp. Med.*, 177:1199 (1993).
Mizuhima, S., and S. Nagata, *Nucl. Acids. Res.*, 18:5322 (1990).
Remington's Pharmaceutical Science, 16th Ed., Mack Eds., 1980.
Schoenhaut, D., et al., *J. Immunology*, 148:3433 (1992).
Stern, A.S. et al., *Proc. Natl. Acad. Sci. USA*, 87:6808 (1990).
Chizzonite, R., et al., *J. Cell Biol.*, 17:73 (1993).
Chua, A., et al., *J. Immunol.*, 153:128–136 (1994).
Wolf, et al., *J. Immunol.*, 146:3074–3081 (1991).
Cosman, D., *DNA and Protein Eng. Tech.*, 2(1):1–3 (1990).
Harada, N., et al., *Proc. Natl. Acad. Sci. USA*, 87:857–861 (1990).
Kaczmarski, R.S., et al., *Blood Reviews*, 5:193–203 (1991).
Renauld, J–C., et al., *Proc. Natl. Acad. Sci. USA*, 89:5690–5694 (1992).
Naume, et al., *Eur. J. Immunol.*, 23:1831–38 (1993).
Nicola, N., *Cuba Foundation Symposium 148*, pp. 110–126 (1990).
Robertson, et al., *J. Immunol.*, 150(5):1705–14 (Abst.) (1993).
Truitt, et al., *J. Cell. Biochem.*, Suppl. 15F, 120:120 (1991).

*Primary Examiner*—John Ulm
*Attorney, Agent, or Firm*—George W. Johnston; William H. Epstein; Briana C. Bucholz

[57] ABSTRACT

This invention relates to substantially pure Interleukin-12 receptor cDNAs and protein and uses therefore. The Interleukin-12 receptor is shown to be a member of the cytokine receptor superfamily and has a high homology to human gp130.

10 Claims, 26 Drawing Sheets

```
         10         20         30         40         50         60         70
GGTGGCTGAA CCTCCGCAGGT GGCAGAGAGG CTCCCCTGGC GCTGTGGGGC TCTACGTGA  TCCGATGGAG
         80         90        100        110        120        130        140
CCGCTGGTGA CCTGGGTGGT CCCCCTCCTC TTCCTCTTCC TGCTGTCCAG GCAGGGCGCT GCCTGCAGAA
        150        160        170        180        190        200        210
CCAGTGAGTG CTGTTTTCAG GACCCGCCAT ATCCGGATGC AGACTCAGGC TCGGGCCTCGG GCCCTAGGGA
        220        230        240        250        260        270        280
CCTGAGATGC TATCGGATAT CCAGTGATCG TTACGAGTCG TCCTGGCAGT ATGAGGGTCC CACAGCTGGG
        290        300        310        320        330        340        350
GTCAGCCACT TCCTGCGGTG TTGCCCTTAGC TCCGGGGCGCT GCTGCTACTT CGCCGCCGGC TCAGCCACCA
        360        370        380        390        400        410        420
GGCTGCAGTT CTCCGACCAG GCTGGGGTGT CTGTGCTGTA CACTGTCACA CTCTGGGTTGG AATCCTGGGC
        430        440        450        460        470        480        490
CAGGAACCAG ACAGAGAAGT CTCCTGAGGT GACCCTGCAG CTCTACAACT CAGTTAAATA TGAGCCTCCT
        500        510        520        530        540        550        560
CTGGGAGACA TCAAGGTGTC CAAGTTGGCC GGGCAGCTGC GTATGGAGTG GGAGACCCCG GATAACCAGG
        570        580        590        600        610        620        630
TTGGTGCTGA GGTGCAGTTC CGGCACCCGA CACCCAGCAG CCCATGGAAG TTGGGCGACT GCGGACCTCA
        640        650        660        670        680        690        700
GGATGATGAT ACTGAGTCCT GCCTCTGCCC CCTGGAGATG AATGTGGCCC GCGGACCTCA GCTCCGACCA
        710        720        730        740        750        760        770
CGGCAGCTGG GGAGCCAAGG AAGTTCCTGG AGCAAGTGGA GCAGCCCCGT GTGCGTTCCC CCTGAAAACC
```

| | | | | | | |
|---|---|---|---|---|---|---|
| 780 | 790 | 800 | 810 | 820 | 830 | 840 |
| CCCCACAGCC | TCAGGTGAGA | TTCTCGGTGG | AGCAGCTGGG | CCAGGATGGG | AGGAGGCCGGC | TGACCCTGAA |
| 850 | 860 | 870 | 880 | 890 | 900 | 910 |
| AGAGCAGCCA | ACCCAGCTGG | AGCTTCCAGA | AGCAAGTGGA | GGGCTGGCGC | CTGGCACGGA | GGTCACTTAC |
| 920 | 930 | 940 | 950 | 960 | 970 | 980 |
| CGACTACAGC | TCCACATGCT | GTCCTGCCCG | TGTAAGGCCA | AGGCCACCAG | GACCCTGCAC | CTGGGGAAGA |
| 990 | 1000 | 1010 | 1020 | 1030 | 1040 | 1050 |
| TGCCCTATCT | CTCGGGTGCT | GCCTACAACG | TGGCTGTCAT | CTCCTCGAAC | CAATTTGGTC | CTGGCCTGAA |
| 1060 | 1070 | 1080 | 1090 | 1100 | 1110 | 1120 |
| CCAGACGTGG | CACATTCCTG | CCGACACCCA | CACAGAACCA | GTGGCTCTGA | ATATCAGCGT | CGGAACCAAC |
| 1130 | 1140 | 1150 | 1160 | 1170 | 1180 | 1190 |
| GGGACCACCA | TGTATTGGCC | AGCCCGGGCT | CAGAGCATGA | CGTATTGCAT | TGAATGGCAG | CCTGTGGGCC |
| 1200 | 1210 | 1220 | 1230 | 1240 | 1250 | 1260 |
| AGGACGGGGG | CCTTGCCACC | TGCAGCCTGA | CTGCGCCGCA | AGACCCGGAT | CCGGCTGGAA | TGGCAACCTA |
| 1270 | 1280 | 1290 | 1300 | 1310 | 1320 | 1330 |
| CAGCTGGAGT | CGAGAGTCTG | GGGCAATGGG | GCAGGAAAAG | TGTTACTACA | TTACCATCTT | TGCCTCTGCG |
| 1340 | 1350 | 1360 | 1370 | 1380 | 1390 | 1400 |
| CACCCCGAGA | AGCTCACCTT | GTGGTCTACG | GTCCTGTCCA | CCTACCACTT | TGGGGGCAAT | GCCTCAGCAG |

```
1410        1420        1430        1440        1450        1460        1470
CTGGGACACC  GCACCACGTC  TCGGTGAAGA  ATCATAGCTT  GGACTCTGTG  TCTGTGGACT  GGCACCATC
1480        1490        1500        1510        1520        1530        1540
CCTGCTGCGC  ACCTGTCCCG  GCGTCCTAAA  GGAGTATGTT  GTCCGCTGCC  GAGATGAAGA  CAGCAAACAG
1550        1560        1570        1580        1590        1600        1610
GTGTCAGAGC  ATCCCGTGCA  GCCCACAGAG  ACCCAAGTTA  CCCTCAGTGG  CCTGCGGGCT  GGTGTAGCCT
1620        1630        1640        1650        1660        1670        1680
ACACGGTGCA  GGTGCGAGCA  GACACAGCGT  GGCTGAGGGG  TGTCTGGAGC  CAGCCCCAGC  GCTTCAGCAT
1690        1700        1710        1720        1730        1740        1750
CGAAGTGCAG  GTTTCTGATT  GGCTCATCTT  CTTCGCCTCC  CTGGGGAGCT  TCCTGAGCAT  CCTTCTCGTG
1760        1770        1780        1790        1800        1810        1820
GGCGTCCTTG  GCTACCTTGG  CCTGAACAGG  GCCGCACGGC  CTGGGGAGCT  AACCTGTGCCC  GCCGCTGCCC  ACACCCTGTG
1830        1840        1850        1860        1870        1880        1890
CCAGCTCCGC  CATTGAGTTC  CCTGGAGGGA  AGGAGACTTG  GCAGTGGATC  AACCCAGTGG  ACTTCCAGGA
1900        1910        1920        1930        1940        1950        1960
AGAGGCATCC  CTGCAGGAGG  CCCTGGTGGT  AGAGATGTCC  TGGGACAAAG  GCGAGAGGAC  TGAGCCTCTC
1970        1980        1990        2000        2010        2020        2030
GAGAAGACAG  AGCTACCTGA  GGGTGCCCCT  GAGCTGGCCC  TGGATACAGA  GTTGTCCTTG  GAGGATGGAG
2040        2050        2060        2070        2080        2090        2100
ACAGGTGCAA  GGCCAAGATG  TGATCGTTGA  GGCTCAGAGA  GGGTGAGTGA  CTCGCCCGAG  GCTACGTAGC
```

*FIG. 1C*

|     |     |     |     |     |     |     |
| --- | --- | --- | --- | --- | --- | --- |
| 10 | 20 | 30 | 40 | 50 | 60 | 70 |
| MEPLVTWVVP | LLFLFLLSRQ | GAACRTSECC | FQDPPYPDAD | SGSASGPRDL | RCYRISSDRY | ECSWQYEGPT |
| 80 | 90 | 100 | 110 | 120 | 130 | 140 |
| AGVSHFLRCC | LSSGRCCYFA | AGSATRLQFS | DQAGVSVLYT | VTLWVESWAR | NQTEKSPEVT | LQLYNSVKYE |
| 150 | 160 | 170 | 180 | 190 | 200 | 210 |
| PPLGDIKVSK | LAGQLRMEWE | TPDNQVGAEV | QFRHTPSSP | WKLGDCGPQD | DDTESCLCPL | EMNVAQEFQL |
| 220 | 230 | 240 | 250 | 260 | 270 | 280 |
| RRRQLGSQGS | SWSKWSSPVC | VPPENPPQPQ | VRFSVEQLGQ | DGRRRLTLKE | QPTQLELPEG | CQGLAPGTEV |
| 290 | 300 | 310 | 320 | 330 | 340 | 350 |
| TYRLQLHMLS | CPCKAKATRT | LHLGKMPYLS | GAAYNVAVIS | SNQFGPGLNQ | TWHIPADTHT | EPVALNISVG |
| 360 | 370 | 380 | 390 | 400 | 410 | 420 |
| TNGTTMYWPA | RAQSMTYCIE | WQPVGQDGGL | PDPAGMATYS | WSRESGAMGQ | CQGLAPGTEV |
| 430 | 440 | 450 | 460 | 470 | 480 | 490 |
| SAHPEKLTLW | STVLSTYHFG | GNASAAGTPH | HVSVKNHSLD | SVSVDWAPSL | LSTCPGVLKE | YVVRCRDEDS |
| 500 | 510 | 520 | 530 | 540 | 550 | 560 |
| KQVSEHPVQP | TETQVTLSGL | RAGVAYTVQV | RADTAWLRGV | WSQPQRFSIE | VQVSDWLIFF | ASLGSFLSIL |
| 570 | 580 | 590 | 600 | 610 | 620 | 630 |
| LVGVLGYLGL | NRAARHLCPP | LPTPCASSAI | EFPGGKETWQ | WINPVDFQEE | ASLQEALVVE | MSWDKGERTE |
| 640 | 650 | 660 |
| PLEKTELPEG | APELALDTEL | SLEDGDRCKA | KM |

FIG. 2

```
IL-12R    GSASGPRDLR  CY.RISSDRY  ECSWQYEGPT  AGV.......  ..........
GP130     LPPEKPKNLS  CIVN.EGKKM  RCEWDGGRET  HLETNFTLKS  .......EWA
G-CSF-R   YPPAIPHNLS  CLMNLTTSSL  ICQWEPGPET  HLPTSFTLKS  FKSRGNCQTQ
LIF-R     YPPDTPQQLN  CETH.DLKEI  ICSWNPGRVT  ALVGP.RATS  YTLVESFSGK
CONS      .....P..L.  C.........  .C.W.....T  ..........  ..........

SHFLRCC...  LSSGRCCYFA  AGSATRLQFS  DQAGVSVLY.  TVTLWVESWA
          THKFADCKAK  RDTPTSCTVD  YSTVYFVNI.  ..........  ..EVWVEAEN
          GDSILDCVPK  DGQSHCCIPR  KHLLLYQNM.  ..........  ..GIWVQAEN
          YVRLK.....  .........R  AEAPTNESYQ  LLFQMLPNQE  IYNFTLNAHN
          .h....C...  ......C...  ..........  ..........  ....wve...

RNQTEKSPEV  TLQLYNSVKY  EPP......L  GDIKVSKLAG  QLRMEWETPD
          ALGKVTSDHI  NFDPVYKVKP  NPPHNLSVIN  SEE....LSS  ILKLTWTNPS
          ALGTSMSPQL  CLDPMDVVKL  EPPMLRTMDP  SPEAAPPQAG  CLQLCWEPWQ
          PLGRSQSTIL  .VNITEKVYP  HTPTSFKVKD  INSTA.....  .VKLSWHLPG
          ......S...  ......Vk.   .pP.......  ........l..  .l...W..p.

NQVGAEVQF.  .RHRT.PSSP  WKLGDCGPQD  .DDTESCLCP  LEMNVAQEFQ
          IKSVIILKYN  lQYRTKDAST  W..SQIPPED  TASTRSSFTV  QDLKPFTEYV
          PGLHINQKCE  LRHKPQRGEA  SWALVGPLPL  EALQYELCGL  LPATAYTLQI
          NFAKINFLCE  IEIKKSNSVQ  EQRNVTIKGV  ENSSYLVALD  KLNP.YTLYT
          ..........  ...rt...s.  w......p.d  ...t.s....  ........e..

LR.RRQLGSQ  GSSWSKWSSP  VC.VPPENPP  QPQVRFSVEQ  LGQDGRRRLT
          FRIRCMKEDG  KGYWSDWSEE  ASGITYEDRP  SKAPSFWYKI  DPSHTQGYRT
          RCIRWPLPGH  ...WSDWSPS  LELRTTERAP  TVRLDTWWRQ  RQLDP...RT
          FRIRCSTETF  W.KWSKWSNK  KQHLTTEASP  SKGPDTW.RE  WSSDG...KN
          .r.R......  ...WS.WS..  ......E..P  .....f....  .........t

LKEQPTQLEL  PEGCQGLAPG  TEVTYRLQLH  MLSCPCKAKA  TRTLHLGKMP
          VQLVWKT..L  PPFEANGKIL  DYEVTLTRWK  SHLQNYTV..  ...NATKLTV
          VQLFWKP..V  PLEEDSGRIQ  GYVVS..WRP  SGQAGAILPL  CNTTELSCTF
          LIIYWKP..L  PINEANGKIL  SYNVSC...S  SDEETQSLSE  IPDPQHKAEI
          ..........l  P.........  ..........  ..........  ..........

YLSGAAYNVA  VISSNQFGPG  LNQTWHIPAD  T...HTEPVA  LNISVGTNGT
          NLTNDRYLAT  LTVRNLVGKS  DAAVLTIPAC  DFQATHPVMD  LKAFPKDNML
          HLPSEAQEVA  LVAYNSAGTS  RPTPVVFSES  R..GPALTRL  HAMARDPHSL
          RLDKNDYIIS  VVAKNSVGSS  PPSKIASMEI  P..NDDLKIE  QVVGMG.KGI
          .L....y...  ....N..G..  ......ipa.  ..........  l......n..

TMYW.PARAQ  SMTYCIEWQP  VGQDGGLATC  SLTAPQDPDP  AGMATYSWSR
          WVEWTTPRES  VKKYILEWCV  LSDK...APC  .ITDWQQEDG  TVHRTYLR..
          WVGWEPPNPW  PQGYVIEWGL  GPPSASNSNK  TWRMEQNGRA  TG...FLLKE
          LLTWHYDPNM  TCDYVIKWCN  SSRS...EPC  LMDWRKVPSN  STETVI....
          ...W...r..  ...Y..eW..  ........a.c  ..t..q..d.  ....ty....
```

FIG. 3A

```
ESGAMGQEKC  YYITIFASAH  PEKLTLWSTV  LSTYHFGGNA  SAAGTPHHVS
..GNLAESKC  YLITV.TPVY  ADGPG.SPES  IKAYL..KQA  PPSKGPT.VR
NIRPFQ...L  YEIIVTPLYQ  DTM....GPS  QHVYAYSQEM  APSHAP.ELH
ESDEFRPGIR  YNFFLYGCRN  QGYQLLRSMI  ..GY..IEEL  APIVAP.NFT
..g.....kc  Y.it......  ..........  ...Y.....a  .....P..v.

VKNHSLDSVS  VDWAPSLLST  CPGVLKEYV.  ..........  ..VRCRDEDS
TKKVGKNEAV  LEWDQLPVDV  QNGFIRNYTI  FYRTIIGNET  AVNV......
LKHIGKTWAQ  LEWVPEPPEL  GKSPLTHYTI  FWTNAQNQSF  SAIL......
VEDTSADSIL  VKWEDIPVEE  LRGFLRGYLF  YFGKGERDTS  KMRVLESGRS
.k........  ..W.......  ..g....Y..  ..........  ..........

KQVSEHPVQP  TETQVTLSGL  RAGVAYTVQV  RADTAWLRGV  WSQPQ..RFS
........DS  SHTEYTLSSL  TSDTLYMVRM  AAYTDEGGKD  GPEFTFTTPK
........NA  SSRGFVLHGL  EPASLYHIHL  MAASQAGATN  STVLTLMTLT
DIKVKNITDI  SQKTLRIADL  QGKTSYHLVL  RAYTDGGVGP  EKSMYVVTKE
..........  ..t..tls.L  .....Y.v..  .A.t......  ..........

IEVQVSDWLI  FFASLGSFLS  ILLVGVLGYL  GLNR...AARH  LCPPLPTPCA
FAQGEIEAIV  VPVCLAFLLT  TLLGVLF..C  FNKRDLIKKH  IWPNVPDPSK
PEGSELHIIL  GLFGLLLLLT  CLCGTAWLCC  SPNR...KNP  LWPSVPDPAH
NSVGLIIAIL  IPVAVAVIVG  VVTS...ILC  YRKREWIKET  FYPDIPNPEN
..........  ....l...l.  .ll.......  ...R.....h  ..P..P.P..

SSAIEFPGGK  ETWQWINPVD  .FQEEASLQE  ALVVEM.SWD  KGERTEPLEK
SHIAQWSPHT  PPRHNFNSKD  QMYSDGNFTD  VSVVEIEAND  KKPFPEDLKS
SSLGSWVPTI  MEEDAFQLPG  L..GTPPITK  LTVLEEDEKK  PVPW.ESHNS
CKALQFQKSV  CEGSS.ALKT  LEMNPCTPNN  VEVLETRSAF  PK.I.EDTEI
s.........  ......n..d  ..........  ..VvE....d  k....E.l..

TELPEGAPEL  ALDTELSLED  GDRCKAKM..  .
LDLFK.KEKI  NTEGHSSGIG  GSSCMSSSRP  S
SETCGLPTLV  QTYVLQGDPR  AVSTQPQSQS
ISPVAERPED  RSDAEPENHV  VVSYC
..l.......  ......s...  g..c......  .
```

FIG. 3B

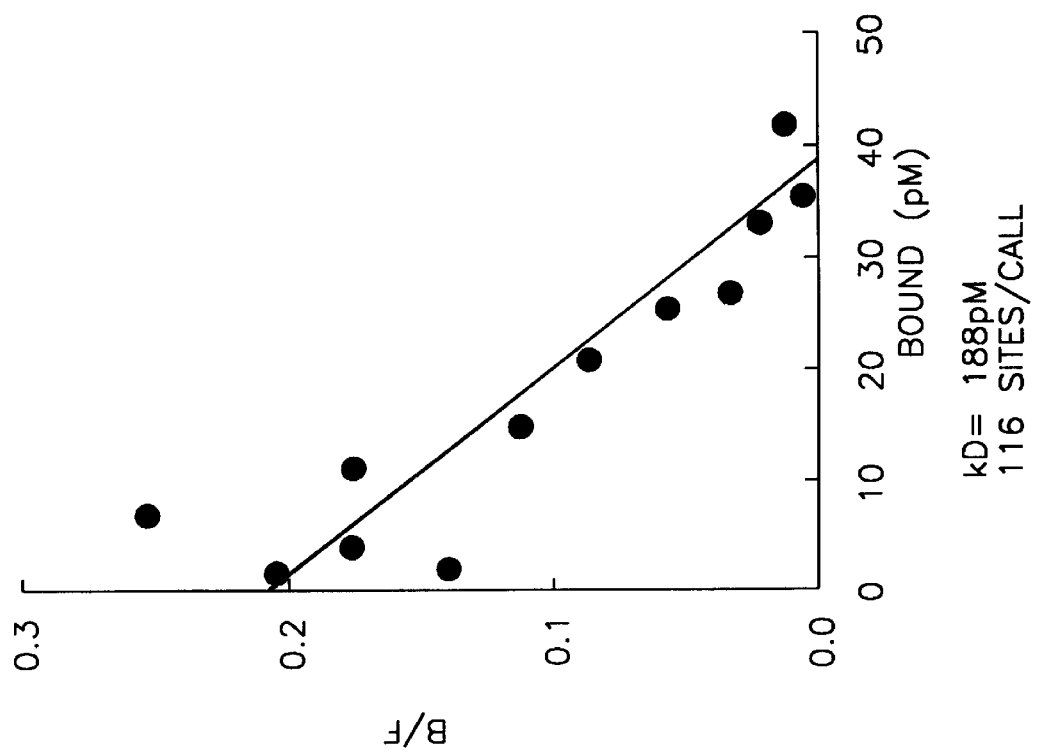
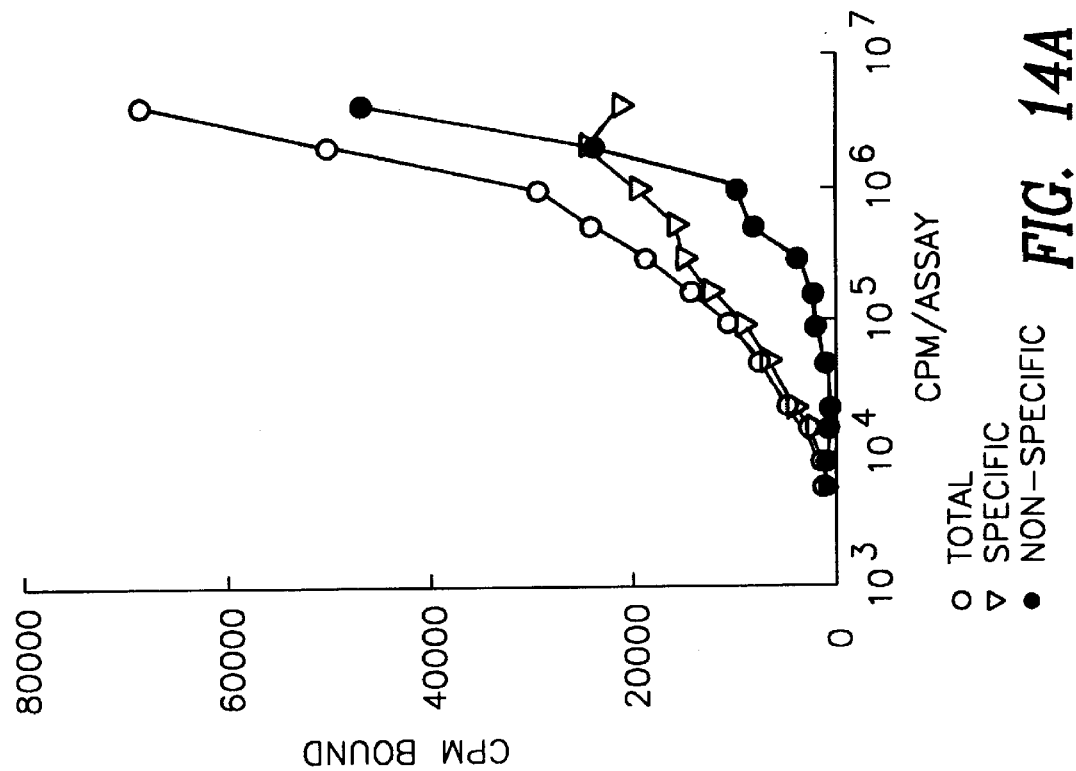
FIG. 14B
FIG. 14A

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 2104 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( v i ) ORIGINAL SOURCE:
        ( A ) ORGANISM: Homo sapiens
        ( G ) CELL TYPE: human T-cells ( v i i ) IMMEDIATE SOURCE:
        ( A ) LIBRARY: library 3 day PHA/pEF- BOS
        ( B ) CLONE: human interleukin-12 receptor clone #5

( i x ) FEATURE:

(A) NAME/KEY: CDS
(B) LOCATION: 65..2050

(xi) SEQUENCE DESCRIPTION: SEQ ID NO:1:

```
GGTGGCTGAA CCTCGCAGGT GGCAGAGAGG CTCCCCTGGG GCTGTGGGGC TCTACGTGGA                60

TCCG ATG GAG CCG CTG GTG ACC TGG GTG GTC CCC CTC CTC TTC CTC TTC                109
     Met Glu Pro Leu Val Thr Trp Val Val Pro Leu Leu Phe Leu Phe
      1               5                  10                  15

CTG CTG TCC AGG CAG GGC GCT GCC TGC AGA ACC AGT GAG TGC TGT TTT                157
Leu Leu Ser Arg Gln Gly Ala Ala Cys Arg Thr Ser Glu Cys Cys Phe
                 20                  25                  30

CAG GAC CCG CCA TAT CCG GAT GCA GAC TCA GGC TCG GCC TCG GGC CCT                205
Gln Asp Pro Pro Tyr Pro Asp Ala Asp Ser Gly Ser Ala Ser Gly Pro
             35                  40                  45

AGG GAC CTG AGA TGC TAT CGG ATA TCC AGT GAT CGT TAC GAG TGC TCC                253
Arg Asp Leu Arg Cys Tyr Arg Ile Ser Ser Asp Arg Tyr Glu Cys Ser
         50                  55                  60

TGG CAG TAT GAG GGT CCC ACA GCT GGG GTC AGC CAC TTC CTG CGG TGT                301
Trp Gln Tyr Glu Gly Pro Thr Ala Gly Val Ser His Phe Leu Arg Cys
     65                  70                  75

TGC CTT AGC TCC GGG CGC TGC TGC TAC TTC GCC GCC GGC TCA GCC ACC                349
Cys Leu Ser Ser Gly Arg Cys Cys Tyr Phe Ala Ala Gly Ser Ala Thr
 80                  85                  90                  95

AGG CTG CAG TTC TCC GAC CAG GCT GGG GTG TCT GTG CTG TAC ACT GTC                397
Arg Leu Gln Phe Ser Asp Gln Ala Gly Val Ser Val Leu Tyr Thr Val
                 100                 105                 110

ACA CTC TGG GTG GAA TCC TGG GCC AGG AAC CAG ACA GAG AAG TCT CCT                445
Thr Leu Trp Val Glu Ser Trp Ala Arg Asn Gln Thr Glu Lys Ser Pro
             115                 120                 125

GAG GTG ACC CTG CAG CTC TAC AAC TCA GTT AAA TAT GAG CCT CCT CTG                493
Glu Val Thr Leu Gln Leu Tyr Asn Ser Val Lys Tyr Glu Pro Pro Leu
         130                 135                 140

GGA GAC ATC AAG GTG TCC AAG TTG GCC GGG CAG CTG CGT ATG GAG TGG                541
Gly Asp Ile Lys Val Ser Lys Leu Ala Gly Gln Leu Arg Met Glu Trp
145                 150                 155

GAG ACC CCG GAT AAC CAG GTT GGT GCT GAG GTG CAG TTC CGG CAC CGG                589
Glu Thr Pro Asp Asn Gln Val Gly Ala Glu Val Gln Phe Arg His Arg
160                 165                 170                 175

ACA CCC AGC AGC CCA TGG AAG TTG GGC GAC TGC GGA CCT CAG GAT GAT                637
Thr Pro Ser Ser Pro Trp Lys Leu Gly Asp Cys Gly Pro Gln Asp Asp
                 180                 185                 190

GAT ACT GAG TCC TGC CTC TGC CCC CTG GAG ATG AAT GTG GCC CAG GAA                685
Asp Thr Glu Ser Cys Leu Cys Pro Leu Glu Met Asn Val Ala Gln Glu
             195                 200                 205

TTC CAG CTC CGA CGA CGG CAG CTG GGG AGC CAA GGA AGT TCC TGG AGC                733
Phe Gln Leu Arg Arg Arg Gln Leu Gly Ser Gln Gly Ser Ser Trp Ser
         210                 215                 220

AAG TGG AGC AGC CCC GTG TGC GTT CCC CCT GAA AAC CCC CCA CAG CCT                781
Lys Trp Ser Ser Pro Val Cys Val Pro Pro Glu Asn Pro Pro Gln Pro
     225                 230                 235

CAG GTG AGA TTC TCG GTG GAG CAG CTG GGC CAG GAT GGG AGG AGG CGG                829
Gln Val Arg Phe Ser Val Glu Gln Leu Gly Gln Asp Gly Arg Arg Arg
240                 245                 250                 255

CTG ACC CTG AAA GAG CAG CCA ACC CAG CTG GAG CTT CCA GAA GGC TGT                877
Leu Thr Leu Lys Glu Gln Pro Thr Gln Leu Glu Leu Pro Glu Gly Cys
                 260                 265                 270

CAA GGG CTG GCG CCT GGC ACG GAG GTC ACT TAC CGA CTA CAG CTC CAC                925
Gln Gly Leu Ala Pro Gly Thr Glu Val Thr Tyr Arg Leu Gln Leu His
             275                 280                 285

ATG CTG TCC TGC CCG TGT AAG GCC AAG GCC ACC AGG ACC CTG CAC CTG                973
```

```
              Met Leu Ser Cys Pro Cys Lys Ala Lys Ala Thr Arg Thr Leu His Leu
                      290                 295                 300

GGG AAG ATG CCC TAT CTC TCG GGT GCT GCC TAC AAC GTG GCT GTC ATC         1021
Gly Lys Met Pro Tyr Leu Ser Gly Ala Ala Tyr Asn Val Ala Val Ile
    305                 310                 315

TCC TCG AAC CAA TTT GGT CCT GGC CTG AAC CAG ACG TGG CAC ATT CCT         1069
Ser Ser Asn Gln Phe Gly Pro Gly Leu Asn Gln Thr Trp His Ile Pro
320                 325                 330                 335

GCC GAC ACC CAC ACA GAA CCA GTG GCT CTG AAT ATC AGC GTC GGA ACC         1117
Ala Asp Thr His Thr Glu Pro Val Ala Leu Asn Ile Ser Val Gly Thr
                340                 345                 350

AAC GGG ACC ACC ATG TAT TGG CCA GCC CGG GCT CAG AGC ATG ACG TAT         1165
Asn Gly Thr Thr Met Tyr Trp Pro Ala Arg Ala Gln Ser Met Thr Tyr
            355                 360                 365

TGC ATT GAA TGG CAG CCT GTG GGC CAG GAC GGG GGC CTT GCC ACC TGC         1213
Cys Ile Glu Trp Gln Pro Val Gly Gln Asp Gly Gly Leu Ala Thr Cys
        370                 375                 380

AGC CTG ACT GCG CCG CAA GAC CCG GAT CCG GCT GGA ATG GCA ACC TAC         1261
Ser Leu Thr Ala Pro Gln Asp Pro Asp Pro Ala Gly Met Ala Thr Tyr
    385                 390                 395

AGC TGG AGT CGA GAG TCT GGG GCA ATG GGG CAG GAA AAG TGT TAC TAC         1309
Ser Trp Ser Arg Glu Ser Gly Ala Met Gly Gln Glu Lys Cys Tyr Tyr
400                 405                 410                 415

ATT ACC ATC TTT GCC TCT GCG CAC CCC GAG AAG CTC ACC TTG TGG TCT         1357
Ile Thr Ile Phe Ala Ser Ala His Pro Glu Lys Leu Thr Leu Trp Ser
                420                 425                 430

ACG GTC CTG TCC ACC TAC CAC TTT GGG GGC AAT GCC TCA GCA GCT GGG         1405
Thr Val Leu Ser Thr Tyr His Phe Gly Gly Asn Ala Ser Ala Ala Gly
            435                 440                 445

ACA CCG CAC CAC GTC TCG GTG AAG AAT CAT AGC TTG GAC TCT GTG TCT         1453
Thr Pro His His Val Ser Val Lys Asn His Ser Leu Asp Ser Val Ser
        450                 455                 460

GTG GAC TGG GCA CCA TCC CTG CTG AGC ACC TGT CCC GGC GTC CTA AAG         1501
Val Asp Trp Ala Pro Ser Leu Leu Ser Thr Cys Pro Gly Val Leu Lys
    465                 470                 475

GAG TAT GTT GTC CGC TGC CGA GAT GAA GAC AGC AAA CAG GTG TCA GAG         1549
Glu Tyr Val Val Arg Cys Arg Asp Glu Asp Ser Lys Gln Val Ser Glu
480                 485                 490                 495

CAT CCC GTG CAG CCC ACA GAG ACC CAA GTT ACC CTC AGT GGC CTG CGG         1597
His Pro Val Gln Pro Thr Glu Thr Gln Val Thr Leu Ser Gly Leu Arg
                500                 505                 510

GCT GGT GTA GCC TAC ACG GTG CAG GTG CGA GCA GAC ACA GCG TGG CTG         1645
Ala Gly Val Ala Tyr Thr Val Gln Val Arg Ala Asp Thr Ala Trp Leu
            515                 520                 525

AGG GGT GTC TGG AGC CAG CCC CAG CGC TTC AGC ATC GAA GTG CAG GTT         1693
Arg Gly Val Trp Ser Gln Pro Gln Arg Phe Ser Ile Glu Val Gln Val
        530                 535                 540

TCT GAT TGG CTC ATC TTC TTC GCC TCC CTG GGG AGC TTC TTG AGC ATC         1741
Ser Asp Trp Leu Ile Phe Phe Ala Ser Leu Gly Ser Phe Leu Ser Ile
    545                 550                 555

CTT CTC GTG GGC GTC CTT GGC TAC CTT GGC CTG AAC AGG GCC GCA CGG         1789
Leu Leu Val Gly Val Leu Gly Tyr Leu Gly Leu Asn Arg Ala Ala Arg
560                 565                 570                 575

CAC CTG TGC CCG CCG CTG CCC ACA CCC TGT GCC AGC TCC GCC ATT GAG         1837
His Leu Cys Pro Pro Leu Pro Thr Pro Cys Ala Ser Ser Ala Ile Glu
                580                 585                 590

TTC CCT GGA GGG AAG GAG ACT TGG CAG TGG ATC AAC CCA GTG GAC TTC         1885
Phe Pro Gly Gly Lys Glu Thr Trp Gln Trp Ile Asn Pro Val Asp Phe
            595                 600                 605

CAG GAA GAG GCA TCC CTG CAG GAG GCC CTG GTG GTA GAG ATG TCC TGG         1933
```

| | | | | | | | | | | | | | | |
|---|---|---|---|---|---|---|---|---|---|---|---|---|---|---|
| Gln | Glu | Glu | Ala | Ser | Leu | Gln | Glu | Ala | Leu | Val | Val | Glu | Met | Ser | Trp |
| | | 610 | | | | | 615 | | | | | | 620 | | |

| | | | | | | | | | | | | | | | |
|---|---|---|---|---|---|---|---|---|---|---|---|---|---|---|---|
| GAC | AAA | GGC | GAG | AGG | ACT | GAG | CCT | CTC | GAG | AAG | ACA | GAG | CTA | CCT | GAG | 1981 |
| Asp | Lys | Gly | Glu | Arg | Thr | Glu | Pro | Leu | Glu | Lys | Thr | Glu | Leu | Pro | Glu |
| | 625 | | | | | 630 | | | | | 635 | | | | |

| | | | | | | | | | | | | | | | |
|---|---|---|---|---|---|---|---|---|---|---|---|---|---|---|---|
| GGT | GCC | CCT | GAG | CTG | GCC | CTG | GAT | ACA | GAG | TTG | TCC | TTG | GAG | GAT | GGA | 2029 |
| Gly | Ala | Pro | Glu | Leu | Ala | Leu | Asp | Thr | Glu | Leu | Ser | Leu | Glu | Asp | Gly |
| 640 | | | | | 645 | | | | 650 | | | | | 655 | |

| | | | | | | | | | |
|---|---|---|---|---|---|---|---|---|---|
| GAC | AGG | TGC | AAG | GCC | AAG | ATG | TGATCGTTGA | GGCTCAGAGA | GGGTGAGTGA | 2080 |
| Asp | Arg | Cys | Lys | Ala | Lys | Met | | | |
| | | | | 660 | | | | | |

CTCGCCCGAG GCTACGTAGC CTTT     2104

( 2 ) INFORMATION FOR SEQ ID NO:2:

( i ) SEQUENCE CHARACTERISTICS:
        ( A ) LENGTH: 662 amino acids
        ( B ) TYPE: amino acid
        ( D ) TOPOLOGY: linear ( i i ) MOLECULE TYPE: protein ( i x ) FEATURE:
        ( A ) NAME/KEY: Region
        ( B ) LOCATION: 1..23
        ( D ) OTHER INFORMATION: /note= "N-terminal signal peptide
            ( 1 . . 2 0   o r   2 3   o r   2 4 )"

( i x ) FEATURE:
        ( A ) NAME/KEY: Region
        ( B ) LOCATION: 541..570
        ( D ) OTHER INFORMATION: /note= "transmembrane region"

( i x ) FEATURE:
        ( A ) NAME/KEY: Region
        ( B ) LOCATION: 571..662
        ( D ) OTHER INFORMATION: /note= "cytoplasmic tail region"

( i x ) FEATURE:
        ( A ) NAME/KEY: Region
        ( B ) LOCATION: 577..584
        ( D ) OTHER INFORMATION: /note= "conserved area of cytoplasmic
            tail region"

( i x ) FEATURE:
        ( A ) NAME/KEY: Region
        ( B ) LOCATION: 618..629
        ( D ) OTHER INFORMATION: /note= "conserved area of cytoplasmic
            tail region"

( i x ) FEATURE:
        ( A ) NAME/KEY: Region
        ( B ) LOCATION: 52..64
        ( D ) OTHER INFORMATION: /note= "sequence motif of cytokine
            receptor superfamily Cys52..Cys62SW"

( i x ) FEATURE:
        ( A ) NAME/KEY: Region
        ( B ) LOCATION: 222..226
        ( D ) OTHER INFORMATION: /note= "cytokine receptor
            superfamily motif (W222SKWS)"

( i x ) FEATURE:
        ( A ) NAME/KEY: Region
        ( B ) LOCATION: 121..123
        ( D ) OTHER INFORMATION: /note= "N-linked glycosylation
            site"

( i x ) FEATURE:
        ( A ) NAME/KEY: Region
        ( B ) LOCATION: 329..331
        ( D ) OTHER INFORMATION: /note= "N-linked glycosylation
            site"

( i x ) FEATURE:

( A ) NAME/KEY: Region
( B ) LOCATION: 346..348
( D ) OTHER INFORMATION: /note= "N-linked glycosylation site"

( i x ) FEATURE:
( A ) NAME/KEY: Region
( B ) LOCATION: 352..354
( D ) OTHER INFORMATION: /note= "N-linked glycosylation site"

( i x ) FEATURE:
( A ) NAME/KEY: Region
( B ) LOCATION: 442..444
( D ) OTHER INFORMATION: /note= "N-linked glycosylation site"

( i x ) FEATURE:
( A ) NAME/KEY: Region
( B ) LOCATION: 456..458
( D ) OTHER INFORMATION: /note= "N-linked glycosylation site"

( i x ) FEATURE:
( A ) NAME/KEY: Region
( B ) LOCATION: 24..540
( D ) OTHER INFORMATION: /note= "Extracellular region"

( x i ) SEQUENCE DESCRIPTION: SEQ ID NO:2:

```
Met Glu Pro Leu Val Thr Trp Val Val Pro Leu Leu Phe Leu Phe Leu
 1               5                  10                  15

Leu Ser Arg Gln Gly Ala Ala Cys Arg Thr Ser Glu Cys Cys Phe Gln
                20                  25                  30

Asp Pro Pro Tyr Pro Asp Ala Asp Ser Gly Ser Ala Ser Gly Pro Arg
            35                  40                  45

Asp Leu Arg Cys Tyr Arg Ile Ser Ser Asp Arg Tyr Glu Cys Ser Trp
        50                  55                  60

Gln Tyr Glu Gly Pro Thr Ala Gly Val Ser His Phe Leu Arg Cys Cys
65                  70                  75                  80

Leu Ser Ser Gly Arg Cys Cys Tyr Phe Ala Ala Gly Ser Ala Thr Arg
                85                  90                  95

Leu Gln Phe Ser Asp Gln Ala Gly Val Ser Val Leu Tyr Thr Val Thr
                100                 105                 110

Leu Trp Val Glu Ser Trp Ala Arg Asn Gln Thr Glu Lys Ser Pro Glu
            115                 120                 125

Val Thr Leu Gln Leu Tyr Asn Ser Val Lys Tyr Glu Pro Pro Leu Gly
        130                 135                 140

Asp Ile Lys Val Ser Lys Leu Ala Gly Gln Leu Arg Met Glu Trp Glu
145                 150                 155                 160

Thr Pro Asp Asn Gln Val Gly Ala Glu Val Gln Phe Arg His Arg Thr
                165                 170                 175

Pro Ser Ser Pro Trp Lys Leu Gly Asp Cys Gly Pro Gln Asp Asp Asp
                180                 185                 190

Thr Glu Ser Cys Leu Cys Pro Leu Glu Met Asn Val Ala Gln Glu Phe
            195                 200                 205

Gln Leu Arg Arg Arg Gln Leu Gly Ser Gln Gly Ser Ser Trp Ser Lys
        210                 215                 220

Trp Ser Ser Pro Val Cys Val Pro Pro Glu Asn Pro Pro Gln Pro Gln
225                 230                 235                 240

Val Arg Phe Ser Val Glu Gln Leu Gly Gln Asp Gly Arg Arg Arg Leu
                245                 250                 255

Thr Leu Lys Glu Gln Pro Thr Gln Leu Glu Leu Pro Glu Gly Cys Gln
                260                 265                 270
```

-continued

|  |  |  |  |  |  |  |  |  |  |  |  |  |  |  |
|---|---|---|---|---|---|---|---|---|---|---|---|---|---|---|
| Gly | Leu | Ala | Pro | Gly | Thr | Glu | Val | Thr | Tyr | Arg | Leu | Gln | Leu | His | Met |
|  |  | 275 |  |  |  | 280 |  |  |  |  | 285 |  |  |  |
| Leu | Ser | Cys | Pro | Cys | Lys | Ala | Lys | Ala | Thr | Arg | Thr | Leu | His | Leu | Gly |
|  |  | 290 |  |  |  | 295 |  |  |  |  | 300 |  |  |  |
| Lys | Met | Pro | Tyr | Leu | Ser | Gly | Ala | Ala | Tyr | Asn | Val | Ala | Val | Ile | Ser |
| 305 |  |  |  |  | 310 |  |  |  |  | 315 |  |  |  |  | 320 |
| Ser | Asn | Gln | Phe | Gly | Pro | Gly | Leu | Asn | Gln | Thr | Trp | His | Ile | Pro | Ala |
|  |  |  |  | 325 |  |  |  |  | 330 |  |  |  |  | 335 |
| Asp | Thr | His | Thr | Glu | Pro | Val | Ala | Leu | Asn | Ile | Ser | Val | Gly | Thr | Asn |
|  |  |  | 340 |  |  |  |  | 345 |  |  |  |  | 350 |
| Gly | Thr | Thr | Met | Tyr | Trp | Pro | Ala | Arg | Ala | Gln | Ser | Met | Thr | Tyr | Cys |
|  |  | 355 |  |  |  |  | 360 |  |  |  |  | 365 |
| Ile | Glu | Trp | Gln | Pro | Val | Gly | Gln | Asp | Gly | Gly | Leu | Ala | Thr | Cys | Ser |
|  | 370 |  |  |  |  | 375 |  |  |  |  | 380 |  |  |  |
| Leu | Thr | Ala | Pro | Gln | Asp | Pro | Asp | Pro | Ala | Gly | Met | Ala | Thr | Tyr | Ser |
| 385 |  |  |  |  | 390 |  |  |  |  | 395 |  |  |  |  | 400 |
| Trp | Ser | Arg | Glu | Ser | Gly | Ala | Met | Gly | Gln | Glu | Lys | Cys | Tyr | Tyr | Ile |
|  |  |  |  | 405 |  |  |  |  | 410 |  |  |  |  | 415 |
| Thr | Ile | Phe | Ala | Ser | Ala | His | Pro | Glu | Lys | Leu | Thr | Leu | Trp | Ser | Thr |
|  |  |  | 420 |  |  |  |  | 425 |  |  |  |  | 430 |
| Val | Leu | Ser | Thr | Tyr | His | Phe | Gly | Gly | Asn | Ala | Ser | Ala | Ala | Gly | Thr |
|  |  | 435 |  |  |  |  | 440 |  |  |  |  | 445 |  |  |
| Pro | His | His | Val | Ser | Val | Lys | Asn | His | Ser | Leu | Asp | Ser | Val | Ser | Val |
|  | 450 |  |  |  |  | 455 |  |  |  |  | 460 |  |  |  |
| Asp | Trp | Ala | Pro | Ser | Leu | Leu | Ser | Thr | Cys | Pro | Gly | Val | Leu | Lys | Glu |
| 465 |  |  |  |  | 470 |  |  |  |  | 475 |  |  |  |  | 480 |
| Tyr | Val | Val | Arg | Cys | Arg | Asp | Glu | Asp | Ser | Lys | Gln | Val | Ser | Glu | His |
|  |  |  |  | 485 |  |  |  |  | 490 |  |  |  |  | 495 |
| Pro | Val | Gln | Pro | Thr | Glu | Thr | Gln | Val | Thr | Leu | Ser | Gly | Leu | Arg | Ala |
|  |  |  | 500 |  |  |  |  | 505 |  |  |  |  | 510 |
| Gly | Val | Ala | Tyr | Thr | Val | Gln | Val | Arg | Ala | Asp | Thr | Ala | Trp | Leu | Arg |
|  |  | 515 |  |  |  |  | 520 |  |  |  |  | 525 |  |  |
| Gly | Val | Trp | Ser | Gln | Pro | Gln | Arg | Phe | Ser | Ile | Glu | Val | Gln | Val | Ser |
|  |  | 530 |  |  |  |  | 535 |  |  |  |  | 540 |  |  |
| Asp | Trp | Leu | Ile | Phe | Phe | Ala | Ser | Leu | Gly | Ser | Phe | Leu | Ser | Ile | Leu |
| 545 |  |  |  |  | 550 |  |  |  |  | 555 |  |  |  |  | 560 |
| Leu | Val | Gly | Val | Leu | Gly | Tyr | Leu | Gly | Leu | Asn | Arg | Ala | Ala | Arg | His |
|  |  |  |  | 565 |  |  |  |  | 570 |  |  |  |  | 575 |
| Leu | Cys | Pro | Pro | Leu | Pro | Thr | Pro | Cys | Ala | Ser | Ser | Ala | Ile | Glu | Phe |
|  |  |  | 580 |  |  |  |  | 585 |  |  |  |  | 590 |
| Pro | Gly | Gly | Lys | Glu | Thr | Trp | Gln | Trp | Ile | Asn | Pro | Val | Asp | Phe | Gln |
|  |  | 595 |  |  |  |  | 600 |  |  |  |  | 605 |
| Glu | Glu | Ala | Ser | Leu | Gln | Glu | Ala | Leu | Val | Val | Glu | Met | Ser | Trp | Asp |
|  | 610 |  |  |  |  | 615 |  |  |  |  | 620 |  |  |  |
| Lys | Gly | Glu | Arg | Thr | Glu | Pro | Leu | Glu | Lys | Thr | Glu | Leu | Pro | Glu | Gly |
| 625 |  |  |  |  | 630 |  |  |  |  | 635 |  |  |  |  | 640 |
| Ala | Pro | Glu | Leu | Ala | Leu | Asp | Thr | Glu | Leu | Ser | Leu | Glu | Asp | Gly | Asp |
|  |  |  |  | 645 |  |  |  |  | 650 |  |  |  |  | 655 |
| Arg | Cys | Lys | Ala | Lys | Met |  |  |  |  |  |  |  |  |  |  |
|  |  |  | 660 |  |  |  |  |  |  |  |  |  |  |  |

( 2 ) INFORMATION FOR SEQ ID NO:3:

( i ) SEQUENCE CHARACTERISTICS:

( A ) LENGTH: 660 amino acids
( B ) TYPE: amino acid
( D ) TOPOLOGY: linear ( i i ) MOLECULE TYPE: protein ( x i ) SEQUENCE DESCRIPTION: SEQ ID NO:3:

| Met | Glu | Pro | Leu | Val | Thr | Trp | Val | Val | Pro | Leu | Leu | Phe | Leu | Phe | Leu |
|---|---|---|---|---|---|---|---|---|---|---|---|---|---|---|---|
| 1 | | | | 5 | | | | | 10 | | | | | 15 | |
| Leu | Ser | Arg | Gln | Gly | Ala | Ala | Cys | Arg | Thr | Ser | Glu | Cys | Cys | Phe | Gln |
| | | | 20 | | | | 25 | | | | | 30 | | | |
| Asp | Pro | Pro | Tyr | Pro | Asp | Ala | Asp | Ser | Gly | Ser | Ala | Ser | Gly | Pro | Arg |
| | | 35 | | | | 40 | | | | | 45 | | | | |
| Asp | Leu | Arg | Cys | Tyr | Arg | Ile | Ser | Ser | Asp | Arg | Tyr | Glu | Cys | Ser | Trp |
| | 50 | | | | 55 | | | | | 60 | | | | | |
| Gln | Tyr | Glu | Gly | Pro | Thr | Ala | Gly | Val | Ser | His | Phe | Leu | Arg | Cys | Cys |
| 65 | | | | | 70 | | | | | 75 | | | | | 80 |
| Leu | Ser | Ser | Gly | Arg | Cys | Cys | Tyr | Phe | Ala | Ala | Gly | Ser | Ala | Thr | Arg |
| | | | | 85 | | | | | 90 | | | | | 95 | |
| Leu | Gln | Phe | Ser | Asp | Gln | Ala | Gly | Val | Ser | Val | Leu | Tyr | Thr | Val | Thr |
| | | | 100 | | | | | 105 | | | | | 110 | | |
| Leu | Trp | Val | Glu | Ser | Trp | Ala | Arg | Asn | Gln | Thr | Glu | Lys | Ser | Pro | Glu |
| | | 115 | | | | | 120 | | | | | 125 | | | |
| Val | Thr | Leu | Gln | Leu | Tyr | Asn | Ser | Val | Lys | Tyr | Glu | Pro | Pro | Leu | Gly |
| | 130 | | | | | 135 | | | | | 140 | | | | |
| Asp | Ile | Lys | Val | Ser | Lys | Leu | Ala | Gly | Gln | Leu | Arg | Met | Glu | Trp | Glu |
| 145 | | | | | 150 | | | | | 155 | | | | | 160 |
| Thr | Pro | Asp | Asn | Gln | Val | Gly | Ala | Glu | Val | Gln | Phe | Arg | His | Arg | Thr |
| | | | | 165 | | | | | 170 | | | | | 175 | |
| Pro | Ser | Ser | Pro | Trp | Lys | Leu | Gly | Asp | Cys | Gly | Pro | Gln | Asp | Asp | Asp |
| | | | 180 | | | | | 185 | | | | | 190 | | |
| Thr | Glu | Ser | Cys | Leu | Cys | Pro | Leu | Glu | Met | Asn | Val | Ala | Gln | Glu | Phe |
| | | 195 | | | | | 200 | | | | | 205 | | | |
| Gln | Leu | Arg | Arg | Arg | Gln | Leu | Gly | Ser | Gln | Gly | Ser | Ser | Trp | Ser | Lys |
| | 210 | | | | | 215 | | | | | 220 | | | | |
| Trp | Ser | Ser | Pro | Val | Cys | Val | Pro | Pro | Glu | Asn | Pro | Pro | Gln | Pro | Gln |
| 225 | | | | | 230 | | | | | 235 | | | | | 240 |
| Val | Arg | Phe | Ser | Val | Glu | Gln | Leu | Gly | Gln | Asp | Gly | Arg | Arg | Arg | Leu |
| | | | | 245 | | | | | 250 | | | | | 255 | |
| Thr | Leu | Lys | Glu | Gln | Pro | Thr | Gln | Leu | Glu | Leu | Pro | Glu | Gly | Cys | Gln |
| | | | 260 | | | | | 265 | | | | | 270 | | |
| Gly | Leu | Ala | Pro | Gly | Thr | Glu | Val | Thr | Tyr | Arg | Leu | Gln | Leu | His | Met |
| | | 275 | | | | | 280 | | | | | 285 | | | |
| Leu | Ser | Cys | Pro | Cys | Lys | Ala | Lys | Ala | Thr | Arg | Thr | Leu | His | Leu | Gly |
| | 290 | | | | 295 | | | | | 300 | | | | | |
| Lys | Met | Pro | Tyr | Leu | Ser | Gly | Ala | Ala | Tyr | Asn | Val | Ala | Val | Ile | Ser |
| 305 | | | | | 310 | | | | | 315 | | | | | 320 |
| Ser | Asn | Gln | Phe | Gly | Pro | Gly | Leu | Asn | Gln | Thr | Trp | His | Ile | Pro | Ala |
| | | | | 325 | | | | | 330 | | | | | 335 | |
| Asp | Thr | His | Thr | Glu | Pro | Val | Ala | Leu | Asn | Ile | Ser | Val | Gly | Thr | Asn |
| | | | 340 | | | | | 345 | | | | | 350 | | |
| Gly | Thr | Thr | Met | Tyr | Trp | Pro | Ala | Arg | Ala | Gln | Ser | Met | Thr | Tyr | Cys |
| | | 355 | | | | | 360 | | | | | 365 | | | |
| Ile | Glu | Trp | Gln | Pro | Val | Gly | Gln | Asp | Gly | Gly | Leu | Ala | Thr | Cys | Ser |
| | | 370 | | | | | 375 | | | | | 380 | | | |

| | | | | | | | | | | | | | | |
|---|---|---|---|---|---|---|---|---|---|---|---|---|---|---|
|Leu|Thr|Ala|Pro|Gln|Asp|Pro|Asp|Pro|Ala|Gly|Met|Ala|Thr|Tyr|Ser|
|385| | | |390| | | |395| | | | | |400|

| | | | | | | | | | | | | | | | |
|---|---|---|---|---|---|---|---|---|---|---|---|---|---|---|---|
|Trp|Ser|Arg|Glu|Ser|Gly|Ala|Met|Gly|Gln|Glu|Lys|Cys|Tyr|Tyr|Ile|
| | | | |405| | | |410| | | | |415| | |

| | | | | | | | | | | | | | | | |
|---|---|---|---|---|---|---|---|---|---|---|---|---|---|---|---|
|Thr|Ile|Phe|Ala|Ser|Ala|His|Pro|Glu|Lys|Leu|Thr|Leu|Trp|Ser|Thr|
| | | |420| | | | |425| | | | |430| | |

| | | | | | | | | | | | | | | | |
|---|---|---|---|---|---|---|---|---|---|---|---|---|---|---|---|
|Val|Leu|Ser|Thr|Tyr|His|Phe|Gly|Gly|Asn|Ala|Ser|Ala|Ala|Gly|Thr|
| | |435| | | | |440| | | |445| | | | |

| | | | | | | | | | | | | | | | |
|---|---|---|---|---|---|---|---|---|---|---|---|---|---|---|---|
|Pro|His|His|Val|Ser|Val|Lys|Asn|His|Ser|Leu|Asp|Ser|Val|Ser|Val|
| |450| | | |455| | | | |460| | | | | |

| | | | | | | | | | | | | | | | |
|---|---|---|---|---|---|---|---|---|---|---|---|---|---|---|---|
|Asp|Trp|Ala|Pro|Ser|Leu|Leu|Ser|Thr|Cys|Pro|Gly|Val|Leu|Lys|Glu|
|465| | | | |470| | | | |475| | | | |480|

| | | | | | | | | | | | | | | | |
|---|---|---|---|---|---|---|---|---|---|---|---|---|---|---|---|
|Tyr|Val|Val|Arg|Cys|Arg|Asp|Glu|Asp|Ser|Lys|Gln|Val|Ser|Glu|His|
| | | | |485| | | | |490| | | | |495| |

| | | | | | | | | | | | | | | | |
|---|---|---|---|---|---|---|---|---|---|---|---|---|---|---|---|
|Pro|Val|Gln|Pro|Thr|Glu|Thr|Gln|Val|Thr|Leu|Ser|Gly|Leu|Arg|Ala|
| | | |500| | | | |505| | | |510| | | |

| | | | | | | | | | | | | | | | |
|---|---|---|---|---|---|---|---|---|---|---|---|---|---|---|---|
|Gly|Val|Ala|Tyr|Thr|Val|Gln|Val|Arg|Ala|Asp|Thr|Ala|Trp|Leu|Arg|
| | |515| | | |520| | | | |525| | | | |

| | | | | | | | | | | | | | | | |
|---|---|---|---|---|---|---|---|---|---|---|---|---|---|---|---|
|Gly|Val|Trp|Ser|Gln|Pro|Gln|Arg|Phe|Ser|Ile|Glu|Val|Gln|Val|Ser|
| |530| | | | |535| | | | |540| | | | |

| | | | | | | | | | | | | | | | |
|---|---|---|---|---|---|---|---|---|---|---|---|---|---|---|---|
|Asp|Trp|Leu|Ile|Phe|Phe|Ala|Ser|Leu|Gly|Ser|Phe|Leu|Ser|Ile|Leu|
|545| | | | |550| | | | |555| | | | |560|

| | | | | | | | | | | | | | | | |
|---|---|---|---|---|---|---|---|---|---|---|---|---|---|---|---|
|Leu|Val|Gly|Val|Leu|Gly|Tyr|Leu|Gly|Leu|Asn|Arg|Ala|Ala|Arg|His|
| | | | |565| | | |570| | | | |575| | |

| | | | | | | | | | | | | | | | |
|---|---|---|---|---|---|---|---|---|---|---|---|---|---|---|---|
|Leu|Cys|Pro|Pro|Leu|Pro|Thr|Pro|Cys|Ala|Ser|Ser|Ala|Ile|Glu|Phe|
| | | |580| | | |585| | | | |590| | | |

| | | | | | | | | | | | | | | | |
|---|---|---|---|---|---|---|---|---|---|---|---|---|---|---|---|
|Pro|Gly|Gly|Lys|Glu|Thr|Trp|Gln|Trp|Ile|Asn|Pro|Val|Asp|Phe|Gln|
| | |595| | | |600| | | | |605| | | | |

| | | | | | | | | | | | | | | | |
|---|---|---|---|---|---|---|---|---|---|---|---|---|---|---|---|
|Glu|Glu|Ala|Ser|Leu|Gln|Glu|Ala|Leu|Val|Val|Glu|Met|Ser|Trp|Asp|
| |610| | | | |615| | | | |620| | | | |

| | | | | | | | | | | | | | | | |
|---|---|---|---|---|---|---|---|---|---|---|---|---|---|---|---|
|Lys|Gly|Glu|Arg|Thr|Glu|Pro|Leu|Glu|Lys|Thr|Glu|Leu|Pro|Glu|Gly|
|625| | | | |630| | | | |635| | | | |640|

| | | | | | | | | | | | | | | | |
|---|---|---|---|---|---|---|---|---|---|---|---|---|---|---|---|
|Ala|Pro|Glu|Leu|Ala|Leu|Asp|Thr|Glu|Leu|Ser|Leu|Glu|Asp|Gly|Asp|
| | | |645| | | | |650| | | | |655| | |

| | | |
|---|---|---|
|Arg|Cys|Asp|Arg|
| | |660|

(2) INFORMATION FOR SEQ ID NO:4:

(i) SEQUENCE CHARACTERISTICS:
        (A) LENGTH: 621 amino acids
        (B) TYPE: amino acid
        (D) TOPOLOGY: linear (ii) MOLECULE TYPE: protein (ix) FEATURE:
        (A) NAME/KEY: Region
        (B) LOCATION: 1..621
        (D) OTHER INFORMATION: /note= "Represents residues 42 to 662 of SEQ ID NO:2."

(xi) SEQUENCE DESCRIPTION: SEQ ID NO:4:

| | | | | | | | | | | | | | | | |
|---|---|---|---|---|---|---|---|---|---|---|---|---|---|---|---|
|Gly|Ser|Ala|Ser|Gly|Pro|Arg|Asp|Leu|Arg|Cys|Tyr|Arg|Ile|Ser|Ser|
|1| | | |5| | | |10| | | | |15| | |

| | | | | | | | | | | | | | | | |
|---|---|---|---|---|---|---|---|---|---|---|---|---|---|---|---|
|Asp|Arg|Tyr|Glu|Cys|Ser|Trp|Gln|Tyr|Glu|Gly|Pro|Thr|Ala|Gly|Val|
| | | |20| | | | |25| | | | |30| | |

| | | | | | | | | | | | | | | | |
|---|---|---|---|---|---|---|---|---|---|---|---|---|---|---|---|
|Ser|His|Phe|Leu|Arg|Cys|Cys|Leu|Ser|Ser|Gly|Arg|Cys|Cys|Tyr|Phe|
| | |35| | | | |40| | | | |45| | | |

-continued

```
Ala  Ala  Gly  Ser  Ala  Thr  Arg  Leu  Gln  Phe  Ser  Asp  Gln  Ala  Gly  Val
     50                      55                      60

Ser  Val  Leu  Tyr  Thr  Val  Thr  Leu  Trp  Val  Glu  Ser  Trp  Ala  Arg  Asn
65                       70                      75                       80

Gln  Thr  Glu  Lys  Ser  Pro  Glu  Val  Thr  Leu  Gln  Leu  Tyr  Asn  Ser  Val
                    85                       90                      95

Lys  Tyr  Glu  Pro  Pro  Leu  Gly  Asp  Ile  Lys  Val  Ser  Lys  Leu  Ala  Gly
               100                 105                      110

Gln  Leu  Arg  Met  Glu  Trp  Glu  Thr  Pro  Asp  Asn  Gln  Val  Gly  Ala  Glu
               115                 120                      125

Val  Gln  Phe  Arg  His  Arg  Thr  Pro  Ser  Ser  Pro  Trp  Lys  Leu  Gly  Asp
     130                 135                      140

Cys  Gly  Pro  Gln  Asp  Asp  Thr  Glu  Ser  Cys  Leu  Cys  Pro  Leu  Glu
145                      150                 155                       160

Met  Asn  Val  Ala  Gln  Glu  Phe  Gln  Leu  Arg  Arg  Arg  Gln  Leu  Gly  Ser
                    165                      170                      175

Gln  Gly  Ser  Ser  Trp  Ser  Lys  Trp  Ser  Ser  Pro  Val  Cys  Val  Pro  Pro
               180                      185                      190

Glu  Asn  Pro  Pro  Gln  Pro  Gln  Val  Arg  Phe  Ser  Val  Glu  Gln  Leu  Gly
          195                      200                      205

Gln  Asp  Gly  Arg  Arg  Arg  Leu  Thr  Leu  Lys  Glu  Gln  Pro  Thr  Gln  Leu
     210                      215                      220

Glu  Leu  Pro  Glu  Gly  Cys  Gln  Gly  Leu  Ala  Pro  Gly  Thr  Glu  Val  Thr
225                      230                      235                      240

Tyr  Arg  Leu  Gln  Leu  His  Met  Leu  Ser  Cys  Pro  Cys  Lys  Ala  Lys  Ala
                    245                      250                      255

Thr  Arg  Thr  Leu  His  Leu  Gly  Lys  Met  Pro  Tyr  Leu  Ser  Gly  Ala  Ala
                    260                      265                      270

Tyr  Asn  Val  Ala  Val  Ile  Ser  Ser  Asn  Gln  Phe  Gly  Pro  Gly  Leu  Asn
               275                      280                      285

Gln  Thr  Trp  His  Ile  Pro  Ala  Asp  Thr  His  Thr  Glu  Pro  Val  Ala  Leu
     290                      295                      300

Asn  Ile  Ser  Val  Gly  Thr  Asn  Gly  Thr  Thr  Met  Tyr  Trp  Pro  Ala  Arg
305                      310                      315                      320

Ala  Gln  Ser  Met  Thr  Tyr  Cys  Ile  Glu  Trp  Gln  Pro  Val  Gly  Gln  Asp
                    325                      330                      335

Gly  Gly  Leu  Ala  Thr  Cys  Ser  Leu  Thr  Ala  Pro  Gln  Asp  Pro  Asp  Pro
               340                      345                      350

Ala  Gly  Met  Ala  Thr  Tyr  Ser  Trp  Ser  Arg  Glu  Ser  Gly  Ala  Met  Gly
          355                      360                      365

Gln  Glu  Lys  Cys  Tyr  Tyr  Ile  Thr  Ile  Phe  Ala  Ser  Ala  His  Pro  Glu
     370                      375                      380

Lys  Leu  Thr  Leu  Trp  Ser  Thr  Val  Leu  Ser  Thr  Tyr  His  Phe  Gly  Gly
385                      390                      395                      400

Asn  Ala  Ser  Ala  Ala  Gly  Thr  Pro  His  His  Val  Ser  Val  Lys  Asn  His
                    405                      410                      415

Ser  Leu  Asp  Ser  Val  Ser  Val  Asp  Trp  Ala  Pro  Ser  Leu  Leu  Ser  Thr
               420                      425                      430

Cys  Pro  Gly  Val  Leu  Lys  Glu  Tyr  Val  Val  Arg  Cys  Arg  Asp  Glu  Asp
          435                      440                      445

Ser  Lys  Gln  Val  Ser  Glu  His  Pro  Val  Gln  Pro  Thr  Glu  Thr  Gln  Val
450                      455                      460

Thr  Leu  Ser  Gly  Leu  Arg  Ala  Gly  Val  Ala  Tyr  Thr  Val  Gln  Val  Arg
```

|     |     |     |     | 465 |     |     |     |     | 470 |     |     |     |     | 475 |     |     |     |     | 480 |
| --- | --- | --- | --- | --- | --- | --- | --- | --- | --- | --- | --- | --- | --- | --- | --- | --- | --- | --- | --- |
| Ala | Asp | Thr | Ala | Trp | Leu | Arg | Gly | Val | Trp | Ser | Gln | Pro | Gln | Arg | Phe |
|     |     |     |     | 485 |     |     |     |     | 490 |     |     |     |     | 495 |     |
| Ser | Ile | Glu | Val | Gln | Val | Ser | Asp | Trp | Leu | Ile | Phe | Phe | Ala | Ser | Leu |
|     |     |     | 500 |     |     |     |     | 505 |     |     |     |     | 510 |     |     |
| Gly | Ser | Phe | Leu | Ser | Ile | Leu | Leu | Val | Gly | Val | Leu | Gly | Tyr | Leu | Gly |
|     |     | 515 |     |     |     |     | 520 |     |     |     |     | 525 |     |     |     |
| Leu | Asn | Arg | Ala | Ala | Arg | His | Leu | Cys | Pro | Pro | Leu | Pro | Thr | Pro | Cys |
|     | 530 |     |     |     |     | 535 |     |     |     |     | 540 |     |     |     |     |
| Ala | Ser | Ser | Ala | Ile | Glu | Phe | Pro | Gly | Gly | Lys | Glu | Thr | Trp | Gln | Trp |
| 545 |     |     |     |     | 550 |     |     |     |     | 555 |     |     |     |     | 560 |
| Ile | Asn | Pro | Val | Asp | Phe | Gln | Glu | Glu | Ala | Ser | Leu | Gln | Glu | Ala | Leu |
|     |     |     |     | 565 |     |     |     |     | 570 |     |     |     |     | 575 |     |
| Val | Val | Glu | Met | Ser | Trp | Asp | Lys | Gly | Glu | Arg | Thr | Glu | Pro | Leu | Glu |
|     |     |     | 580 |     |     |     |     | 585 |     |     |     |     | 590 |     |     |
| Lys | Thr | Glu | Leu | Pro | Glu | Gly | Ala | Pro | Glu | Leu | Ala | Leu | Asp | Thr | Glu |
|     |     | 595 |     |     |     |     | 600 |     |     |     |     | 605 |     |     |     |
| Leu | Ser | Leu | Glu | Asp | Gly | Asp | Arg | Cys | Lys | Ala | Lys | Met |
|     | 610 |     |     |     | 615 |     |     |     |     | 620 |     |     |

(2) INFORMATION FOR SEQ ID NO:5:

(i) SEQUENCE CHARACTERISTICS:
    (A) LENGTH: 572 amino acids
    (B) TYPE: amino acid
    (D) TOPOLOGY: linear (ii) MOLECULE TYPE: protein (ix) FEATURE:
    (A) NAME/KEY: Region
    (B) LOCATION: 1..572
    (D) OTHER INFORMATION: /note= "Represents residues 124 to 742 of human gp130."

(xi) SEQUENCE DESCRIPTION: SEQ ID NO:5:

| Leu | Pro | Pro | Glu | Lys | Pro | Lys | Asn | Leu | Ser | Cys | Ile | Val | Asn | Glu | Gly |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Lys | Lys | Met | Arg | Cys | Glu | Trp | Asp | Gly | Gly | Arg | Glu | Thr | His | Leu | Glu |
|     |     |     | 20  |     |     |     |     | 25  |     |     |     |     | 30  |     |     |
| Thr | Asn | Phe | Thr | Leu | Lys | Ser | Glu | Trp | Ala | Thr | His | Lys | Phe | Ala | Asp |
|     |     | 35  |     |     |     |     | 40  |     |     |     |     | 45  |     |     |     |
| Cys | Lys | Ala | Lys | Arg | Asp | Thr | Pro | Thr | Ser | Cys | Thr | Val | Asp | Tyr | Ser |
|     | 50  |     |     |     |     | 55  |     |     |     |     | 60  |     |     |     |     |
| Thr | Val | Tyr | Phe | Val | Asn | Ile | Glu | Val | Trp | Val | Glu | Ala | Glu | Asn | Ala |
| 65  |     |     |     |     | 70  |     |     |     |     | 75  |     |     |     |     | 80  |
| Leu | Gly | Lys | Val | Thr | Ser | Asp | His | Ile | Asn | Phe | Gln | Tyr | Arg | Thr | Lys |
|     |     |     |     | 85  |     |     |     |     | 90  |     |     |     |     | 95  |     |
| Asp | Ala | Ser | Thr | Trp | Ser | Gln | Ile | Pro | Pro | Glu | Asp | Thr | Ala | Ser | Thr |
|     |     |     | 100 |     |     |     |     | 105 |     |     |     |     | 110 |     |     |
| Arg | Ser | Ser | Phe | Thr | Val | Gln | Asp | Leu | Lys | Pro | Phe | Thr | Glu | Tyr | Val |
|     |     |     | 115 |     |     |     |     | 120 |     |     |     |     | 125 |     |     |
| Phe | Arg | Ile | Arg | Cys | Met | Lys | Glu | Asp | Gly | Lys | Gly | Tyr | Trp | Ser | Asp |
|     | 130 |     |     |     |     | 135 |     |     |     |     | 140 |     |     |     |     |
| Trp | Ser | Glu | Glu | Ala | Ser | Gly | Ile | Thr | Tyr | Glu | Asp | Arg | Pro | Ser | Lys |
| 145 |     |     |     |     | 150 |     |     |     |     | 155 |     |     |     |     | 160 |
| Ala | Pro | Ser | Phe | Trp | Tyr | Lys | Ile | Asp | Pro | Ser | His | Thr | Gln | Gly | Tyr |
|     |     |     |     | 165 |     |     |     |     | 170 |     |     |     |     | 175 |     |

```
Arg  Thr  Val  Gln  Leu  Val  Trp  Lys  Thr  Leu  Pro  Pro  Phe  Glu  Ala  Asn
               180                 185                      190

Gly  Lys  Ile  Leu  Asp  Tyr  Glu  Val  Thr  Leu  Thr  Arg  Trp  Lys  Ser  His
               195                 200                      205

Leu  Gln  Asn  Tyr  Thr  Val  Asn  Ala  Thr  Lys  Leu  Thr  Val  Asn  Leu  Thr
          210                      215                      220

Asn  Asp  Arg  Tyr  Leu  Ala  Thr  Leu  Thr  Val  Arg  Asn  Leu  Val  Gly  Lys
225                           230                 235                      240

Ser  Asp  Ala  Ala  Val  Leu  Thr  Ile  Pro  Ala  Cys  Asp  Phe  Gln  Ala  Thr
                    245                      250                           255

His  Pro  Val  Met  Asp  Leu  Lys  Ala  Phe  Pro  Lys  Asp  Asn  Met  Leu  Trp
               260                 265                      270

Val  Glu  Trp  Thr  Thr  Pro  Arg  Glu  Ser  Val  Lys  Lys  Tyr  Ile  Leu  Glu
               275                 280                      285

Trp  Cys  Val  Leu  Ser  Asp  Lys  Ala  Pro  Cys  Ile  Thr  Asp  Trp  Gln  Gln
          290                 295                      300

Glu  Asp  Gly  Thr  Val  His  Arg  Thr  Tyr  Leu  Arg  Gly  Asn  Leu  Ala  Glu
305                           310                 315                      320

Ser  Lys  Cys  Tyr  Leu  Ile  Thr  Val  Thr  Pro  Val  Tyr  Ala  Asp  Gly  Pro
                    325                      330                           335

Gly  Ser  Pro  Glu  Ser  Ile  Lys  Ala  Tyr  Leu  Lys  Gln  Ala  Pro  Pro  Ser
               340                 345                      350

Lys  Gly  Pro  Thr  Val  Arg  Thr  Lys  Lys  Val  Gly  Lys  Asn  Glu  Ala  Val
               355                 360                      365

Leu  Glu  Trp  Asp  Gln  Leu  Pro  Val  Asp  Val  Gln  Asn  Gly  Phe  Ile  Arg
          370                      375                 380

Asn  Tyr  Thr  Ile  Phe  Tyr  Arg  Thr  Ile  Ile  Gly  Asn  Glu  Thr  Ala  Val
385                           390                 395                      400

Asn  Val  Asp  Ser  Ser  His  Thr  Glu  Tyr  Thr  Leu  Ser  Ser  Leu  Thr  Ser
                    405                      410                      415

Asp  Thr  Leu  Tyr  Met  Val  Arg  Met  Ala  Ala  Tyr  Thr  Asp  Glu  Gly  Gly
               420                 425                      430

Lys  Asp  Gly  Pro  Glu  Phe  Thr  Phe  Thr  Thr  Pro  Lys  Phe  Ala  Gln  Gly
          435                      440                      445

Glu  Ile  Glu  Ala  Ile  Val  Val  Pro  Val  Cys  Leu  Ala  Phe  Leu  Leu  Thr
450                      455                      460

Thr  Leu  Leu  Gly  Val  Leu  Phe  Cys  Phe  Asn  Lys  Arg  Asp  Leu  Ile  Lys
465                      470                 475                           480

Lys  His  Ile  Trp  Pro  Asn  Val  Pro  Asp  Pro  Ser  Lys  Ser  His  Ile  Ala
                    485                 490                           495

Gln  Trp  Ser  Pro  His  Thr  Pro  Pro  Arg  His  Asn  Phe  Asn  Ser  Lys  Asp
               500                      505                      510

Gln  Met  Tyr  Ser  Asp  Gly  Asn  Phe  Thr  Asp  Val  Ser  Val  Val  Glu  Ile
          515                      520                      525

Glu  Ala  Asn  Asp  Lys  Lys  Pro  Phe  Pro  Glu  Asp  Leu  Lys  Ser  Leu  Asp
     530                      535                      540

Leu  Phe  Lys  Lys  Glu  Lys  Ile  Asn  Thr  Glu  Gly  His  Ser  Ser  Gly  Ile
545                      550                      555                      560

Gly  Gly  Ser  Ser  Cys  Met  Ser  Ser  Ser  Arg  Pro  Ser
                    565                      570
```

( 2 ) INFORMATION FOR SEQ ID NO:6:

( i ) SEQUENCE CHARACTERISTICS:

( A ) LENGTH: 602 amino acids (B) TYPE: amino acid
(D) TOPOLOGY: linear (ii) MOLECULE TYPE: protein (ix) FEATURE:
(A) NAME/KEY: Region
(B) LOCATION: 1..602
(D) OTHER INFORMATION: /note= "Represents residues 98 to 731 of human granulocyte colony-stimulating factor- receptor."

(xi) SEQUENCE DESCRIPTION: SEQ ID NO:6:

```
Arg Tyr Pro Pro Ala Ile Pro His Asn Leu Ser Cys Leu Met Asn Leu
 1               5                  10                  15

Thr Thr Ser Ser Leu Ile Cys Gln Trp Glu Pro Gly Pro Glu Thr His
            20                  25                  30

Leu Pro Thr Ser Phe Thr Leu Lys Ser Phe Lys Ser Arg Gly Asn Cys
                35                  40                  45

Gln Thr Gln Gly Asp Ser Ile Leu Asp Cys Val Pro Lys Asp Gly Gln
        50                  55                  60

Ser His Cys Cys Ile Pro Arg Lys His Leu Leu Leu Tyr Gln Asn Met
65                  70                  75                  80

Gly Ile Trp Val Gln Ala Glu Asn Ala Leu Gly Thr Ser Met Ser Pro
                85                  90                  95

Gln Leu Cys Leu Asp Pro Met Asp Val Val Lys Leu Glu Pro Pro Met
               100                 105                 110

Leu Arg Thr Met Asp Pro Ser Pro Glu Ala Ala Pro Pro Gln Ala Gly
           115                 120                 125

Cys Leu Gln Leu Cys Trp Glu Pro Trp Gln Pro Gly Leu His Ile Asn
130                 135                 140

Gln Lys Cys Glu Leu Arg His Lys Pro Gln Arg Gly Glu Ala Ser Trp
145                 150                 155                 160

Ala Leu Val Gly Pro Leu Pro Leu Glu Ala Leu Gln Tyr Glu Leu Cys
                165                 170                 175

Gly Leu Leu Pro Ala Thr Ala Tyr Thr Leu Gln Ile Arg Cys Ile Arg
            180                 185                 190

Trp Pro Leu Pro Gly His Trp Ser Asp Trp Ser Pro Ser Leu Glu Leu
           195                 200                 205

Arg Thr Thr Glu Arg Ala Pro Thr Val Arg Leu Asp Thr Trp Trp Arg
210                 215                 220

Gln Arg Gln Leu Asp Pro Arg Thr Val Gln Leu Phe Trp Lys Pro Val
225                 230                 235                 240

Pro Leu Glu Glu Asp Ser Gly Arg Ile Gln Gly Tyr Val Val Ser Trp
                245                 250                 255

Arg Pro Ser Gly Gln Ala Gly Ala Ile Leu Pro Leu Cys Asn Thr Thr
            260                 265                 270

Glu Leu Ser Cys Thr Phe His Leu Pro Ser Glu Ala Gln Glu Val Ala
           275                 280                 285

Leu Val Ala Tyr Asn Ser Ala Gly Thr Ser Arg Pro Thr Pro Val Val
        290                 295                 300

Phe Ser Glu Ser Arg Gly Pro Ala Leu Thr Arg Leu His Ala Met Ala
305                 310                 315                 320

Arg Asp Pro His Ser Leu Trp Val Gly Trp Glu Pro Pro Asn Pro Trp
                325                 330                 335

Pro Gln Gly Tyr Val Ile Glu Trp Gly Leu Gly Pro Pro Ser Ala Ser
            340                 345                 350
```

```
Asn  Ser  Asn  Lys  Thr  Trp  Arg  Met  Glu  Gln  Asn  Gly  Arg  Ala  Thr  Gly
          355                      360                     365

Phe  Leu  Leu  Lys  Glu  Asn  Ile  Arg  Pro  Phe  Gln  Leu  Tyr  Glu  Ile  Ile
     370                      375                     380

Val  Thr  Pro  Leu  Tyr  Gln  Asp  Thr  Met  Gly  Pro  Ser  Gln  His  Val  Tyr
385                      390                     395                          400

Ala  Tyr  Ser  Gln  Glu  Met  Ala  Pro  Ser  His  Ala  Pro  Glu  Leu  His  Leu
                    405                     410                          415

Lys  His  Ile  Gly  Lys  Thr  Trp  Ala  Gln  Leu  Glu  Trp  Val  Pro  Glu  Pro
               420                     425                          430

Pro  Glu  Leu  Gly  Lys  Ser  Pro  Leu  Thr  His  Tyr  Thr  Ile  Phe  Trp  Thr
          435                      440                     445

Asn  Ala  Gln  Asn  Gln  Ser  Phe  Ser  Ala  Ile  Leu  Asn  Ala  Ser  Ser  Arg
     450                      455                     460

Gly  Phe  Val  Leu  His  Gly  Leu  Glu  Pro  Ala  Ser  Leu  Tyr  His  Ile  His
465                      470                     475                          480

Leu  Met  Ala  Ala  Ser  Gln  Ala  Gly  Ala  Thr  Asn  Ser  Thr  Val  Leu  Thr
                    485                     490                          495

Leu  Met  Thr  Leu  Thr  Pro  Glu  Gly  Ser  Glu  Leu  His  Ile  Ile  Leu  Gly
               500                      505                     510

Leu  Phe  Gly  Leu  Leu  Leu  Leu  Thr  Cys  Leu  Cys  Gly  Thr  Ala  Trp
          515                      520                     525

Leu  Cys  Cys  Ser  Pro  Asn  Arg  Lys  Asn  Pro  Leu  Trp  Pro  Ser  Val  Pro
     530                      535                     540

Asp  Pro  Ala  His  Ser  Ser  Leu  Gly  Ser  Trp  Val  Pro  Thr  Ile  Met  Glu
545                           550                     555                     560

Glu  Asp  Ala  Phe  Gln  Leu  Pro  Gly  Leu  Gly  Thr  Pro  Pro  Ile  Thr  Lys
                    565                      570                         575

Leu  Thr  Val  Leu  Glu  Glu  Asp  Glu  Lys  Lys  Pro  Val  Pro  Trp  Glu  Ser
               580                      585                     590

His  Asn  Ser  Ser  Glu  Thr  Cys  Gly  Leu  Pro
          595                      600
```

( 2 ) INFORMATION FOR SEQ ID NO:7:

( i ) SEQUENCE CHARACTERISTICS:
        ( A ) LENGTH: 620 amino acids
        ( B ) TYPE: amino acid
        ( D ) TOPOLOGY: linear ( i i ) MOLECULE TYPE: protein ( i x ) FEATURE:
        ( A ) NAME/KEY: Region
        ( B ) LOCATION: 1..620
        ( D ) OTHER INFORMATION: /note= "Represents residues 331 to
            950 of leukemia inhibitory factor-
            receptor..."

( x i ) SEQUENCE DESCRIPTION: SEQ ID NO:7:

```
Tyr  Pro  Pro  Asp  Thr  Pro  Gln  Gln  Leu  Asn  Cys  Glu  Thr  His  Asp  Leu
1                        5                       10                          15

Lys  Glu  Ile  Ile  Cys  Ser  Trp  Asn  Pro  Gly  Arg  Val  Thr  Ala  Leu  Val
               20                      25                      30

Gly  Pro  Arg  Ala  Thr  Ser  Tyr  Thr  Leu  Val  Glu  Ser  Phe  Ser  Gly  Lys
          35                       40                      45

Tyr  Val  Arg  Leu  Lys  Arg  Ala  Glu  Ala  Pro  Thr  Asn  Glu  Ser  Tyr  Gln
     50                       55                      60

Leu  Leu  Phe  Gln  Met  Leu  Pro  Asn  Gln  Glu  Ile  Tyr  Asn  Phe  Thr  Leu
```

|     |     |     |     | 65  |     |     |     |     | 70  |     |     |     |     | 75  |     |     |     |     | 80  |
|-----|-----|-----|-----|-----|-----|-----|-----|-----|-----|-----|-----|-----|-----|-----|-----|-----|-----|-----|-----|

Asn Ala His Asn Pro Leu Gly Arg Ser Gln Ser Thr Ile Leu Val Asn
            85                  90                  95

Ile Thr Glu Lys Val Tyr Pro His Thr Pro Thr Ser Phe Lys Val Lys
            100                 105                 110

Asp Ile Asn Ser Thr Ala Val Lys Leu Ser Trp His Leu Pro Gly Asn
            115                 120                 125

Phe Ala Lys Ile Asn Phe Leu Cys Glu Ile Glu Ile Lys Lys Ser Asn
        130                 135                 140

Ser Val Gln Glu Gln Arg Asn Val Thr Ile Lys Gly Val Glu Asn Ser
145                 150                 155                 160

Ser Tyr Leu Val Ala Leu Asp Lys Leu Asn Pro Tyr Thr Leu Tyr Thr
                165                 170                 175

Phe Arg Ile Arg Cys Ser Thr Glu Thr Phe Trp Lys Trp Ser Lys Trp
            180                 185                 190

Ser Asn Lys Lys Gln His Leu Thr Thr Glu Ala Ser Pro Ser Lys Gly
        195                 200                 205

Pro Asp Thr Trp Arg Glu Trp Ser Ser Asp Gly Lys Asn Leu Ile Ile
        210                 215                 220

Tyr Trp Lys Pro Leu Pro Ile Asn Glu Ala Asn Gly Lys Ile Leu Ser
225                 230                 235                 240

Tyr Asn Val Ser Cys Ser Ser Asp Glu Glu Thr Gln Ser Leu Ser Glu
                245                 250                 255

Ile Pro Asp Pro Gln His Lys Ala Glu Ile Arg Leu Asp Lys Asn Asp
            260                 265                 270

Tyr Ile Ile Ser Val Val Ala Lys Asn Ser Val Gly Ser Ser Pro Pro
        275                 280                 285

Ser Lys Ile Ala Ser Met Glu Ile Pro Asn Asp Asp Leu Lys Ile Glu
290                 295                 300

Gln Val Val Gly Met Gly Lys Gly Ile Leu Leu Thr Trp His Tyr Asp
305                 310                 315                 320

Pro Asn Met Thr Cys Asp Tyr Val Ile Lys Trp Cys Asn Ser Ser Arg
                325                 330                 335

Ser Glu Pro Cys Leu Met Asp Trp Arg Lys Val Pro Ser Asn Ser Thr
            340                 345                 350

Glu Thr Val Ile Glu Ser Asp Glu Phe Arg Pro Gly Ile Arg Tyr Asn
            355                 360                 365

Phe Phe Leu Tyr Gly Cys Arg Asn Gln Gly Tyr Gln Leu Leu Arg Ser
        370                 375                 380

Met Ile Gly Tyr Ile Glu Glu Leu Ala Pro Ile Val Ala Pro Asn Phe
385                 390                 395                 400

Thr Val Glu Asp Thr Ser Ala Asp Ser Ile Leu Val Lys Trp Glu Asp
                405                 410                 415

Ile Pro Val Glu Glu Leu Arg Gly Phe Leu Arg Gly Tyr Leu Phe Tyr
            420                 425                 430

Phe Gly Lys Gly Glu Arg Asp Thr Ser Lys Met Arg Val Leu Glu Ser
        435                 440                 445

Gly Arg Ser Asp Ile Lys Val Lys Asn Ile Thr Asp Ile Ser Gln Lys
    450                 455                 460

Thr Leu Arg Ile Ala Asp Leu Gln Gly Lys Thr Ser Tyr His Leu Val
465                 470                 475                 480

Leu Arg Ala Tyr Thr Asp Gly Gly Val Gly Pro Glu Lys Ser Met Tyr
                485                 490                 495

| | | | | | | | | | | | | | | |
|---|---|---|---|---|---|---|---|---|---|---|---|---|---|---|
| Val | Val | Thr | Lys 500 | Glu | Asn | Ser | Val | Gly 505 | Leu | Ile | Ile | Ala | Ile 510 | Leu | Ile |
| Pro | Val | Ala 515 | Val | Ala | Val | Ile | Val 520 | Gly | Val | Val | Thr | Ser 525 | Ile | Leu | Cys |
| Tyr | Arg 530 | Lys | Arg | Glu | Trp | Ile 535 | Lys | Glu | Thr | Phe | Tyr 540 | Pro | Asp | Ile | Pro |
| Asn 545 | Pro | Glu | Asn | Cys | Lys 550 | Ala | Leu | Gln | Phe | Gln 555 | Lys | Ser | Val | Cys | Glu 560 |
| Gly | Ser | Ser | Ala | Leu 565 | Lys | Thr | Leu | Glu | Met 570 | Asn | Pro | Cys | Thr | Pro 575 | Asn |
| Asn | Val | Glu | Val 580 | Leu | Glu | Thr | Arg | Ser 585 | Ala | Phe | Pro | Lys | Ile 590 | Glu | Asp |
| Thr | Glu | Ile 595 | Ile | Ser | Pro | Val | Ala 600 | Glu | Arg | Pro | Glu | Asp 605 | Arg | Ser | Asp |
| Ala | Glu 610 | Pro | Glu | Asn | His | Val 615 | Val | Val | Ser | Tyr | Cys 620 | | | | |

HUMAN RECEPTOR FOR INTERLEUKIN-12

CROSS-REFERENCE TO RELATED APPLICATION

This is a division of application Ser. No. 08/248,532, filed on May 31, 1994, now U.S. Pat. No. 5,536,657 which is a continuation-in-part application of Ser. No. 08/094,713, filed Jul. 19, 1993, now abandoned.

FIELD OF THE INVENTION

This invention relates generally to cytokine receptors and more specifically relates to Interleukin-12 receptors.

BACKGROUND OF THE INVENTION

Interleukin-12 (IL-12), formerly known as cytotoxic lymphocyte maturation factor or natural killer cell stimulatory factor, is a 75-KDa heterodimeric cytokine composed of disulfide-bonded 40-KDa (p40) and 35-KDa (p35) subunits that has pleiotropic activities including stimulation of the proliferation of activated T and NK cells (Gately, M. K., et al., 1991, J. Immunol., 147:874) (Kobayashi, M., et al., 1989, J. Exp. Med., 170:827), enhancement of the lytic activity of NK/LAK cells (Kobayashi, M., et al., supra) (Stern, A. S., et al., 1990, Proc. Natl. Acad. Sci. U.S.A., 87:6808), enhancement of cytolytic T-cell responses (M. Gately et al., 1992, Cell. Immunology, 143:127), induction of interferon gamma by resting and activated T- and NK-cells (M. Kobayashi et al., supra; S. H. Chan et al., 1991, J. Exp. Med., 173:869), and promotion of $T_h1$-type helper cell responses (R. Manetti et al., 1993, J. Exp. Med., 177:1199; C.-S. Hsieh et al., 1993, Science 260:547).

The biological activity of IL-12 is mediated by the binding of the IL-12 molecules to cell surface, or plasma membrane, receptors on activated T- and NK cells; however, the contributions of the individual subunits, p35 and p40, to receptor binding and signal transduction remain unknown. Studies with labeled IL-12 have shown that this binding occurs in a specific and saturable manner. IL-12 delivers a signal to target cells through a receptor that was initially characterized on PHA-activated CD4+ and CD8+ T-cells and on IL-2 activated CD56+NK-cells (R. Chizzonite et al., 1992, J. Immunol., 148:3117; B. Desai, et al., 1992, J. Immunol., 148:3125). A survey of over 20 human cell lines belonging to the T-, B-, NK- and myelomonocytic lineages only identified a single CD4+, IL-2 dependent human T-cell line (Kit 225) that constitutively expresses the IL-12 receptor and responds to IL-12 (B. Desai, et al., 1992, J. Immunol., 148:3125; B. Desai, et al., 1993, J. Immunol. 150:207A). Freshly prepared PHA-activated PBMC and the Kit 225 cell line thus represent two convenient cell sources to study the biochemistry of the functional IL-12 receptor; there may be others. Equilibrium binding experiments with $^{125}$I-labeled IL-12 showed that i) PHA-activated PBMC express several thousand IL-12 receptors which show 3 classes of affinities: high=5–20 pM, intermediate=50–200 pM and low =2–6 nM; ii) IL-12 receptor expression on PBMC is upregulated by mitogen or IL-2 stimulation; and iii) the IL-12 receptor upregulation correlates with the ability of the cells to proliferate in response to IL-12 (R. Chizzonite, et al., 1992, J. Immunol., 148:3117; B. Desai, et al., 1992, J. Immunol., 148:3125). It was not clear at this point whether the biologically functional IL-12 receptor consists of one or more subunits. Affinity crosslinking of labeled IL-12 to activated PBMC demonstrated the size of the cell surface IL-12 binding protein(s) under nonreducing conditions to be in the range of about 150 KDa to about 200 KDa. Additional affinity crosslinking and immunoprecipitation experiments with unlabeled IL-12 bound to $^{125}$I-surface labeled activated PBMC identified an IL-12 binding protein that under reducing conditions had a size of about 110 KDa (R. Chizzonite, et al., 1992, J. Immunol., 148:3117).

Using a non-neutralizing monoclonal antibody to the IL-12 receptor, we have now succeeded in isolating a human cDNA that encodes a low affinity (5–10 nM) IL-12 receptor. This protein belongs to the cytokine receptor superfamily and within that family shows strongest homology to gp130.

In order for a molecule such as IL-12 to exert its effect on cells, it is now accepted by those skilled in the art that the molecule must interact with molecules, located on cell membranes, referred to as receptors. Patents which exemplify disclosures of interleukin receptors include Honjo et al., U.S. Pat. No. 4,816,565; Urdal et al., U.S. Pat. No. 4,578,335; Dower et al., U.S. Pat. No. 5,180,812; and Taniguchi et al., U.S. Pat. No. 5,198,359, the disclosures of which are incorporated by reference.

Fanslow, W. C. et al., Science 248:739–41 (May 11, 1990) presented data showing that the effect of IL-1 in vivo could be regulated via the administration of a soluble form of its receptor. The results that Fanslow report demonstrate the ability of a soluble cytokine receptor (soluble IL-1R) to modulate biological activity upon exogenous administration in vivo, presumably by acting as a neutralizing agent for the endogeneously produced, corresponding ligand (IL-1), and provides evidence of the therapeutic potential of soluble cytokine receptors in a variety of clinical disorders. Systemic administration of a soluble, extracellular portion of the receptor for IL-1 (soluble IL-1R) had profound inhibitory effects on the development of in vivo alloreactivity. Survival of heterotopic heart allografts was prolonged from 12 days in controls to 17 days in mice treated with soluble IL-1R. Lymph node hyperplasia in response to localized injection of allogeneic cells was completely blocked by soluble IL-1R treatment. What types of therapeutic efficacy that administration of soluble IL-12 receptor is expected to have can also be contemplated therefor by those skilled in the art.

The availability of the purified receptor, in soluble form, presents therapeutic possibilities as well, as shown by Fanslow above. Addition of soluble IL-12 receptor interferes with the effect of the interleukin on the cells, since the molecule cannot bind to the cell membrane as freely. Hence, an aspect of the invention is the treatment of pathological conditions caused by excess activity of cells possessing IL-12 receptors by adding an amount of soluble IL-12 receptors sufficient to inhibit binding of IL-12 to the aforementioned cells. This methodology can also be modified, and the soluble receptor can also be used as a screening agent for pharmaceuticals. Briefly, a pharmaceutical which works as an IL-12 antagonist can do so by blocking the binding of IL-12 to the IL-12 receptor. Prior to determining whether a material would be effective in vivo, one may use the purified IL-12 receptor in connection with a potential pharmaceutical to determine if there is binding. If not, then the pharmaceutical may no longer be a desirable candidate. If there is in fact binding, further testing may be indicated.

SUMMARY OF THE INVENTION

The present invention is directed towards an isolated cDNA coding for a human low affinity IL-12 receptor protein or subunit thereof. When expressed in mammalian cells, the cDNA gives rise to substantially homogeneous IL-12 receptor protein that binds IL-12 in a specific and saturable manner with an apparent affinity of about 2 to about 10 nM.

BRIEF DESCRIPTION OF THE DRAWINGS

FIGS. 1A, 1B and 1C DNA sequence of human IL-12 receptor cDNA clone No. 5. (translated portion=nucleotides 65 to 2050) (SEQ ID NO:1).

FIG. 2: Amino acid sequence of human IL-12 receptor protein as deduced from cDNA sequence of FIGS. 1A, 1B and 1C. (underlined amino acid residues of N-terminal sequence=signal peptide sequence; amino acid residues nos. 541 to 571=transmembrane area marked by ------; 6 potential N-linked glycosylation sites in the extracellular portion marked by -------; conserved areas 1 and 2 of the cytoplasmic domain are marked by -------- [amino acid residues nos. 577 to 584 and 618 to 629] (SEQ ID NO:2).

FIGS. 3A and 3B Alignment of the IL-12 receptor protein subunit sequence with human gp130, human granulocyte colony-stimulating factor-receptor (G-CSF-R) and leukemia inhibitory factor-receptor (LIF-R), and resulting consensus sequence. Consensus residues indicated by lowercase letters refer to identities between IL-12 receptor and gp130 only. The following sequence ranges were used: IL-12 receptor protein (SEQ ID NO:2) residues 42–662 (SEQ. ID NO:4); gp130: residues 124–742 (SEQ. ID NO:5) (M. Hibi et al., 1990, Cell, 63: 1149); G-CSF-R: residues 98–731 (SEQ. ID NO:6) (R. Fukunaga, et al., 1990, Proc. Natl. Acad. Sci (U.S.A.), 87:8702); LIF-R: residues 331–950 (SEQ. ID NO:7) (D. P. Gearing, et al., 1991, EMBO J., 10:2839).

FIGS. 14A and 14B: Equilibrium Binding of $^{125}$I-IL-12 to Detergent Solubilized IL-12R from K6 Cells

DETAILED DESCRIPTION OF THE INVENTION

Figure 4B:
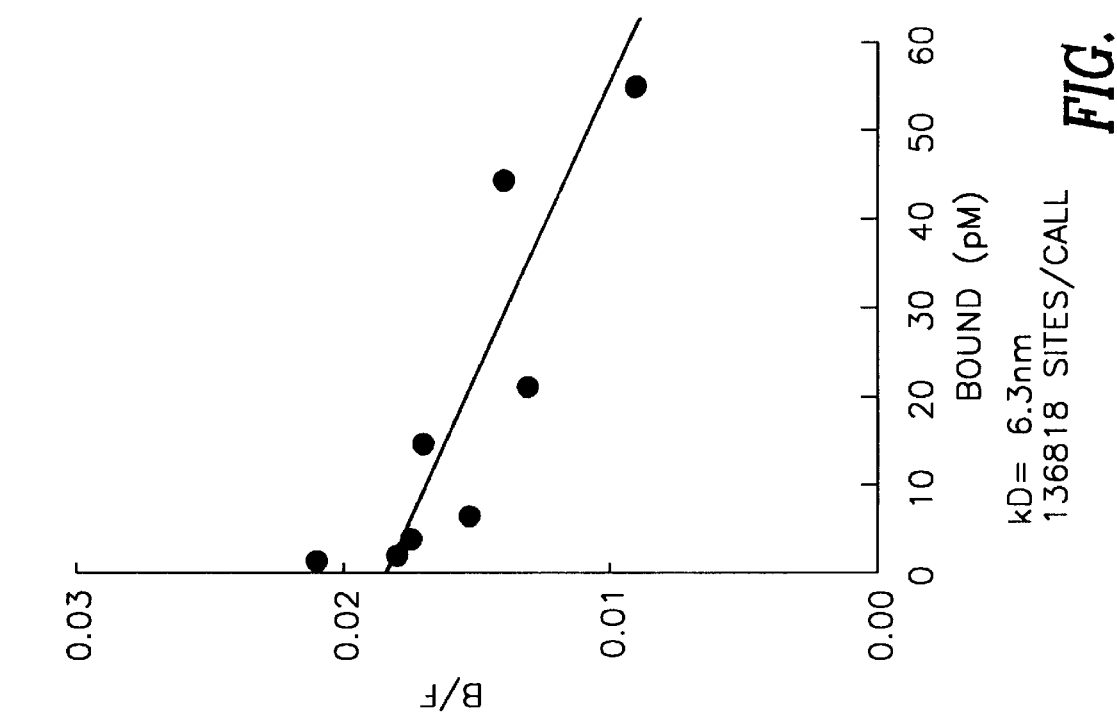
FIG. 4A and 4B: Scatchard analysis of IL-12 binding to recombinant human IL-12 receptor expressed in COS cells.

The present invention is directed towards an isolated cDNA (SEQ ID NO:1) that encodes a human low-affinity IL-12 receptor protein (SEQ ID NO:2) (clone no. 5) or subunit thereof. The amino acid sequence of the substantially homogeneous IL-12 receptor protein as deduced from the cDNA sequence is shown in FIG. 2 (SEQ ID NO:2). Clone number 17 (SEQ ID NO:3) is also of a substantially homogeneous IL-12 receptor.

The IL-12 receptor cDNA is useful for the following purposes:

Expression of recombinant IL-12 receptor protein in high levels and its use as an antigen allows production of additional neutralizing monoclonal and polyclonal antibodies. Such neutralizing antibodies can be used in in vivo model settings to elucidate the role that IL-12 and its receptor play in normal as well as pathologic immune responses (i.e. disease states that are aggravated by activated T- and NK-cells like autoimmune diseases, graft versus host disease and rheumatoid arthritis).

IL-12 receptor proteins can be administered, for example, for the purpose of suppressing immune responses in a human. A variety of diseases or conditions are caused by an immune response to alloantigen, including allograft rejection and graft-versus-host reaction. In alloantigen-induced immune responses, IL-12 receptor may suppress lymphoproliferation and inflammation which result upon activation of T cells. IL-12 receptor may therefore be used to effectively suppress alloantigen-induced immune responses in the clinical treatment of, for example, rejection of allografts (such as skin, kidney, and heart transplants), and graft-versus-host reactions in patients who have received bone marrow transplants.

IL-12 receptor may also be used in clinical treatment of autoimmune dysfunctions, such a rheumatoid arthritis, diabetes and multiple sclerosis, which are dependent upon the activation of T cells against antigens not recognized as being indigenous to the host. IL-12 receptor may also be useful in treatment of septic shock in which interferon gamma produced in response to IL-12 plays a central role in causing morbidity and mortality (G. M. Doherty et al., 1992, J. Immunol. 149:1666).

Purified IL-12 receptor compositions will be useful in diagnostic assays for IL-12 or IL-12 receptor, and also in raising antibodies to IL-12 receptor for use in diagnosis or therapy. In addition, purified IL-12 receptor compositions may be used directly in therapy to bind or scavenge IL-12, thereby providing a means for regulating the immune or inflammatory activities of IL-12. In its use to prevent or reverse pathologic immune responses, soluble IL-12 receptor can be combined with other cytokine antagonists such as antibodies to the IL-2 receptor, soluble TNF (tumor necrosis factor) receptor, the IL-1 receptor antagonist, and the like.

The dose ranges for the administration of the IL-12 receptor proteins and fragments thereof may be determined by those of ordinary skill in the art without undue experimentation. In general, appropriate dosages are those which are large enough to produce the desired effect, for example, blocking the binding of endogenous IL-12 to its natural receptor. The dosage should not be so large as to cause adverse side effects, such as unwanted cross-reactions, anaphylactic reactions, and the like. Generally, the dosage will vary with the age, condition, sex and extent of disease in the patient, counter indications, if any, immune tolerance and other such variables, to be adjusted by the individual physician. The IL-12 receptor proteins and fragments thereof can be administered parenterally by injection or by gradual perfusion over time. They can be administered intravenously, intraperitoneally, intramuscularly, or subcutaneously.

Preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present, such as, for example, anti-microbials; anti-oxidants, chelating agents, inert gases and the like. See, generally, *Remington's Pharmaceutical Science,* 16th Ed., Mack Eds., 1980.

As used herein, "DNA sequence" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the sequence and its component nucleotide sequences by standard biochemical methods, for example, using a cloning vector. Such sequences are preferably provided in the form of an open reading frame uninterrupted by internal non-translated sequences, or introns, which are typically present in eukaryotic genes. However, it will be evident that genomic DNA containing the relevant sequences could also be used. Sequences of non-translated DNA may be present 5' or 3' from the open reading frame, where the same do not interfere with manipulation or expression of the coding regions.

As used herein, "recombinant expression vector" refers to a plasmid comprising a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription and translation initiation and termination sequences. Structural elements intended for use in various eukaryotic expression systems preferably include a leader sequence enabling extracellular secretion of translated protein by a host cell. Alternatively, where recombinant protein is expressed without a leader or transport sequence, it may include an N-terminal methionine residue. This residue may optionally be subsequently cleaved from the expressed recombinant protein to provide a final product.

MATERIALS AND METHODS

Proteins and Plasmids

Recombinant human IL-12 (U. Gubler et al., 1991, Proc. Natl. Acad. Sci.(U.S.A.), 88:4143) and murine IL-12 (D. Schoenhaut et al., 1992, J. Immunology, 148:3433) were obtained as described therein.

The murine anti human IL-12 receptor monoclonal antibody 2-4E6 used herein was generated as described herein below in Examples 1 to 16 and was purified from ascites fluids by affinity chromatography on protein G-agarose according to the manufacturer's instructions (Genex). The proteins were labeled with 1-125 by a modification of the lodogen method as described (Pierce Chemical Co., Rockford, Ill.). Radiospecific activities of 5000–7000 cpm/fmole for IL-12 and 1500–2500 cpm/fmole for the 2-4E6 antibody were typically obtained.

The plasmid pEF-BOS was obtained from Dr. Nagata at the Osaka Bioscience Institute in Japan. The plasmid is based on a pUC 119 backbone and contains the elongation factor 1 alpha promoter to drive expression of genes inserted at the BstXI site (S. Mizushima and S. Nagata, Nucl. Acids: Res., 1990, 18:5322).

The murine anti human IL-12 receptor monoclonal antibody 2-4E6 was prepared, characterized, and generated as set forth in U.S. patent application Ser. No. 08/094,649, filed Jul. 19, 1993, which has been refiled as a continuation-in-part application Ser. No. 08/248,532, filed May 31, 1994, now abandoned the contents of both applications being expressly incorporated by reference herein and is as follows:

EXAMPLE 1

Preparation, Characterization & Purification of Hybridoma Antibodies

Balb/c mice (Charles River Laboratories) were immunized by the intraperitoneal route with PHA (phytohemagglutanin-activated) human PBMC (peripheral blood mononuclear cells) (PHA-activated PBMC) at $6 \times 10^7$ cells/mouse. Mice received 5 subsequent booster injections of between $2-5 \times 10^7$ cells over a six month period. For preparation of activated spleen cells, 2 mice were injected intraperitoneally and intravenously with $1 \times 10^7$ and $2.5 \times 10^6$ cells, respectively, on two successive days, starting four days prior to the cell fusion. Spleen cells were isolated from these mice and fused with SP2/0 cells at a ratio of 1:1 with 35% v/v polyethylene glycol 4000 (E. Merck) according to the method of Fazekas et al., J. Immunol. Methods 35, 1 (1980). The fused cells were plated at a density of $6 \times 10^5$ cells/ml/well in 48-well cluster dishes in IMDM supplemented with 10% FBS, glutamine (2 mM), b-mercaptoethanol (0.1 mM), gentamicin (50 g/ml), 5% ORIGEN hybridoma cloning factor (IGEN, Inc.), 5% P388D1 supernatant (Nordan, R. P., et al., J. Immunol., 139:813 (1987)) and 100 Units/ml rHuIL-6. Hybridoma supernatants were assayed for specific anti-IL-12 receptor antibodies by: 1) immunoprecipitation of the soluble complex of $^{125}$I-HuIL-12 crosslinked to IL-12 receptor ($^{125}$I-IL-12/IL-12R); 2) inhibition of $^{125}$I-HuIL-12 binding to PHA-activated PBMCs; and 3) differential binding to IL-12 receptor positive cells versus receptor negative cells. Hybridoma cell lines secreting specific anti-receptor antibodies were cloned by limiting dilution. Antibodies were purified from ascites fluids by affinity chromatography on Protein G bound to cross-linked agarose according to the manufacturer's protocol (Genex).

EXAMPLE 2

Preparation of Human PHA Lymphoblasts and IL-12 Receptor Binding Assays

Human peripheral blood mononuclear cells were isolated (see Gately et al., J. Natl. Cancer Inst. 69, 1245 (1982)) and cultured at 37° C. at a density of $5 \times 10^5$ cells/ml in tissue culture medium (TCM) containing 0.1% PHA-P (Difco). After 3 days, the cultures were split 1:1 with fresh TCM, and human rIL-2 was added to each culture to give a final concentration of 50 units/ml. The cultures were then incubated for an additional 1–2 days prior to use in assays.

PHA-activated human PBMC were washed once in binding buffer (RPMI-1640, 5% FBS, 25 mM HEPES pH 7.4) and resuspended in binding buffer to a cell density of $7 \times 10^6$ cells/ml. Lymphoblasts ($7 \times 10^5$ cells) were incubated with various concentrations of $^{125}$I-IL-12 (5–10000 pM) at room temperature for the designated times. Cell bound radioactivity was separated from free $^{125}$-IL-12 by centrifugation of the assay mixture through 0.1 ml of an oil mixture (1:2 mixture of Thomas Silicone Fluid 6428-R15 (A. H. Thomas) and Silicone Oil AR 200 {Gallard-Schlessinger}) at 4° C. for 90 sec at 10,000×g. The tip containing the cell pellet was excised, and cell bound radioactivity was determined in a gamma counter. Non-specific binding was determined by inclusion of 100 nM unlabeled IL-12 in the assay. Incubations were carried out in duplicate or triplicate. Receptor binding data were analyzed by using the non-linear regression programs EBDA and LIGAND as adapted for the IBM personal computer (McPherson, J. Pharmacol Methods 14, 213 (1985)) from Elsevier-BIOSOFT.

EXAMPLE 3

Affinity Cross-Linking of $^{125}$I-IL-12 to IL-12 Receptor Bearing Cell Lines

IL-12 receptor bearing cells were incubated with $^{125}$I-IL-12 (100–500 pM) in the presence or absence of excess unlabeled IL-12 for 2 hr at room temperature. The cells were then washed with ice-cold PBS pH 8.3 (25 mM Sodium Phosphate pH 8.3, 0.15M Nacl and 1 mM MgCl$_2$) and resuspended at a concentration of $0.5 \times 1.0^7$ cells/ml in PBS pH 8.3. BS3 (Pierce) in dimethyl sulfoxide was added to a final concentration of 0.4 mM. Incubation was continued for 30 min. at 4° C. with constant agitation. The cells were washed with ice-cold 25 mM Tris-HCl (pH 7.5), 0.15M Nacl and 5 mM EDTA and then solublized at $0.5-1.0 \times 10^8$ cells/ml in solubilization buffer (50 mM Tris-HCl (pH 8.0) containing 8 nMM,CHAPS, 0.25M NaCl, 5 mM EDTA, 40 $\mu$g/ml PMSF, 0.05% NaN$_3$, and 1% BSA) for 1 hr at 4° C. The extracts were centrifuged at 12,000×g for 45 min. at 4° C. to remove nuclei and other debris.

EXAMPLE 4

Immunoprecipitation Assay of the Soluble Complex of $^{125}$I-IL-12 Crosslinked to Human IL-12R.

For the immunoprecipitation assay, hybridoma culture supernatant (0.5 ml), diluted antisera, or purified IgG was added to a microfuge tube containing 0.1 ml of a 50% suspension of either goat-anti-mouse IgG coupled to agarose (Sigma Chem. Co.) or Protein G coupled to Sepharose 4B (Pharmacia). The assay volume was brought up to 1.0 ml with IP buffer (8 mM CHAPS in PBS (0.25M Nacl), 1% BSA, & 5 mM EDTA) and the mixture was incubated on a rotating mixer for 2 hr at room temperature. The beads were pelleted by centrifugation, resuspended in 1 ml IP buffer containing $^{125}$I-IL-12/IL-12R (10–20,000 cpm) and the mixture was incubated on a rotating mixer for 16 hr at 4° C. After this incubation, the beads were pelleted by centrifugation and washed twice in IP buffer without BSA. The $^{125}$I-labeled receptor complex bound to the solid phase antibodies was released by adding 100 $\mu$l of 2× Laemmli sample buffer (Nature 227, 680 (1970)) with and without 10% b-mercaptoethanol and heating for 5 min. at 95° C. The immunoprecipitated proteins were analyzed by SDS-PAGE on 8% or 4–15% gradient polyacrylamide gels and visualized by autoradiography.

EXAMPLE 5

Assays for IL-12R Solubilized from Cells Expressing IL-12 Receptor

To confirm that the antibodies identified by the immunoprecipitation assay were specific for IL-12R, an immunoprecipitation/soluble IL-12R binding assay was developed. As described in Example 1 above, antibodies (as hybridoma supernatant, purified IgG (50 $\mu$g) or antisera) were immobilized by binding to goat anti-mouse IgG coupled to agarose (100 $\mu$l; Sigma Chemical Co.) or protein G coupled to Sepharose 4B (100 $\mu$l; Pharmacia). For some experiments, antibodies were covalently crosslinked to protein G-Sepharose 4B, before being used in the assay. See Stern and Podlaski, Techniques in Protein Chemistry (1993). The immobilized antibodies were resuspended in IP buffer (0.3 ml) and 0.2 ml of a detergent solubilized extract of PHA-activated PBMCs or K6 cells that contained IL-12R was added. To prepare the detergent solubilized IL-12R preparation, the cells were washed with ice-cold 25 mM Tris-HCl (pH 7.5), 0.15M NaCl and 5 mM EDTA and then solublized at $1.5 \times 10^8$ cells/ml in solubilization buffer (50 mM Tris-HCl, pH 8.0, containing 8 mM CHAPS, 0.25M Nacl, 5 mM EDTA, 40 $\mu$g/ml PMSF, 0.05% NaN$_3$, and 1% BSA) for 1 hr at 4° C. The extracts were centrifuged at 120,000×g for 60 min. at 4° C. to remove nuclei and other debris. The mixture was incubated on a rotating mixer for 16 hr at 4° C. After this incubation, the beads were pelleted by centrifugation and resuspended in IP buffer (0.15 ml) containing $^{125}$I-HuIL-12 at concentrations ranging from 0.05 to 7.5 nM. The IL-12R immobilized on the antibody coated beads was incubated with $^{125}$I-HuIL-12 for 2 hrs. at room temperature on a shaker. Following this incubation, the beads were pelleted, washed twice with IP buffer and the bound radioactivity determined in a gamma counter. Non-specific binding was determined by inclusion of 70 nM unlabeled human IL-12 in the assay. Solubilized IL-12R binding data were analyzed according to the method of Scatchard using the nonlinear regression programs EBDA and LIGAND from Elsevier-BIOSOFT.

EXAMPLE 6
Competitive Inhibition of $^{125}$I-IL-12 Receptor Binding by Antibodies The ability of hybridoma supernatant solutions, purified IgG, or antisera to inhibit the binding of $^{125}$I-IL-12 to PHA-activated lymphoblasts was measured as follows: serial dilutions of culture supernatants, purified IgG or antisera were mixed with activated lymphoblasts (1–1.5×10$^6$ cells) in binding buffer (RPMI-1640, 5% FBS+25 mM HEPES pH 7.4) and incubated on an orbital shaker for 1 hour at room temperature. $^{125}$I-HuIL-12 (1×10$^5$ cpm) was added to each tube and incubated for 1–2 hours at room temperature. Non-specific binding was determined by inclusion of 10 nM unlabeled-IL-12 in the assay. Incubations were carried out in duplicate or triplicate. Cell bound radioactivity was separated from free $^{125}$I-IL-12 by centrifugation of the assay through 0.1 ml of an oil mixture as described above. The tip containing the cell pellet was excised, and cell bound radioactivity was determined in a gamma counter.

EXAMPLE 7
Labeling of Human IL-12 and mAb 2-4E6 with $^{125}$I

Human IL-12 and purified 2-4E6 IgG were labeled with $^{125}$I by a modification of the Iodogen method (Pierce Chemical Co., Rockford, Ill.). Iodogen was dissolved in chloroform and 0.05 mg dried in a 12×15 mm borosilicate glass tube. For radiolabeling, 1.0 mCi Na[$^{125}$I] (Amersham, Chicago, Ill.) was added to an Iodogen-coated tube containing 0.05 ml of Tris-iodination buffer (25 mM Tris-HCL pH 7.5, 0.4M Nacl and 1 mM EDTA) and incubated for 4 min at room temperature. The activated $^{125}$I solution was transferred to a tube containing 0.05 to 0.1 ml IL-12 (7 μg) or IgG (100 μg) in Tris-iodination buffer and the reaction was incubated for 9 min at room temperature. At the end of the incubation, 0.05 ml of Iodogen stop buffer (10 mg/ml tyrosine 10% glycerol in Dulbecco's PBS, pH 7.40) was added and reacted for 3 min. The mixture was then diluted with 1.0 ml Tris-iodination buffer, and applied to a Bio-Gel P10DG desalting column (BioRad Laboratories (BRL)) for chromatography. The column was eluted with Tris-iodination buffer, and fractions (1 ml) containing the peak amounts of labeled protein were combined and diluted to 1×10$^8$ cpm/ml with 1% BSA in Tris-iodination buffer. The TCA preciptable radioactivity (10% TCA final concentration) was typically in excess of 95% of the total radioactivity. The radiospecific activity was typically ~1500 to 2500 cmp/fmol for 2-4E6 IgG and 5000 to 7000 cpm/fmole for IL-12.

EXAMPLE 8
Binding Assays of $^{125}$I-2-4E6 to Intact Cells

PHA-activated human PBMC were washed once in binding buffer (RPMI 1640, 5% FBS and 25 mM HEPES, pH 7.4) and resuspended in binding buffer to a cell density of 1.5×10$^7$ cells/ml. Lymphoblasts (1.5×10$^6$ cells) were incubated with various concentrations of 125I-2-4E6-IgG (0.005 to 2 nM) at room temperature for 1.5 hrs. Cell bound radioactivity was separated from free $^{125}$I-2-4E6 IgG by centrifugation of the assay mixture through 0.1 ml silicone oil at 4° C. for 90 seconds at 10,000×g. The tip containing the cell pellet was excised, and cell bound radioactivity was determined in a gamma counter. Non-specific binding was determined by inclusion of 67 nM unlabeled 2-4E6 IgG in the assay. Incubations were carried out in duplicate or triplicate. Receptor binding data were analyzed by using the nonlinear regression programs EBDA, LIGAND and Kinetics as adapted for the IBM personal computer from Elsevier BIOSOFT.

EXAMPLE 9
Expression of Recombinant IL-12R in COS Cells and Determination of $^{125}$-I2-4E6 Binding COS cells (4–5×10$^7$) were transfected by electroporation with 25 μg of plasmid DNA expressing recombinant human IL-12R, as described hereinbelow, in a BioRad Gene Pulser (250 μF, 250 volts) according to the manufacturer's protocol. The cells were plated in a 600 cm$^2$ culture plate, harvested after 72 hours by scraping, washed and resuspended in binding buffer. Transfected cells (8×10$^4$) were incubated with increasing concentrations of $^{125}$I-labeled 2-4E6 or IL-12 at room temperature for 2 hrs. Cell bound radioactivity was separated from free $^{125}$I-labeled 2-4E6 or IL-12 as described above.

EXAMPLE 10
Western Blot Analysis of Soluble IL-12R with mAb 2-4E6

PHA-activated PBMC were washed 3 times with ice-cold PBS and solubilized at 0.5×10$^8$ cells/ml in solubilization buffer (50 mM Tris-HCl pH 8.0 containing 8 mM CHAPS, 0.25M NaCl, 5 mM EDTA, 40 μg/ml PMSF, 0.05% NaN$_3$ and 1 mg/ml BSA) for 1 hr at 4° C. The extracts were centrifuged at 12,000×g for 45 min. at 4° C. to remove nuclei and other debris. The extracts were incubated with 2-4E6 IgG or control IgG bound to goat-anti-mouse IgG immobilized on cross-linked agarose (Sigma Chemical Co.). The precipitated proteins were released by treatment with 0.1M glycine pH 2.3, neutralized with 3M Tris, mixed with ⅕ volume of 5× Laemmli sample buffer, and separated by SDS/PAGE on 8% pre-cast acrylamide gels (NOVEX). The separated proteins were transferred to nitrocellulose membrane (0.2 mM) for 16 hours at 100 volts in 10 mM TRIS-HCL (pH 8.3), 76.8 mM glycine, 20% methanol and 0.01% SDS. The nitrocellulose membrane was blocked with BLOTTO (5.0% w/v nonfat dry milk in PBS+0.05% Tween 20) and duplicate blots were probed with $^{125}$I-2-4E6 IgG (1×10$^6$ cpm/ml in 8 mM CHAPS in PBS, 0.25M Nacl, 10% BSA and 5 mM EDTA)+unlabeled 2-4E6 IgG (67 nM).

EXAMPLE 11
Analysis of IL-12 Receptor Expression on Human Cells by Fluorescence Activated Cell Sorting with mAb 2-4E6

To stain cells expressing IL-12 receptor, 1×10$^6$ cells in 100 μl staining buffer (PBS containing 2% FBS and 0.1% NaN$_3$) were incubated with 10 μl of 2-4E6 ascites fluid for 25 min. at 4° C. Cells were then washed twice with staining buffer followed by incubation with a 1:100 dilution of goat F(ab)2 anti mouse Ig-PE (Tago, Burlingame Calif.) for 25 min. at 4° C. The stained cells were washed twice with staining buffer and then analyzed on a FACScan flow cytometer (Becton Dickinson).

EXAMPLE 12
Inhibition of IL-12 Binding to Human PHA-Lymphoblasts by Mouse Anti-IL-12R Antiserum.

Figure 7:
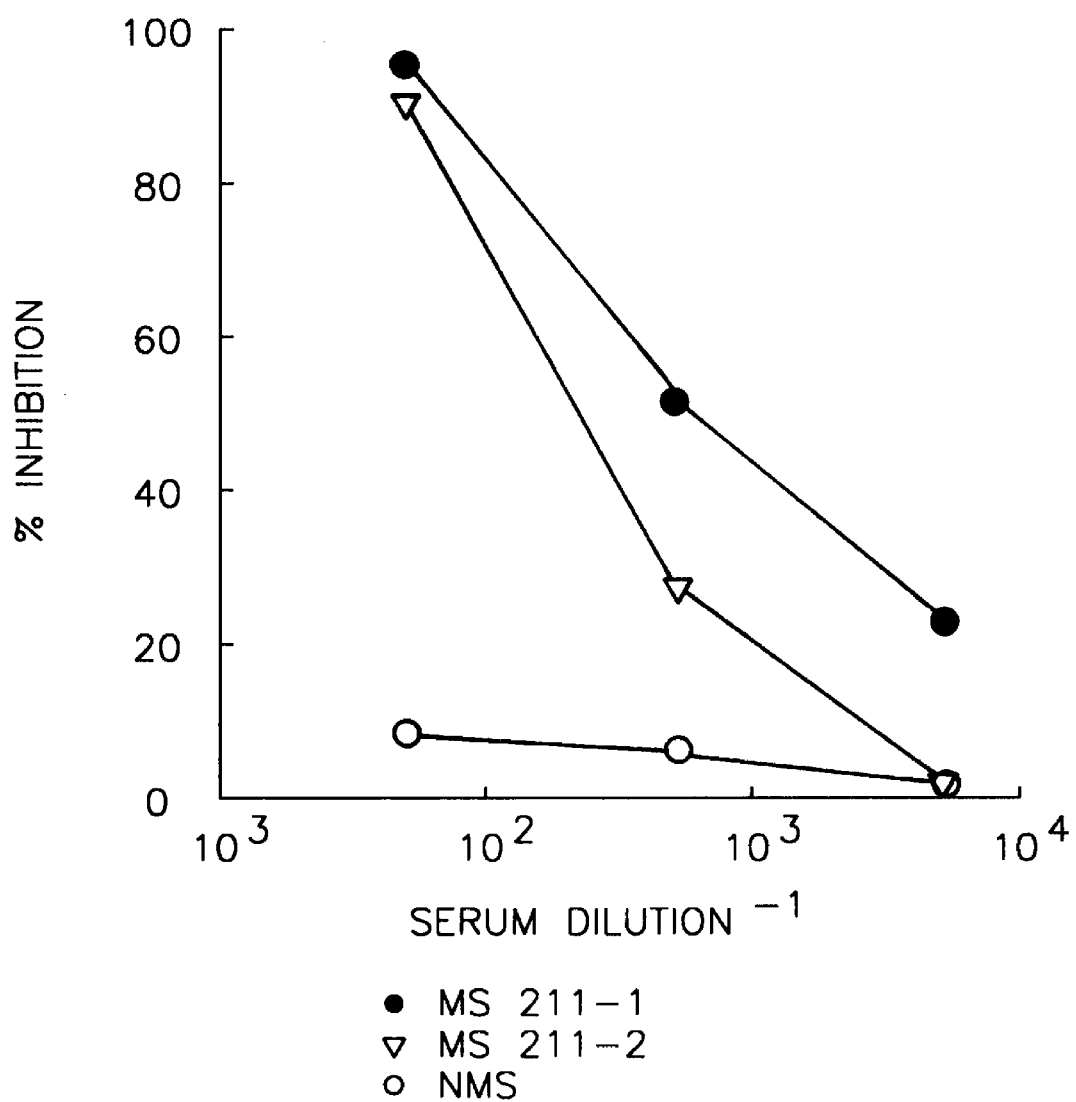
FIG. 7: Inhibition of $^{125}$1-IL-12 Binding to IL-12 (IL-12R) Receptor by Mouse Anti-IL-12R Antiserum

Mice immunized with PHA-activated PBMCs developed an immune response against the human IL-12R as determined by inhibition of $^{125}$I-IL-12 binding to PHA-activated PBMCs (FIG. 7) and immunoprecipitation of the complex of $^{125}$I-IL-12 crosslinked to IL-12R (data not shown). The dilutions for half-maximal inhibition of $^{125}$I-IL-12 binding to PHA-activated.,PBMCs were 1/500 and 1/250 for animals 211-1 and 211-2, respectively (FIG. 7). These antisera also neutralized IL-12 biologic activity as measured in a PHA-lymphoblast proliferation assay (data not shown). Spleen cells isolated from these mice were fused with SP2/0 myeloma cells and the resulting hybridomas were initially screened for IL-12R specific antibodies by immunoprecipitation of the $^{125}$I-IL-12/IL-12R complex and by inhibition of $^{125}$I-IL-12 binding to IL-12R.

For FIG. 7, ten fold serial dilutions of mouse anti-IL-12R immune serum (#211-1 and #211-2) and normal mouse serum (NMS) were preincubated with PHA-activated PBMC for-60 min at RT (room temperature) before addition of $^{125}$I-IL-12 (100 pM). After addition of $^{125}$I-IL-12, the reaction was incubated for 1–2 hrs at RT and the cell bound radioactivity was determined. The data are expressed as the % Inhibition of $^{125}$I-IL-12 binding in the presence of the immune serum when compared to the specific binding in the absence of serum.

EXAMPLE 13

Identification and Characterization of Monoclonal Anti-IL-12R Antibodies

Figure 8:
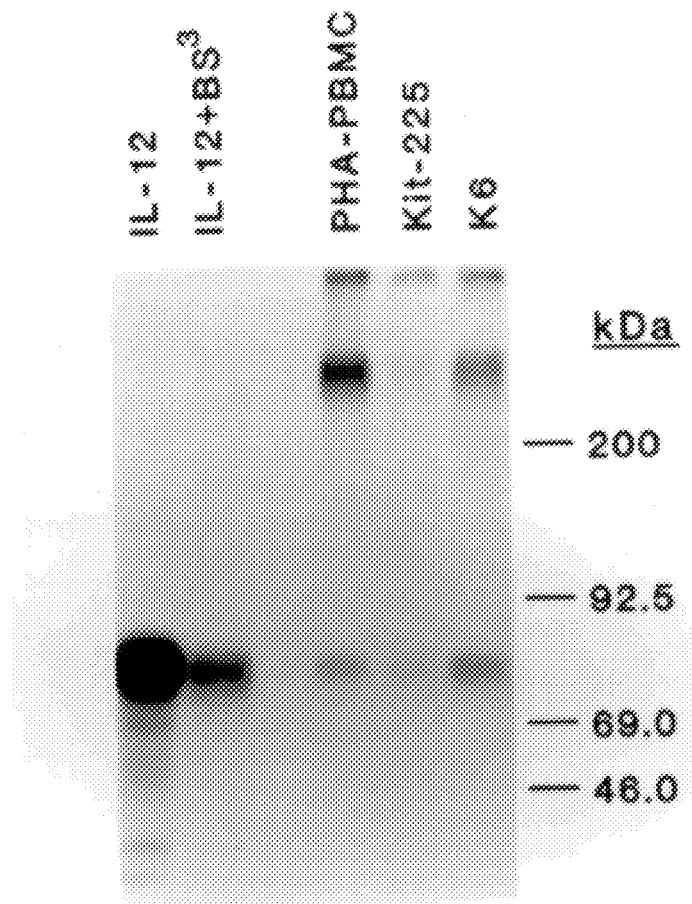
FIG. 8: Characterization of: the IL-12 Binding Proteins on IL-12R Positive Human cells by Affinity-Crosslinking

The immunoprecipitation assay identified 13 hybridomas secreting putative non-neutralizing anti-IL-12R antibodies, whereas the IL-12R binding assay identified 3 putative neutralizing anti-IL-12R antibodies (Table 1). The immunoprecipitation assay measured the ability of the putative anti-IL-12R antibodies that are immobilized on a solid phase to capture the solubilized complex of $^{125}$I-IL-12/IL-12R. To verify that the radioactivity immunoprecipitated by the immobilized antibody was present in the complex of $^{125}$I-IL-12/IL-12R, the immunoprecipitated proteins were solubilized, separated by SDS-PAGE and visualized by autoradiography. The preparations of the $^{125}$I-IL-12/IL-12R complexes solubilized from PHA-activated PBMC, Kit-225 and K6 cells were resolved into two major radioactive bands, 210–250 KDa and 75 KDa (FIG. 8). The 210–250 KDa and 75 KDa complexes were identified as the $^{125}$I-IL-12/IL-12R complex and $^{125}$I-IL-12 not complexed with the receptor, respectively (FIG. 8). See also R. Chizzonite et al., J. Immunol. 148:3117 (1992). The radioactive 75 KDa band visualized from the cell extracts co-migrated with $^{125}$I-IL-12, indicating that it represented $^{125}$I-IL-12 that bound but was not covalently crosslinked to IL-12R. The 210–250 KDa band was not a covalent crosslinked oligomer of $^{125}$I-IL-12 because it is not produced when the crosslinking agent BS3 was added directly to $^{125}$I-IL-12 (FIG. 8).

Hybridoma cells secreting putative anti-IL-12R antibodies were then cloned by limiting dilution and screened by both the immunoprecipitation and inhibition of binding assays that identify non-neutralizing and neutralizing antibodies, respectively. During this cloning and screening process, hybridoma lines secreting putative neutralizing anti-IL-12R antibodies were not recovered, whereas non-neutralizing antibodies were recovered from both the original immunoprecipitation and inhibitory positive hybridomas. After this initial identification and cloning, a direct binding assay was used to determine if the non-neutralizing antibodies only bound to cells expressing IL-12R. This assay demonstrated that the non-neutralizing antibodies could be divided into 2 classes, those that bound only IL-12R positive human cells and those that bound to most human cells (data not shown). Representative antibodies from each class, 2-4E6 and 2C6, respectively, were produced in ascites fluid, purified by protein G affinity chromatography and extensively characterized.

For FIG. 8, PHA-activated PBMC (PHA-PBMC), Kit-225 (Kit-225) and K6 (K6) cells (1×10$^7$ cells/ml) were incubated with $^{125}$I-IL-12 (100–500 pM) for 2 hrs at room temperature in the absence or presence of 25 nM unlabeled IL-12. Cells were then washed, affinity crosslinked with BS3 (0.4 mM final concentration) and a cell extract prepared as described. The cell extract was precipitated with wheat germ lectin bound to solid supports as described. The precipitated proteins were released by treatment with sample buffer and analyzed by SDS-PAGE and autoradiography on a 8.0% slab gel. The complex of $^{125}$I-IL-12 crosslinked to the IL-12 receptor migrates as a single major band of approximately 210–250 KDa. The band migrating at 75 KDa is $^{125}$I-IL-12 that was bound but not crosslinked to the IL-12 receptor. $^{125}$I-IL-12 (IL-12) and $^{125}$I-IL-12 that was treated with the BS3 crosslinker (IL-12/BS3) were electrophoresed in parallel lanes as markers for the migration of the 75 KDa IL-12 heterodimer and for any oligomers of IL-12 that may form with the BS3 crosslinker. The molecular sizes indicated in the margins were estimated from standards run in parallel lanes. Exposure time was 7 days.

TABLE 1

INITIAL IDENTIFICATION OF HYBRIDOMAS SECRETING ANTI-IL-12 RECEPTOR ANTIBODIES: SPLENOCYTES FROM MICE #211-1 AND #211-2

| | HYBRIDOMA/ANTIBODY | I.P. ASSAY[1] | INHIBITION |
|---|---|---|---|
| | | (cpm bound) | ASSAY[2] |
| | IL-12R 2C6[3] | 1900 | – |
| 211-1 | 1A5 | 722 | – |
| | 4E6 | 840 | – |
| | 5C1 | 312 | + |
| 211-2 | 3B1 | 1323 | – |
| | 4A3 | 2172 | – |
| | 4D6 | 804 | – |
| | 5D5 | 877 | – |
| | 4A5 | 509 | + |
| | 4C6 | 456 | + |
| | 1D1 | 1395 | – |
| | 5E6 | 2043 | – |
| | 2-4E6 | 2836 | – |
| Control mAb | | 402 | – |

[1]I.P. assay measures the amount of $^{125}$I-IL-12/IL-12R complex bound by the immobilized antibody.
[2]Inhibition assay measures whether the antibody can inhibit $^{125}$I-IL-12 binding to PHA-activated PBMC.
[3]IL-12R 2C6 is an antibody that both immunoprecipitates the $^{125}$I-IL-12/IL-12R complex and binds to many IL-12R positive and negative human cells. This antibody probably recognizes a component closely associated with the IL-12R.

EXAMPLE 14

Characteristics of Monoclonal Anti-IL-12R Antibody 2-4E6 Binding to Natural IL-12R mAb 2-4E6 immunoprecipitates the $^{125}$I-IL-12/IL-12R complex solubilized from PHA-activated human lymphoblasts, Kit-225 and K6 cells (FIG. 9, data shown for PHA-activated PBMC), but does not block $^{125}$I-IL-12 binding to IL-12R expressed on these cells. These data suggested that the 2-4E6 antibody was a non-inhibitory or non-neutralizing anti-IL-12R antibody. To confirm that 2-4E6 was an non-inhibitory antibody specific for the IL-12R, 2-4E6 was labeled with $^{125}$I and direct binding assays were performed with IL-12R positive and negative cells. $^{125}$I-2-4E6 binds to IL-12R bearing cells with an affinity that ranges from 337 pM to 904 pM and identifies between 1500 and 5000 binding sites per cell (PHA-activated PBMC, FIGS. 10A AND 10B; K6 cells, FIGS. 11A and 11B). IL-12 does not block $^{125}$I-2-4E6 from binding to PHA-activated PBMCs and confirms that 2-4E6 is a non-inhibitory/non-neutralizing antibody (FIG. 12). $^{125}$I-2-4E6 binds to other cells expressing IL-12R, such as Kit 225, and YT cells, but does not bind to IL-12R negative cells (non-activated human PBMC, MRC-5 fibroblasts and HL-60 cells (Table 2).

Equilibrium binding assays have demonstrated that $^{125}$I-IL-12 identifies 3 separate binding sites on the surface of PHA-activated PBMCs, Kit-225 and K6 cells (FIG. 13, data for K6 cells and Table 2). Analysis of this binding data by the method of Scatchard shows these affinities are approximately 5–20 pM, 50–200 pM and 2–6 nM, respectively. The total number of $^{125}$I-IL-12 binding sites per cell are approximately 1500 to 5000, which is in good agreement with the total number of binding sites identified by $^{125}$I-2-4E6 (Table 2). The data also suggests that 2-4E6 recognizes the low affinity (2–5 nM) binding component of the IL-12 receptor in much the same manner that the anti-TAC antibody recognizes the low affinity component (p55 subunit) of the IL-2 receptor.

Figure 15:
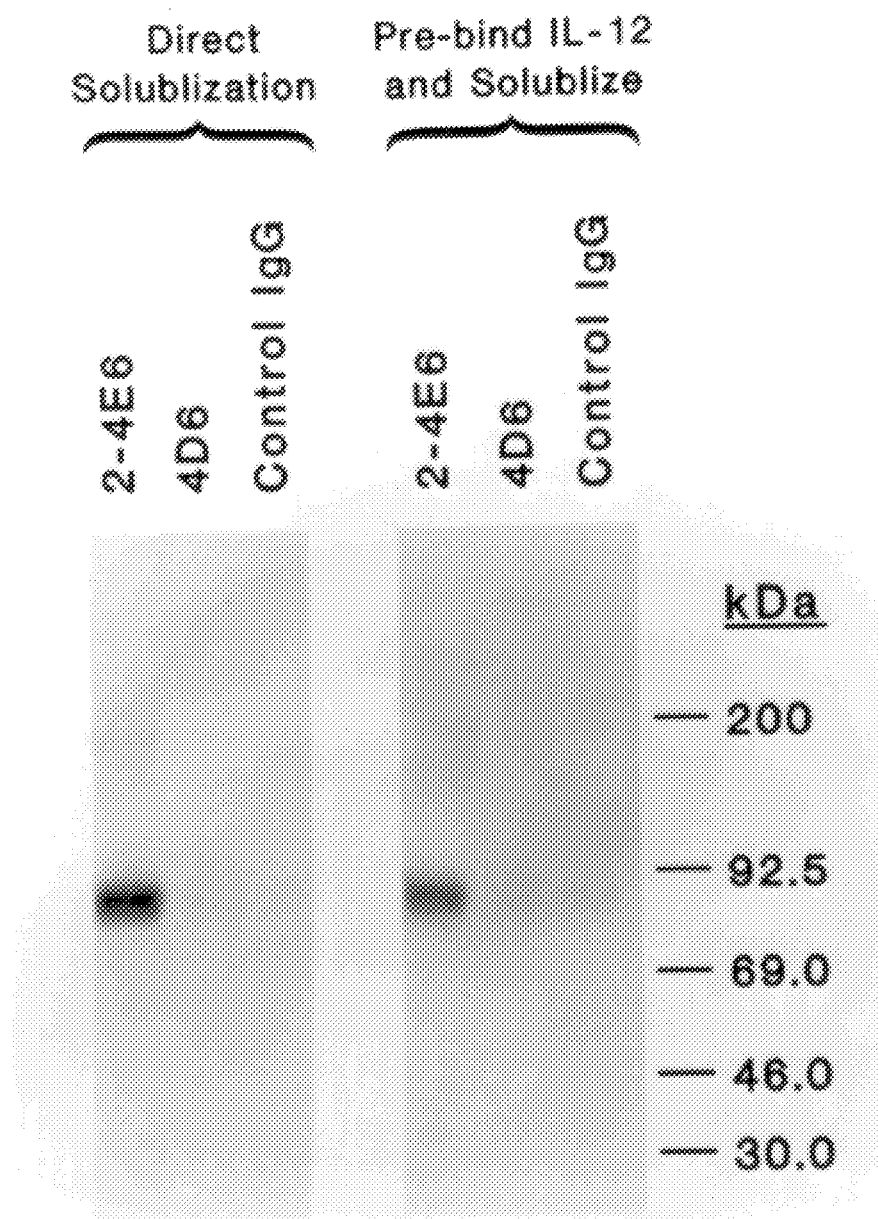
FIG. 15: Western Blot Analysis of Detergent Solubilized IL-12R with mAb 2-4E6

Since the data indicated that mAb 2-4E6 was a non-neutralizing antibody specific for the IL-12R, the molecular weight and $^{125}$I-IL-12 binding characteristics of the protein (s) immunoprecipitated by mAb 2-4E6 from the surface of IL-12R positive cells was investigated. The steady state binding of $^{125}$I-IL-12 to proteins immunoprecipitated by immobilized 2-4E6 from solubilized extracts of PHA-activated PBMCs, Kit-225 and K6 cells was saturable and specific (FIG. 14, data for extracts from K6 cells). Transformation of the binding data by the method of Scatchard revealed a single site with an apparent affinity of 188 pM. The proteins immunoprecipitated by 2-4E6 from the cell extracts were resolved by SDS-PAGE, transferred to nitrocellulose membrane and probed with $^{125}$-2-4E6 in a western blot. On the western blot, $^{125}$I-2-4E6 binds to an approximately 90 KDa protein, that is only immunoprecipitated by 2-4E6 and not by an anti-IL-12 antibody or a control antibody (FIG. 15, data shown for PHA-activated PBMCs). In summary, all the data demonstrated that mAb 2-4E6 bound a protein on the surface of IL-12R positive cells that was approximately 90 KDa and bound $^{125}$I-IL-12 in a specific manner.

Figure 9:
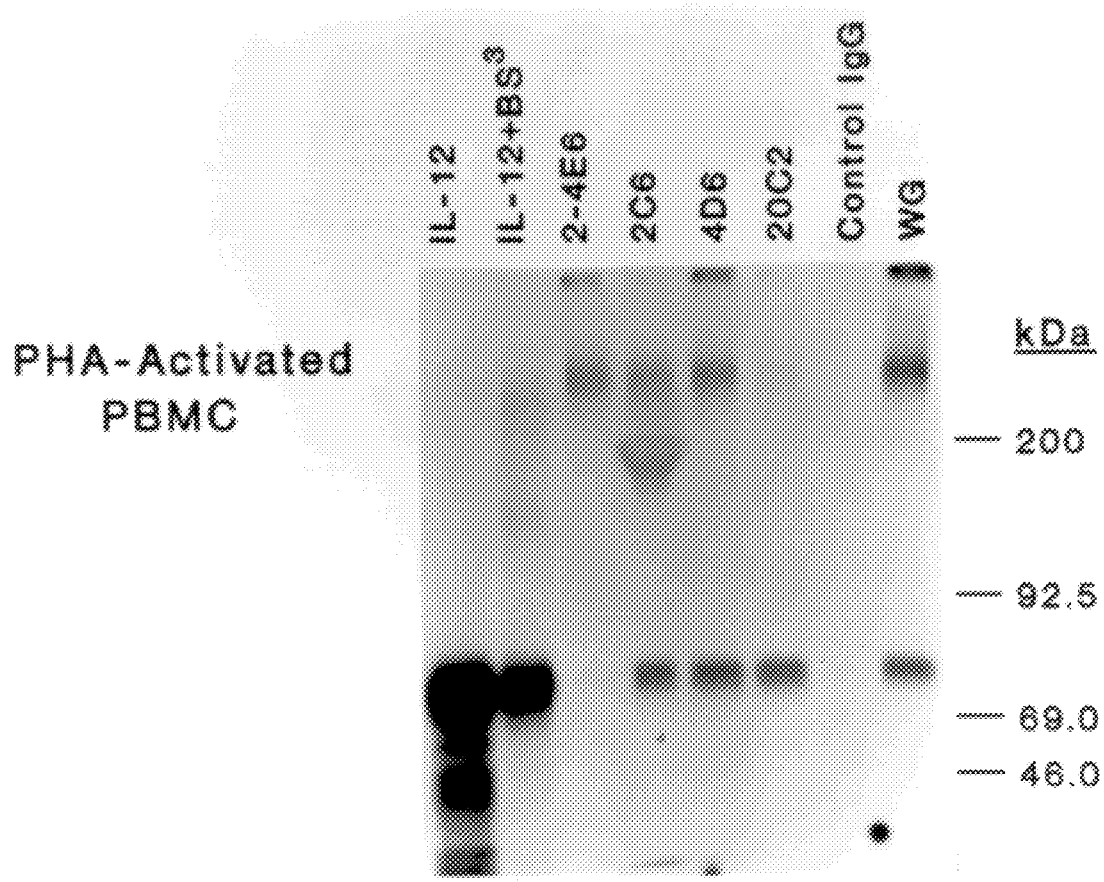
FIG. 9: Immunoprecipitation of the Solubilized $^{125}$I-IL-12/IL-12R Crosslinked Complex by Anti-IL-12R Antibodies

For FIG. 9, soluble complexes of $^{125}$I-IL-12/IL-12R were prepared from PHA-activiated human PBMC as detailed herein (see also FIG. 8) and immunoprecipitated by immobilized antibodies, 2-4E6, 2C6, 4D6, 20C2 and control. The soluble complexes were also precipitated with wheat germ lectin immobilized on crosslinked agarose. The precipitated proteins were analyzed as described herein and in FIG. 8. Antibodies 4D6 and 20C2 are non-neutralizing and neutralizing anti-IL-12 antibodies, respectively. 4D6 immunoprecipitates $^{125}$I-IL-12/IL-12R complex and free $^{125}$I-IL-12, whereas 20C2 only immunoprecipitates free $^{125}$I-IL-12. Both 2-4E6 and 2C6 recognize the $^{125}$I-IL-12/IL-12R complex. $^{125}$I-IL-12 (IL-12) and $^{125}$I-IL-12 that was treated with the BS3 crosslinked (IL-12/BS3) were electrophoresed in parallel lanes as markers for the migration of the 75 KDa IL-12 heterodimer and for any oligomers of IL-12 that may form with the BS3 crosslinker. The molecular sizes indicated in the margins were estimated from standards run in parallel lanes. Exposure time was 7 days.

Figure 10B:
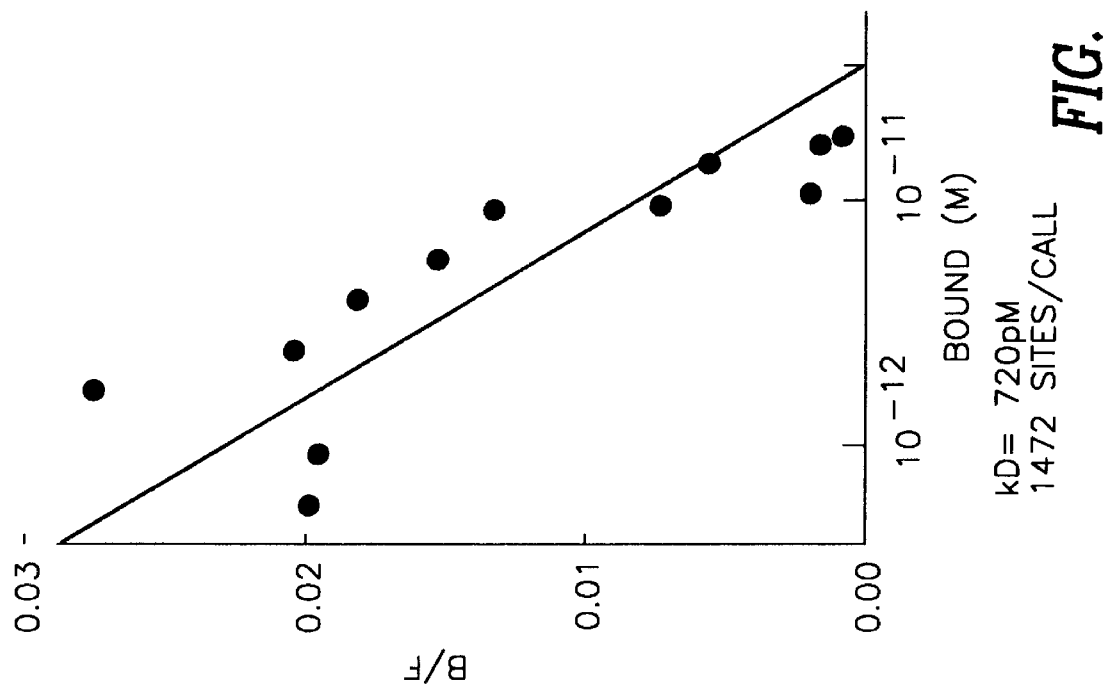
FIGS. 10A and 10B: Equilibrium binding of $^{125}$I-2-4E6 to PHA-activated PBMC at Room Temperature
Figure 10A:
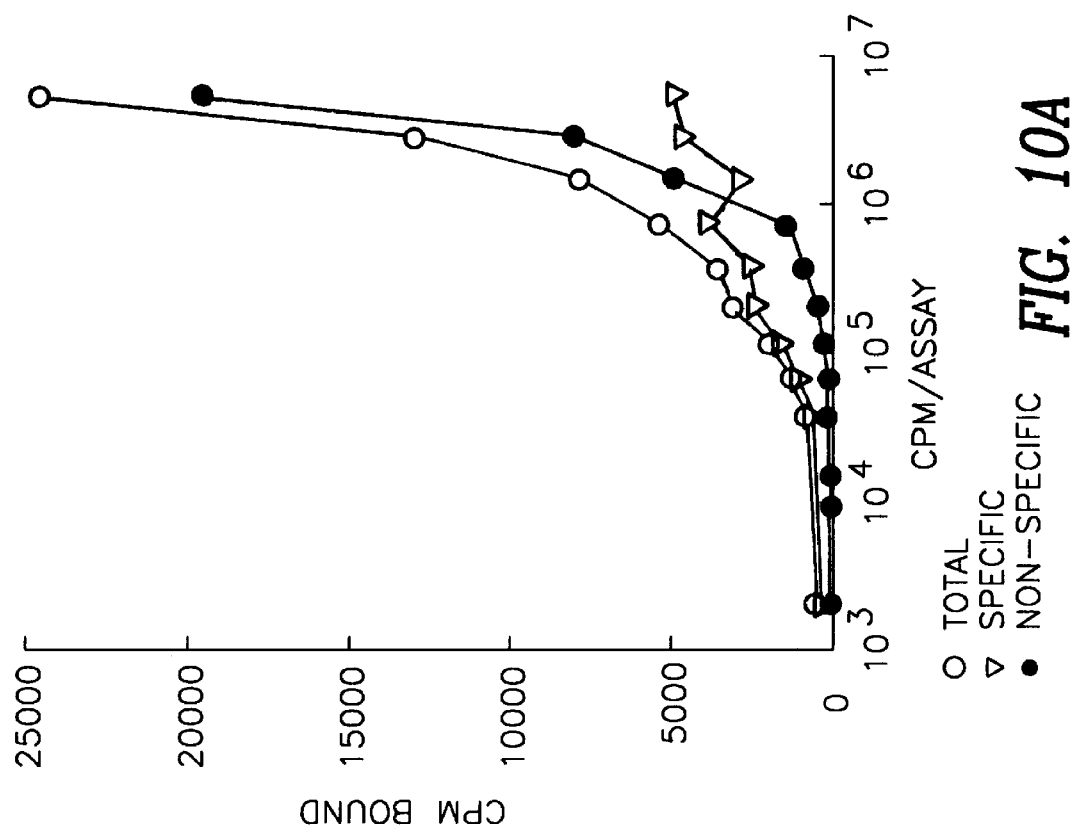

For FIGS. 10A and 10B, Lymphoblasts (1×10$^6$ cells) were incubated for 2 hrs at room temperature with increasing concentrations of $^{125}$I-2-4E6 in the absence (○) or presence (●) of 25 nM unlabeled 2-4E6. Total (○) and non-specific (●) cell bound radioactivity were determined as described. Specific binding of $^{125}$I-2-4E6 (▼) was calculated by subtracting non-specific binding from total binding. The right hand panel shows analysis of the binding data according to the method of Scatchard as determined by LIGAND with a single-site model.

Figure 11B:
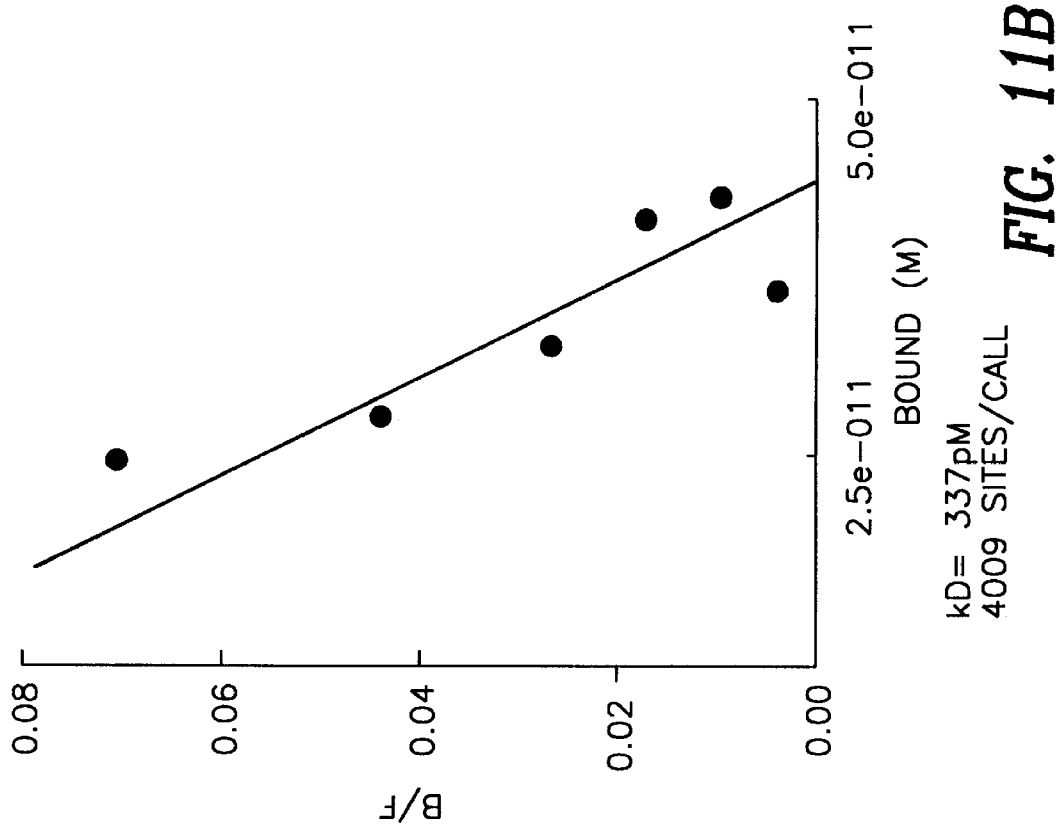
FIGS. 11A and 11B: Equilibrium Binding of $^{125}$I-2-4E6 to Human K6 Cells at Room Temperature
Figure 11A:
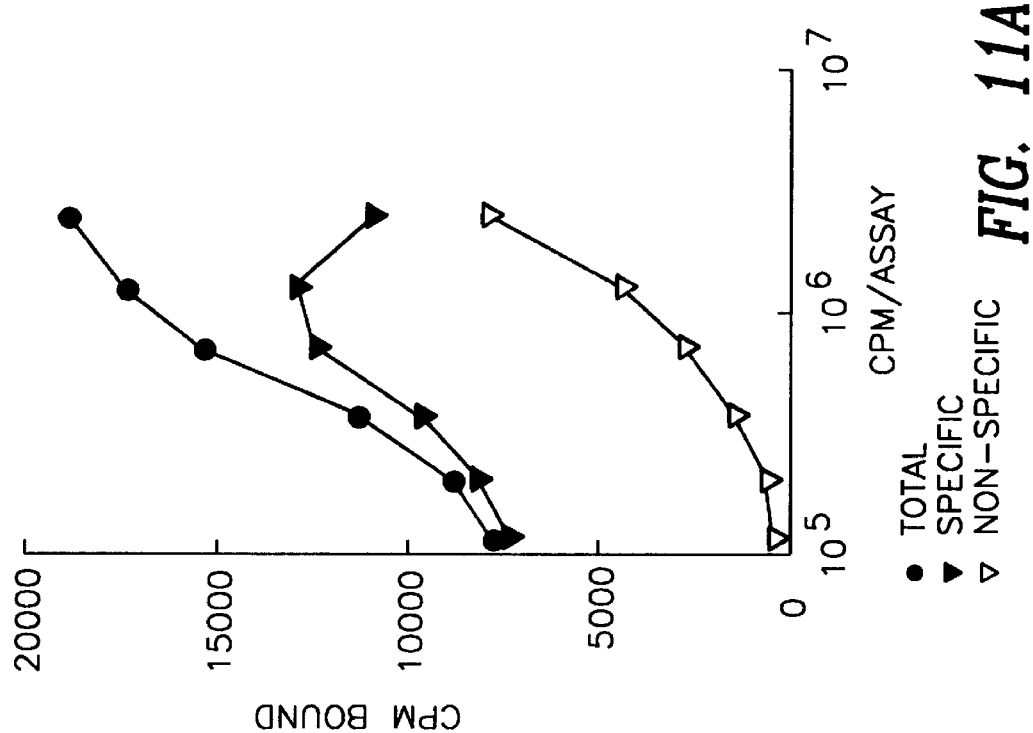
Figure 12:
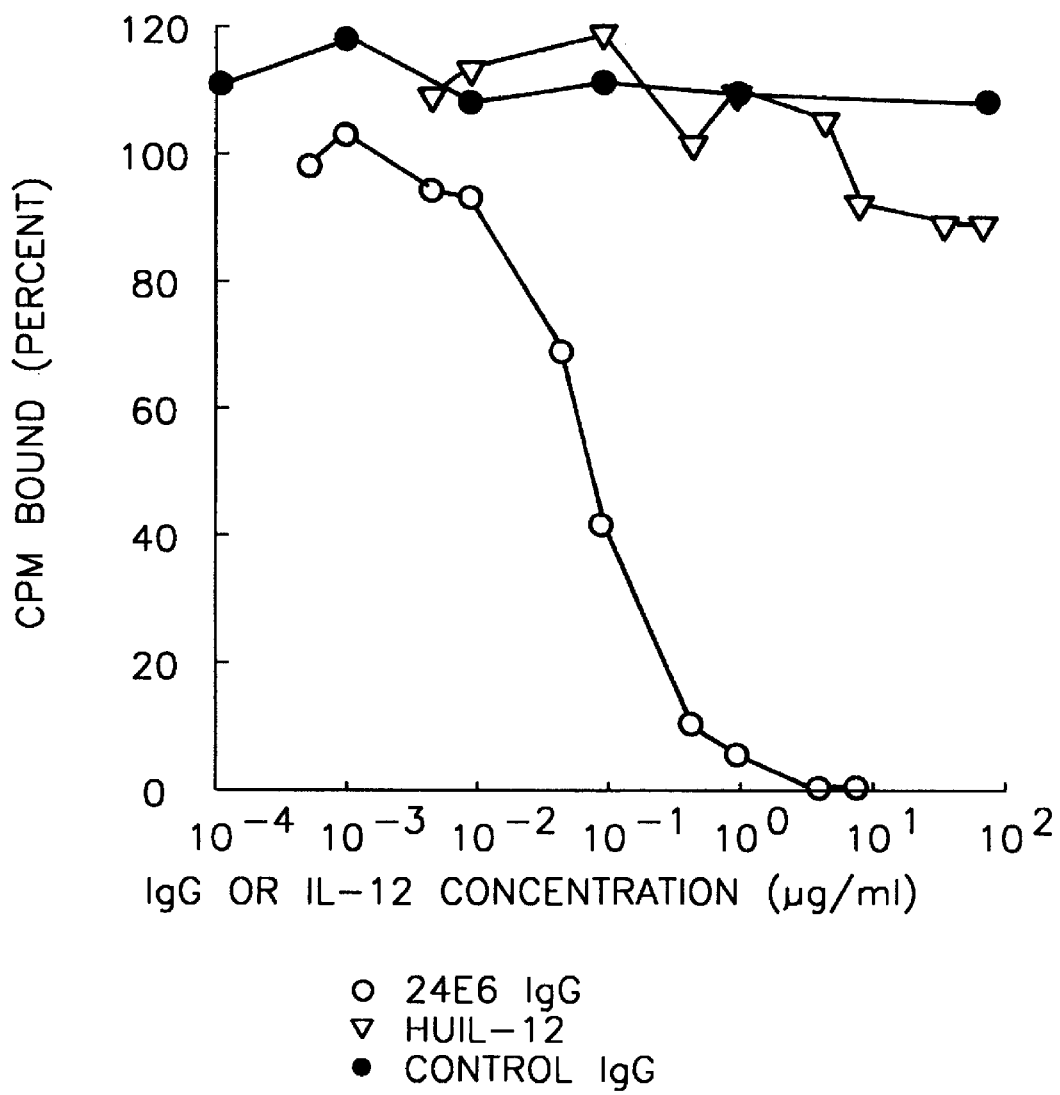
FIG. 12: Inhibition of $^{125}$I-2-4E Binding to K6 Cells by Purified 2-4E6 (24E6), Human IL-12 (HUIL-12) and Control Antibody (Control IgG)

For FIGS. 11A and 11B, K6 cells (1×10$^6$ cells) were incubated for 2 hrs at room temperature with increasing concentrations of $^{125}$I-2-4E6 in the absence (●) or presence (▽) of 25 nM unlabeled 2-4E6. Total (●) and non-specific (▽) cell bound radioactivity were determined as described. Specific binding of $^{125}$I-2-4E6 (▼) was calculated by subtracting non-specific binding from total binding. The right hand panel shows analysis of the binding data according to the method of Scatchard as determined by LIGAND with a single-site model.

For FIG. 12, The data are expressed as the amount of 125I-2-4E6 bound [CPM BOUND (Percent)] to the cells in the presence of the indicated concentrations of unlabeled antibody or IL-12 when compared with the total specific binding in the absence of unlabeled competitor.

Figure 13B:
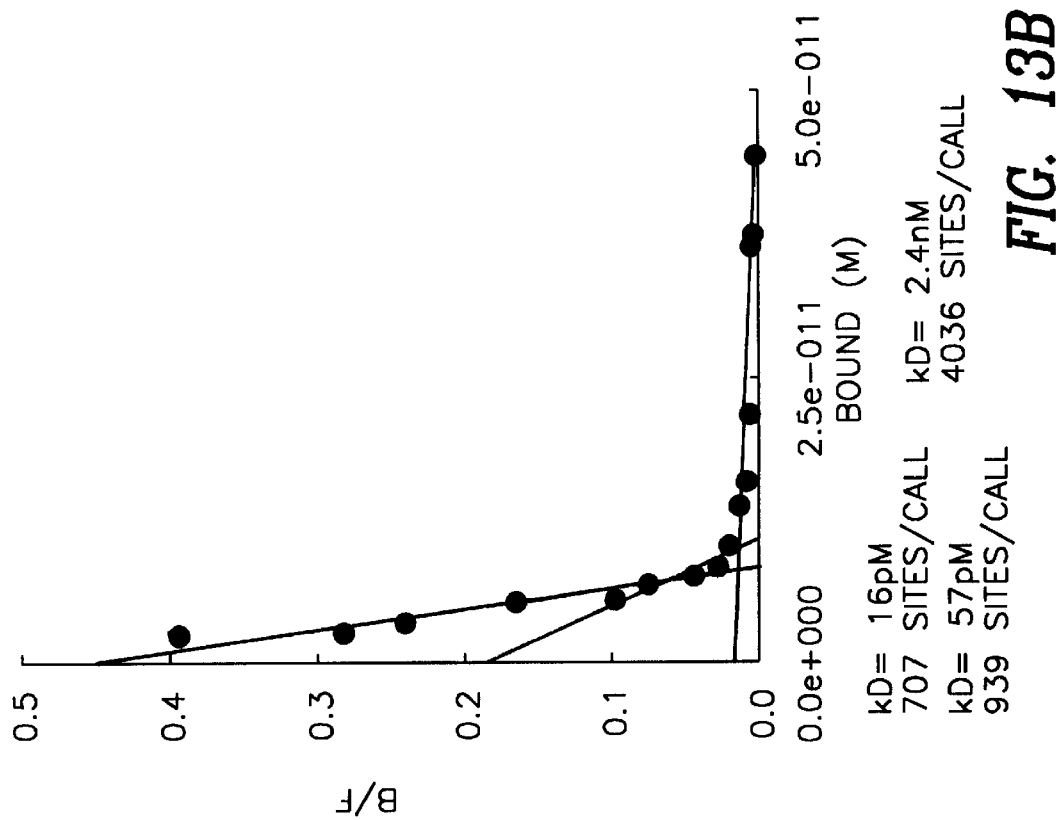
FIGS. 13A and 13B: Equilibrium Binding of $^{125}$I-IL-12 to Human K6 Cells at Room Temperature
Figure 13A:
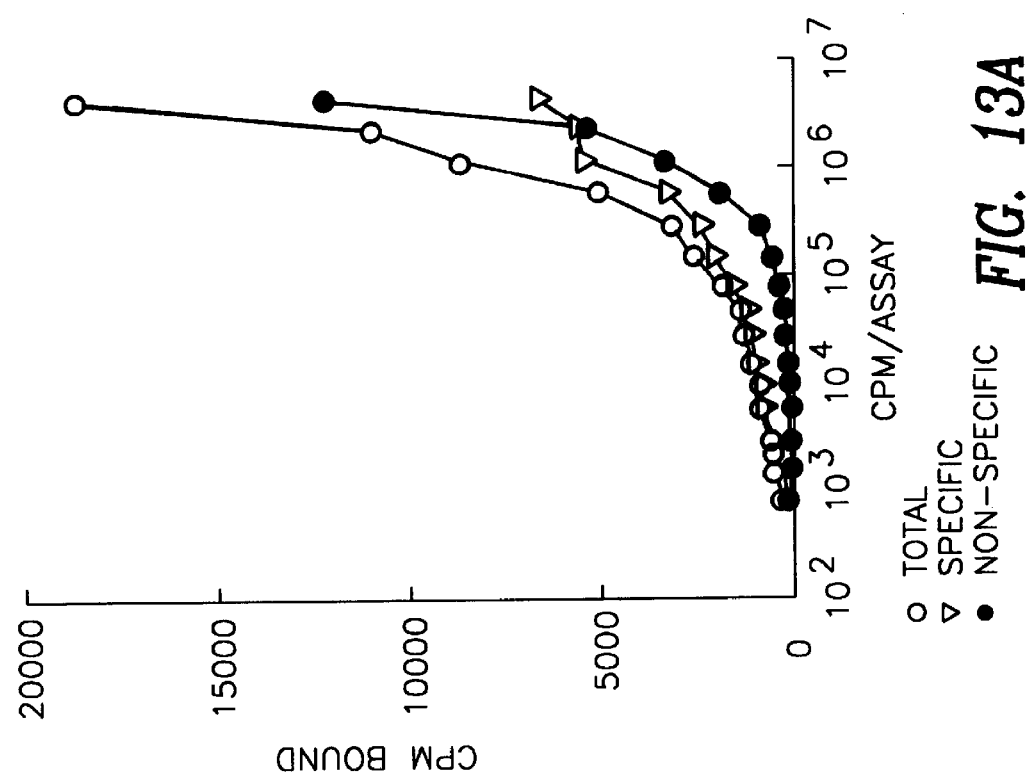

For FIGS. 13A and 13B, K6 cells (1×10$^6$ cells) were incubated for 2 hrs at room temperature with increasing concentrations of $^{125}$I-IL-12 in the absence (○) or presence (●) of 50 nM unlabeled IL-12. Total (○) and non-specific (●) cell bound radioactivity were determined as described. Specific binding of $^{125}$I-IL-12 (▽) was calculated by subtracting non-specific binding from total binding. The right hand panel shows analysis of the binding data according to the method of Scatchard as determined by LIGAND with a single-site model.

For FIGS. 14A and 14B, K6 cells (1.5×10$^8$ cells/ml) were solubilized with 8 mM CHAPS extraction buffer and the cell extract (0.2 ml) was immunoprecipitated for 16 hrs at 4° C. with mAb 2-4E6 immobilized on goat anti-mouse IgG coupled to agarose as described. Following this incubation, the beads were pelleted, washed and resuspended in IP buffer containing $^{125}$I-IL-12 at concentrations ranging from 7 pM to 7.5 nM. The IL-12R immobilized on the 2-4E6 coated beads was incubated with $^{125}$I-IL-12 for 2 hrs at RT and IL-12R bound radioactivity was determined in the presence of 50 nM unlabeled IL-12. The right hand panels show analysis of the binding data according to the method of Scatchard as determined by LIGAND with a single-site model.

For FIG. 15, PHA-activated PBMC (1×10$^8$ cells/ml) were solubilized with 8 mM CHAPS extraction buffer and the cell extract (1 ml) was immunoprecipitated as described in FIGS. 14A and 15B. Following this incubation, the beads were pelleted, washed and the bound proteins released by treatment with 0.1M glycine pH 2.3. The released proteins were separated by non-reducing SDS/PAGE on 8% gels transferred to nitrocellulose membrane and probed with $^{125}$I-2-4E6 as described. The molecular sizes indicated in the margins. were estimated from molecular weight standards (Amersham Prestained High Molecular Weight Standards) run in parallel lanes. Exposure time was 7 days.

TABLE 2

COMPARISON OF THE BINDING OF IL-12 AND 2-4C6 TO HUMAN CELLS EXPRESSING IL-12 RECEPTOR

| | IL-12 BINDING[1] | | 2-4E6 BINDING[2] | |
|---|---|---|---|---|
| CELL TYPE | $K_D$ (nM) | Sites/cell | $K_D$ (nM) | Sites/cell |
| Human Cells | | | | |
| non-activated human PBMC[3] | none | detected | none | detected |
| PHA-PBMC (5–7 days) (3 sites) | 0.018 0.084 1.800 | 312 501 1406 | 0.745 | 1472–2246 |
| K6 cells (3 sites) | 0.016 0.057 2.400 | 707 939 4036 | 0.489 | 3116–5259 |
| Kit-225 (3 sites) | 0.023 0.210 2.360 | 100 250 755 | 0.594 | 1950 |

TABLE 2-continued

COMPARISON OF THE BINDING OF IL-12 AND 2-4C6
TO HUMAN CELLS EXPRESSING IL-12 RECEPTOR

| CELL TYPE | IL-12 BINDING[1] | | 2-4E6 BINDING[2] | |
|---|---|---|---|---|
| | $K_D$ (nM) | Sites/cell | $K_D$ (nM) | Sites/cell |
| YT cells (2 sites) | 0.006 0.109 | 24 117 | 0.904 | 4522 |
| RAJI cells | none | detectable | 0.450 | 561 |
| MRC-5 | none | detectable | none | detectable |
| HL-60 | none | detectable | none | detectable |

[1]Steady state $^{125}$I-IL-12 binding assays. Apparent dissociation constant ($K_D$) and binding sites per cell have been calculated by transformation of the data by the method of Scatchard.
[2]Steady state $^{125}$I-2-4E6 binding assays. Data transformed by the method of Scatchard.
[3]Human peripheral blood mononuclear cells (PBMC) were activated with PHA as described in the methods (PHA-PBMC).

EXAMPLE 15
mAb 2-4E6 Binding To Human Recombinant IL-12R Expressed in COS Cells.

Figure 4A:
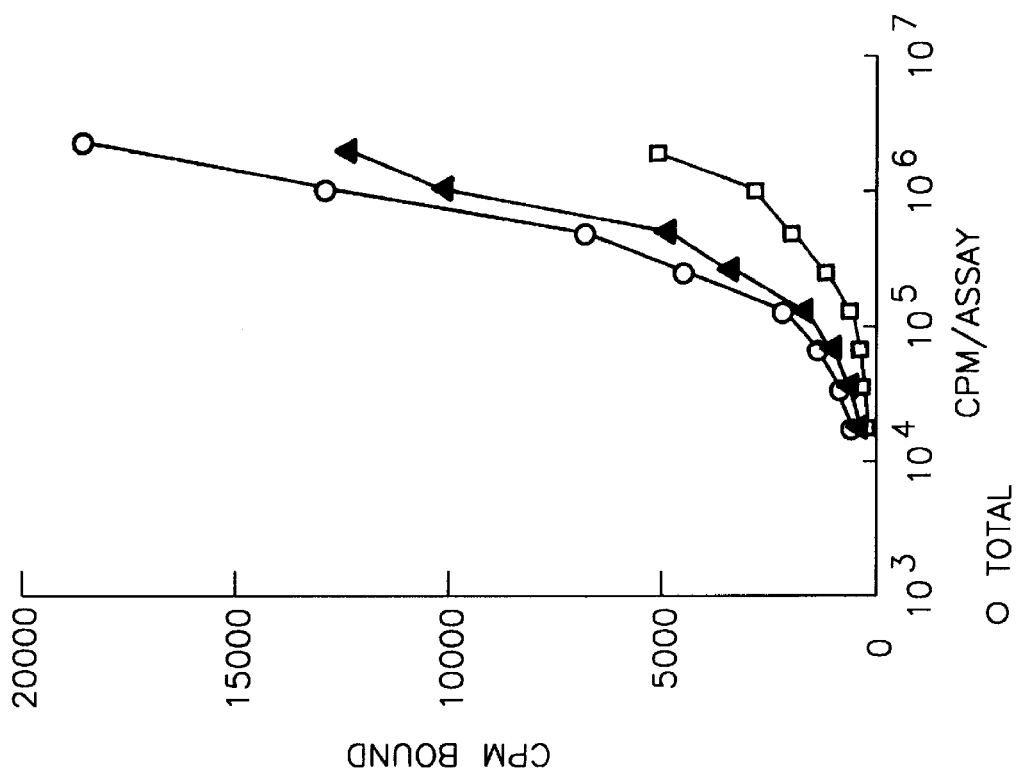
Figure 4D:
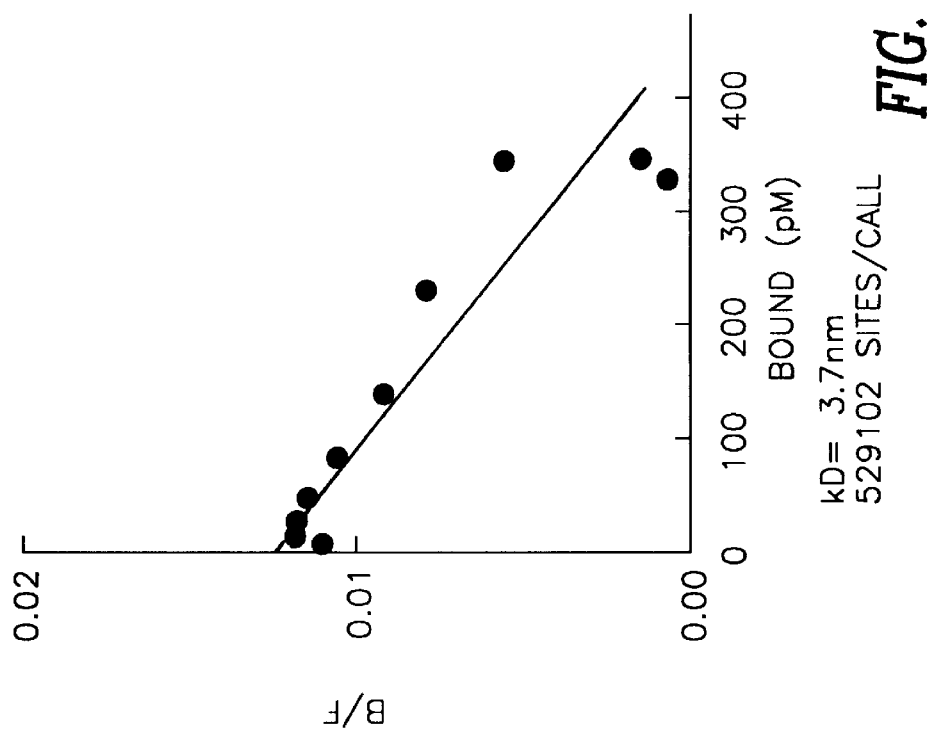
FIG. 4C and 4D: Scatchard analysis of 2-4E6 antibody binding to recombinant human IL-12 receptor expressed in COS cells.
Figure 4C:
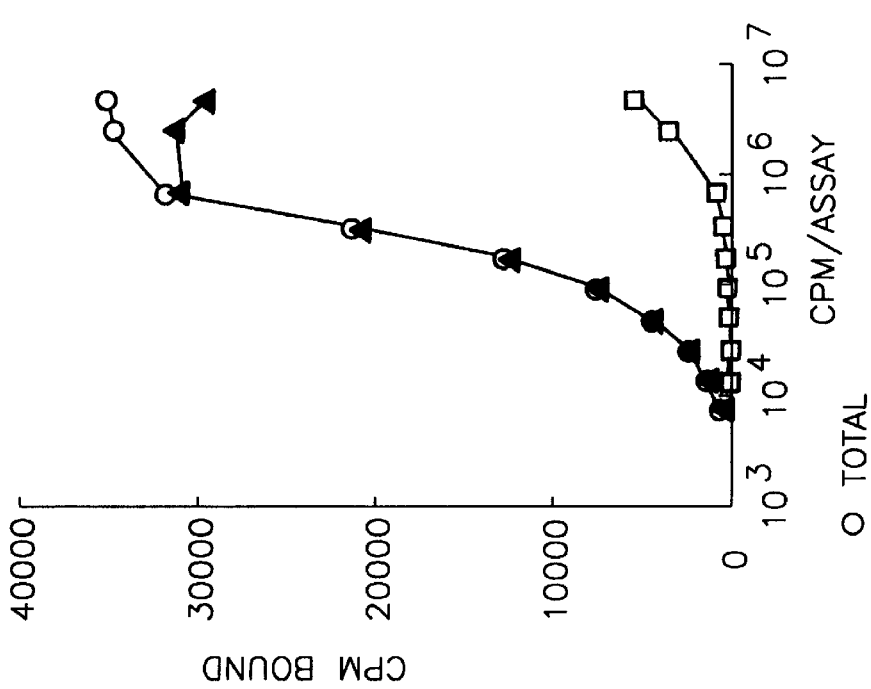

The characteristics of the protein bound by mAb 2-4E6 fulfilled standard criterion for an IL-12R and therefore 2-4E6 was used in an expression cloning strategy to isolate a cDNA coding for the human IL-12R. A cDNA coding for the human IL-12R was isolated by this method (U. Gubler and A. O. Chua, unpublished observations). The IL-12R cDNA was engineered in a mammalian cell expression vector, transfected into COS-7 cells and the specificity for binding of $^{125}$I-IL-12 and $^{125}$I-2-4E6 was determined. Steady state binding of $^{125}$I-IL-12 to the rIL-12R expressing COS cells identifies a single binding site with an apparent affinity of 2–6 nM and approximately 150,000 sites/cell (FIGS. 4A and 4B). This low affinity IL-12 binding site corresponds to the low affinity site seen in the binding assays with human cells that naturally express IL-12R. The binding of $^{125}$I-2-4E6 to, rIL-12R expressed in the COS cells is saturable and specific and identifies approximately 500,000 sites/cell (FIGS. 4C and 4D). COS cells transfected with an unrelated plasmid do not bind either $^{125}$I-IL-12 or $^{125}$I-2-4E6 (data not shown). These data demonstrated unequivocally that mAb 2-4E6 was specific for the low affinity component of the IL-1 2R.

For FIGS. 4A and 4B, COS cells were transfected with a plasmid expressing human rIL-12R as. described. Three days later, transfected cells ($1\times10^4$ cells) were incubated for 2 hrs at room temperature with increasing concentration of $^{125}$I-IL-12 in the absence (o) or presence (□) of 50 nM unlabeled IL-12. Total (o) and non-specific (□) cell bound radioactivity were determined as described. Specific binding of $^{125}$I-IL-12 (▲) was calculated by subtracting non-specific binding from total binding. The right hand panel shows analysis of the binding data according to the method of Scatchard as determined by LIGAND with a single-site model.

For FIGS. 4C and 4D, COS cells were transfected with a plasmid expressing human rIL-12R as described in Methods. Three days later, transfected cells ($1\times10^4$ cells) were incubated for 2 hrs at room temperature with increasing concentrations of $^{125}$I-2-4E6 in the absence (o) or presence (□) of 50 nM unlabeled 2-4E6. Total (o) and non-specific (□) cell bound radioactivity were determined as described. Specific binding of $^{125}$I-2-4E6 (▲) was calculated by subtracting non-specific binding from total binding. The right hand panel shows analysis of the binding data according to the method of Scatchard as determined by LIGAND with a single-site model.

EXAMPLE 16
Analysis of mAb 2-4E6 Binding to IL-12R Positive Human Cells by Fluorescence Activated Cell Sorting (FACS)

Figure 16A:
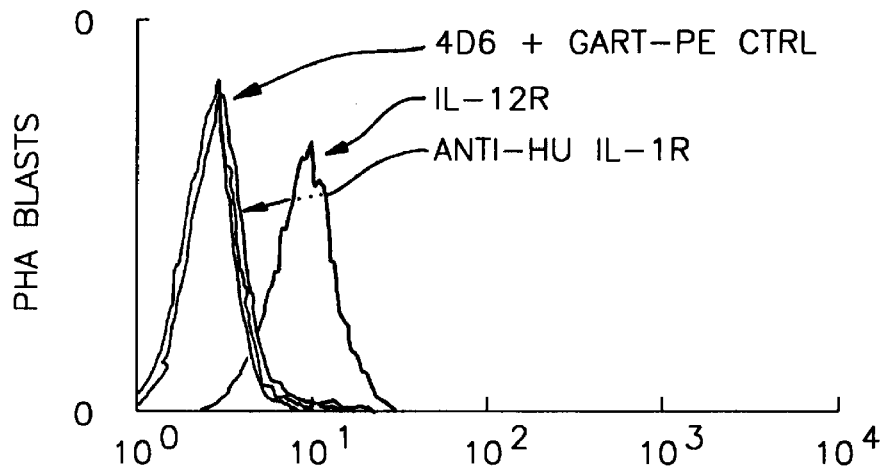
FIGS. 16A, 16B and 16C: Detection of IL-12 Receptor on Human Cells by Flow Cytometry
Figure 16B:
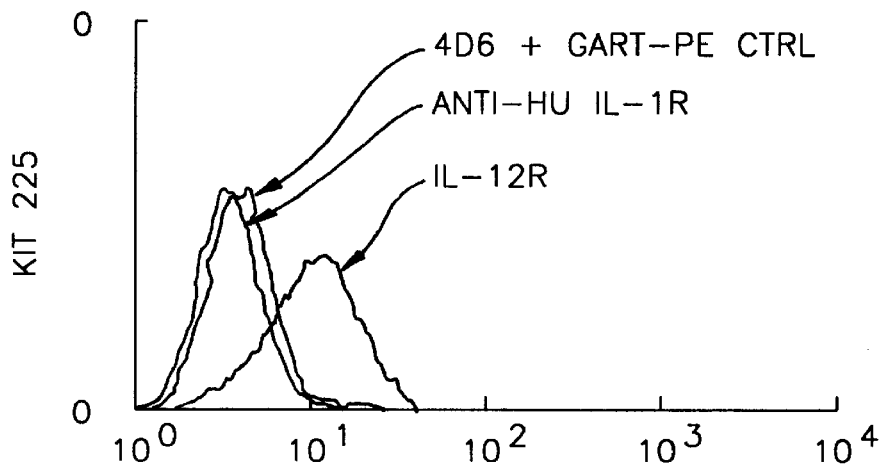
Figure 16C:
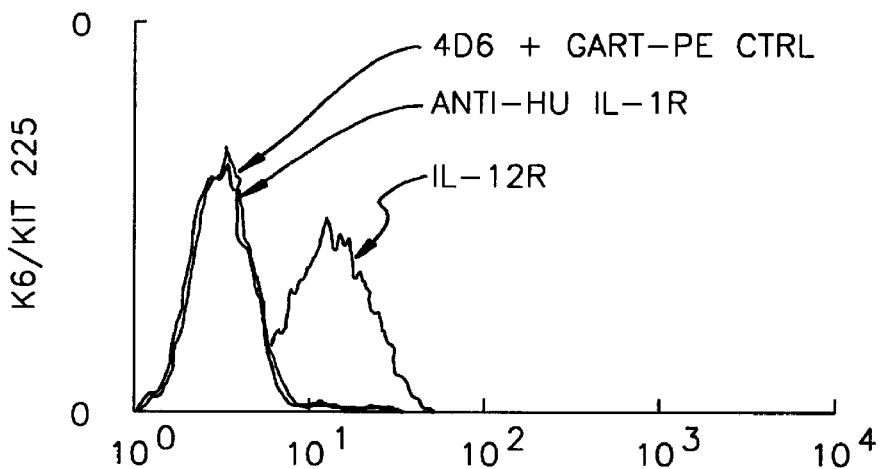

The expression level of IL-12R on human cells could be regulated depending on the activation state of the cells, the cell cycle or the type of environment from which the cells are isolated. Previous data had demonstrated that PHA activation of- PBMC leads to a gradual rise in IL-12R expression, reaching a maximum at 3–4 days after activation and declining thereafter. Desai et al., J. Immunol., 148:3125 (1992). To investigate the heterogeneity of IL-12R expression on PHA-activated PBMCs, Kit-225 and K6 cells, FACS analysis of IL-12R on these cells was determined with mAb 2-4E6 (FIGS. 16A, 16B, and 16C). The fluorescence intensity of binding of 2-4E6 was specific and indicated that these three cell types expressed approximately equal numbers of IL-12R. Interestingly, the FACS analysis indicated that the cell population was fairly homogenous and did not have one population expressing no or low numbers of IL-12R and a second population that expressed very high numbers of IL-12R.

For FIGS. 16A, 16B, and 16C, Day 4 PHA-activated lymphoblasts, Kit-225 and K6 cells were analyzed for IL-12R expressing cells by the indirect fluorescent antibody-labeling technique described. The figure depicts specific staining for IL-12R obtained in the presence of mAb 2-4E6 (IL-12R) and non-specific staining obtained in the presence of a control antibody specific for IL-1 receptor (anti-Hu IL-1R), a control antibody specific for human IL-12 (4D6+ GART-PE CTRL) and the goat anti-mouse antibody conjugated with PE (GART-PE CTRL).

Cell Culture

Peripheral blood mononuclear cells (PBMC) were isolated from blood collected from healthy donors. The blood was collected into heparinized syringes, diluted with an equal volume of Hank's balanced salt solution (HBSS) and layered over Ficoll-Hypaque. The tubes were spun at 2000 rpm for 20 minutes at room temperature. PBMC at the interface were collected and pelleted at 1500 rpm for 10 minutes through a 15 ml cushion of 20% sucrose in PBS. Pelleted PBMC were resuspended in tissue culture medium and washed twice in the same medium (RPMI 1640 plus 5% serum). Finally, the cells were cultured at $0.5\times1\times10^6$ cells/ml in tissue culture medium plus 1 µg/ml PHA-P (Difco) for 3 days at 37 degrees C. in a 5% $CO_2$ atmosphere. Cells were split 1:1 in culture medium plus 50 U/ml rhuIL-2 (Hoffmann-La Roche Inc.) to yield >95% T-cells. The next day, these cells were used for assessing their responsiveness to IL-12, for radioligand (IL-12) binding assays and in flow cytometry assays for the detection of IL-12 receptors.

Flow cytometric detection of IL-12 receptors on such 4 day activated PHA blasts was performed as follows: the cells were washed twice in PBS and resuspended at $2\times10^6$ cells/ml in PBS plus 2% fetal calf serum and 0.1% sodium azide. All the subsequent steps were carried out at 4 degrees C. $1\times10^6$ cells were incubated in 1 nM human IL-12 for 40 minutes. The cells were washed in FACS buffer and incubated with about 1 µg of biotinylated rat anti human p40 IL-12 subunit antibody 4D6 for 20 minutes. Cells were washed again and resuspended in 100 µl of a 5 µg/ml streptavidin-phycoerythritin conjugate (Fisher Biotech) for 15 minutes. The cells were then washed again before analysis on a FACScan flow cytometer (Becton Dickinson).

Extraction and characterization of RNA

PHA activated cells as described above were harvested at day 2–3 and total RNA was extracted using Guanidinlsothiocyanate/Phenol as described (P. Chomczynski and N. Sacchi, Anal. Biochem., 162:156, 1987). Poly A+ RNA was isolated from the total RNA by one batch adsorption to oligo dT latex beads as described (K. Kuribayashi et al., Nucl. Acids Res. Symposium Series 19:61, 1988). The mass yield of this purification was about 4%.

RNA blots were performed as follows. RNA was fractionated in 1.2% agarose gels under denaturing conditions in the presence of 2.2.M formaldehyde and subsequently transferred to nitrocellulose as described (Molecular Cloning, a Laboratory Manual, second edition, J. Sambrook, E. F. Fritsch, T. Maniatis, Cold Spring Harbor Laboratory Press 1989 (hereinafter "Molecular Cloning Manual")). The RNA blots were hybridized ($7 \times 10^5$ cpm/ml, 30 ml) with labeled probe in 5× SSC (1× SSC=0.15M NaCl –0.015M NaCitrate) —50% formamide—5× Denhardts solution (1× Denhardts= 0.02% polyvinylpyrrolidone, 0.02% Ficoll 400, 0.02% bovine serum albumin fraction V)—0.3 % SDS—250 µg/ml denatured salmon sperm carrier DNA at 37° C. overnight. The probe was generated by random-primer labeling gel-isolated insert from IL-12 receptor cDNA clone No.5 by the method as described in Molecular Cloning Manual. The blots were first quickly rinsed at room temperature in 2× SSC , then washed in 0.1× SSC at 50° C. for 30 minutes, dried and exposed to Kodak XAR film at –70° C. for 3 days.

cDNA library

From the above polyA+ RNA, a cDNA library was established in the mammalian expression vector pEF-BOS as follows: 3 µg of polyA+ RNA were reverse transcribed into single stranded cDNA using RNaseH minus reverse transcriptase (GIBCO BRL Life Technologies Inc., P.O.Box 9418, Gaithersburg, Md. 20898). The resulting mRNA-cDNA hybrids were converted into blunt ended doublestranded cDNAs by established procedures (U. Gubler and A. Chua, in: Essential Molecular Biology Volume II, T. A. Brown, editor, pp. 39–56, IRL Press 1991). BstXI linkers (A. Aruffo and B. Seed, Proc. Nati. Acad. Sci (U.S.A.) 84, 8573, 1987) were ligated to the resulting cDNAs and cDNA molecules>800 base pairs (bp) were selected over a Sephacryl SF 500 column. A Sephacryl SF 500 column (0.8×29 cm) was packed by gravity in 10 mM Tris-HCl pH 7.8-1 mM EDTA-100 mM NaAcetate. BstXI linked cDNA was applied to the column and 0.5 ml fractions were collected. A. small aliquot of each fraction was run on a 1% agarose gel, the gel was dried down and the size distribution of the radioactive cDNA visualized by exposure of the gel to X-ray film. cDNA molecules larger than 800 bp were selected in this fashion, pooled, concentrated by ethanol pxecipitation and subsequently ligated to the cloning vector. The cloning vector was the plasmid pEF-BOS that had been cut with BstXI and purified over two consecutive gels. 300 ng of plasmid DNA were ligated to 30 ng of size selected cDNA from above in 60 µl of ligation buffer (50 mM Tris-HCl pH 7.8-10 mM MgCl$_2$-10 mM DTT-1 mM rATP-25 µg/ml bovine serum albumin) at 15° C. overnight. The following day, the ligation reaction was extracted with phenol, 6 µg of mussel glycogen, were added, and the nucleic acids were precipitated by ethanol. The precipitate was dissolved in water and the precipitation was repeated, followed by a wash with 80% ethanol. Finally, the pellet was dissolved in 6 µl of water and 1 ml aliquots were subsequently electroporated into E. Coli strain DH-10B (BRL). By electroporating 5 parallel aliquots in this fashion, a library of about 10 million recombinants was generated for future use.

Screening for IL-12 receptor cDNAs by panning

The basic principle of the panning method has been described in A. Aruffo and B. Seed, Proc. Natl. Acad. Sci (U.S.A.) 84, 8573, 1987 as discussed below. Ten library aliquots each representing about 50,000 clones were plated on LB amp plates and were grown up overnight. The next day, the colonies from each pool were scraped off into a separate 50 ml aliquot of LB+amp and the cultures were grown for another two hours before plasmid DNA was extracted using QIAGEN plasmid kits. The ten separate DNA pool were then transfected into COS cells, using the DEAE dextran technique (2 million COS cells/9 cm diameter plate and 2.5 µg DNA) (Molecular Cloning Manual). 2 to 3 days later, the COS cells were detached from the plates using 0.5 mM EDTA/0.02% Na Azide in PBS and a single cell suspension was prepared for each pool. The monoclonal anti IL-12 receptor antibody 2-4E6 as discussed above was subsequently bound to the cells in suspension (10 µg/ml in PBS-0.5 mM EDTA-0.02% Na Azide-5% FCS, 1 hour, on ice). The cell suspension was then spun through a layer of 2% Ficoll in the above buffer (tabletop centrifuge, 1000 rpm, 4 minutes) to eliminate the excess unbound antibody and the cells were gently resuspended in the same buffer. The cells from one pool were subsequently added to one bacterial petri dish (9 cm diameter) that had been coated with polyclonal goat anti mouse IgG (20 µg/ml in 50 mM Tris-HCl pH 9.5, RT/OVERNIGHT(ON)) and blocked with 1% BSA in PBS (37 degree C./1 hour). COS cells were panned in this way for 2 hours at RT. Nonadhering cells were then gently washed off with PBS and the remaining adherent cells in the dishes lysed by the addition of 0.8 ml of Hirt lysis solution (0.6% SDS-10 mM EDTA). After transferring to Eppendorf tubes, the lysates were made 1M Nacl, incubated ON at +4 degrees C. and then spun at 15,000 rpm for 10 minutes in the cold. The supernatants were extracted with phenol once, 12 µg of mussel glycogen was added and the DNA precipitated twice by adding 0.5 volumes of 7.5M NH$_4$OAc and 2.5 volumes of ethanol. The resulting DNA pellet was washed once with 80% ethanol, dried and taken up in 1 µl of distilled H$_2$O. The entire prep was then electroporated into E. coli strain DH-10B and the resulting colonies grown up ON. This represents one panning cycle. The ten library aliquots were panned each one separately for a total of three cycles.

From the last cycle of each pool, DNA was again extracted and this time transfected into COS cellmiclated on plastic one-chamber microscopic slides (2 slides per pool). 2–3 days after transfection, to one of the slides was bound labeled human IL-12 ($10^6$ cpm/ml=300 pM in RPMI 1640 plus 5% FCS for 2–3 hours at 4 degrees C.) and to the other slide labeled monoclonal Ab 2-4E6 ($2 \times 10^6$ cpm/ml =1 nM in RPMI 1640 plus 5% FCS for 1 hour at RT). The slides were washed in PBS, fixed for 40 seconds in a cold mixture of methanol:acetone (7:3) and air dried. The slides were subsequently dipped in Kodak photographic emulsion NTB2, air dried and exposed in a light-tight container for 2–4 days at 4 degrees C. They were developed in Kodak D10 developer according to the manufacturer's instructions and evaluated under a light microscope using a 10 to 40 fold bright field magnification. One of the ten pools, number 5, showed a large number of positive cells both for IL-12 and 2-4E6 binding. E coli clones from this 3× panned pool were subsequently picked into a microtiterplate (3 clones per well for a total of 288 clones). Pools representing the 8 rows and 12 columns from this plate were grown up and their plasmid DNA extracted. These 20 preps were transfected separately into COS cells on 12 well plates ($10^5$ cells well, 4 wells per pool). 2–3 days after the transfection, labeled IL-12 was bound to the cells in two wells (total binding), whereas the other two wells per pool received labeled IL-12 and a 100 fold molar excess of cold IL-12 (=nonspecific binding).

Wells were washed and the bound radioactivity eluted with 0.5 ml of 1% SDS and counted in a gamma counter. Two positive pools were identified in this manner, one representing column 1 and the other one representing row F from the microtiterplate E. coli clones from well F1 must thus contain the IL-12 binding activity. Clones from that well were replated, and DNA from 10 single colonies was analyzed for plasmid insert size. 3 out of the 10 colonies showed an insert of about 2.1 kilobases in length, large enough to encode the IL-12 receptor. One of these- clones was picked for further analysis.

Characterization of IL-12 receptor cDNAs

IL-12 receptor clone No. 5 was picked as described above and the plasmid DNA isolated. Gel isolated insert was sequenced on both strands using the ABI automated DNA sequencer in conjunction with a thermostable DNA polymerase and dye-labeled dideoxynucleotides as terminators.

Sequence alignments were run using the ALIGN program (M. O. Dayhoff et al., Methods Enzymology 91,524,1983) with the mutation data matrix, a break penalty of 6 and 100 random runs.

Cloned IL-12 receptor cDNAs were expressed in COS cells using either the DEAE dextran transfection or electroporation techniques (Molecular Cloning Manual). Binding assays with labeled IL-12 or labeled 2-4E6 antibody were run as described hereinabove under anti human IL-12 receptor antibody. The binding data were analyzed and Kd values were calculated according to Scatchard, using the LIGAND program discussed hereinabove under anti human IL-12 receptor antibody. In vivo labeling (6 hours) of COS cells ($3 \times 10^5$ cells per 35 mm diameter tissue culture dish) with $^{3.5}S$ Cysteine was performed 3 days after transfection as described (Molecular Cloning Manual). Cells were washed in PBS and lysed in CHAPS lysis buffer (10 mM CHAPS-300 mM Nacl-50 mM Tris-HCl pH 7.4-2 mg/ml lodoacetamide-0.17 mg/ml PMSF), precleared by incubation with protein G Sepharose beads (50 µl packed beads per ml, Genex) and normal mouse serum (25% final concentration) at 4° C. overnight. The beads were spun out and labeled IL-12 receptor was specifically immunoprecipitated from the cleared lysates by adding 5 µg of 2-4E6 antibody per ml of sample. The antibody was diluted in PBS containing 1% bovine serum albumin and had been loaded onto 50 µl of packed beads for 2–3 hours at 4° C . Immunoprecipitation took place overnight at 4° C. The next day, the beads were washed 3–4 times in CHAPS lysis buffer before analysis on SDS-polyacrylamide gels as described (Molecular Cloning Manual).

Lymphocyte proliferation assay

Lymphocyte proliferation assays to assess the ability of rat antisera to block cytokine-induced proliferation were performed as previously described (M. K. Gately, et al., 1992, Current Protocols in Immunology, vol. 1., J. E. Coligan, et al., eds., John Wiley & Sons, New York, N.Y., p. 6.16.1) with the following modifications. Aliquots of human PHA-activated PBMC ($2 \times 10^4$ per well) and of diluted rat sera were mixed in the wells of a 96-well plate and incubated at 37° C. for 30 min. The cytokines (IL-12, IL-2 or IL-7) were then added to the wells, and the cultures were incubated for 48 h at 37° C. Following this, $^3$H-TdR was added to each well, and the cultures were harvested after an additional 7 h at 37° C. All values are the means of triplicates.

Flow cytometry

The titers of anti-COS cell antibodies in the various rat antisera were assessed by flow cytometry as follows. Untransfected COS cells ($10^6$ cells/0.1 ml of Dulbecco's PBS containing 2% heat-inactivated FCS and 01% sodium azide) were preincubated with 400 µg/ml normal rat IgG (Sigma, St. Louis, Mo.) for 15 min. on ice, and then with the indicated amount of rat serum for 30 min. on ice. The cells were washed and further incubated with 2 µg/ml FITC-conjugated F(ab')$_2$ mouse anti-rat IgG (Jackson ImmunoResearch Laboratories, Inc., West Grove, Pa.) for 30 min. on ice. The cells were again washed and then analyzed by flow cytometry using a FACScan (Becton-Dickinson, Mountain View, Calif.).

Inhibition of IL-12-induced lymphoblast proliferation by anti-IL-12R anti serum

Figure 18A:
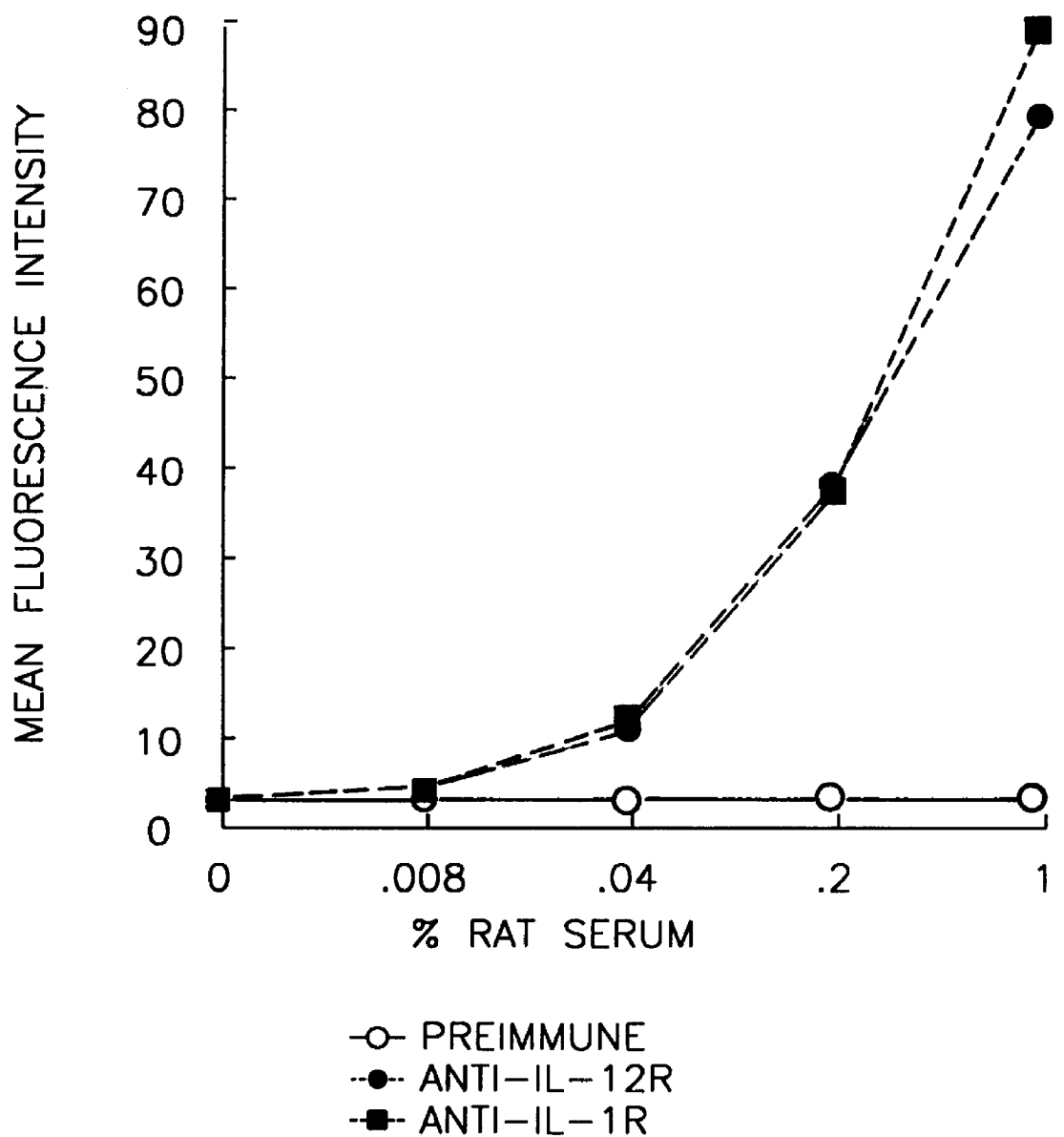
FIGS. 18A, 18B, 18C, and 18D: Specific inhibition of IL-12-induced lymphoblast proliferation by a rat anti-IL-12R antiserum. (18A) Titration by flow cytometry of anti-COS cell antibodies in an anti-IL-12R antiserum (--●--) made against 2-4E6-transfected COS cells, preimmune serum (--○--) from the rat used to prepare the anti-IL-12R antiserum, and a rat antiserum made against COS cells transfected with the human type II IL-1R (--■--). (18B-18D) Effects of rat sera on proliferation of PHA-activated PBMC induced by IL-12 (18B), IL-2 (18C), or IL-7 (18D). All standard errors were <10% of the means.
Figure 18B:
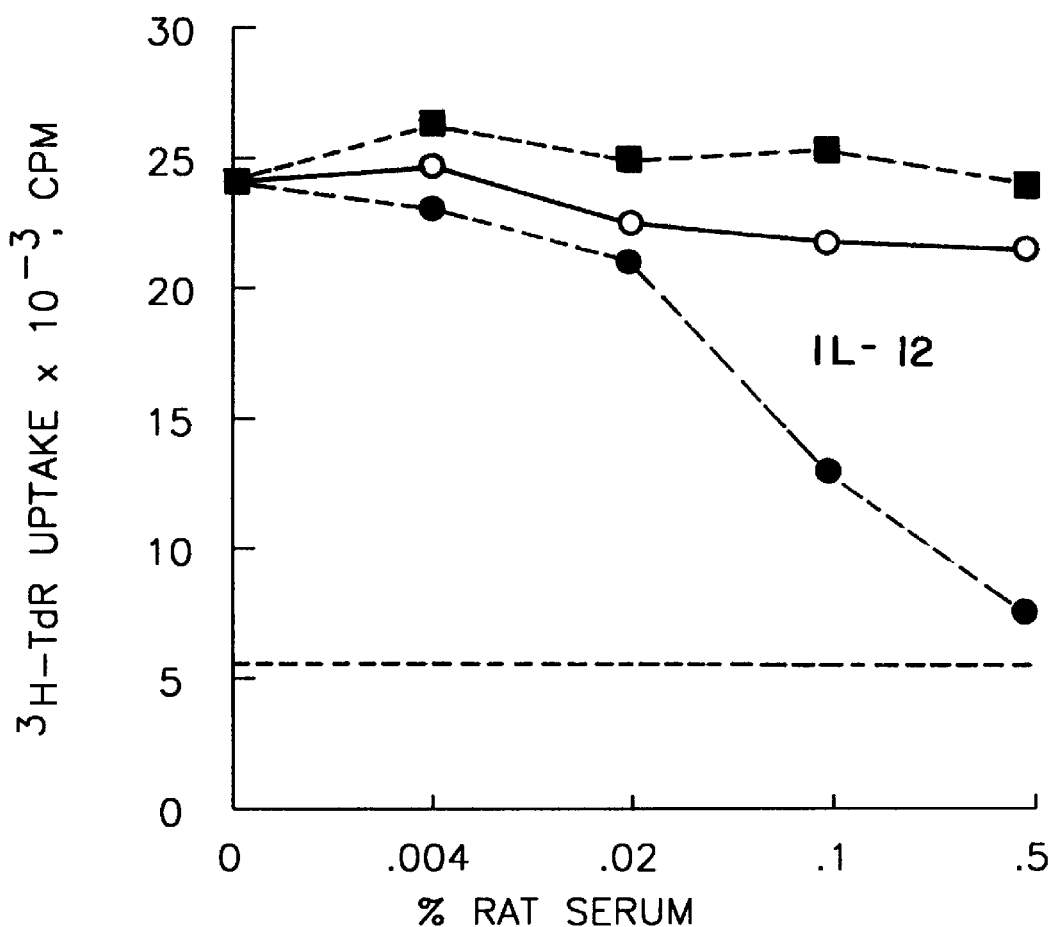
Figure 18C:
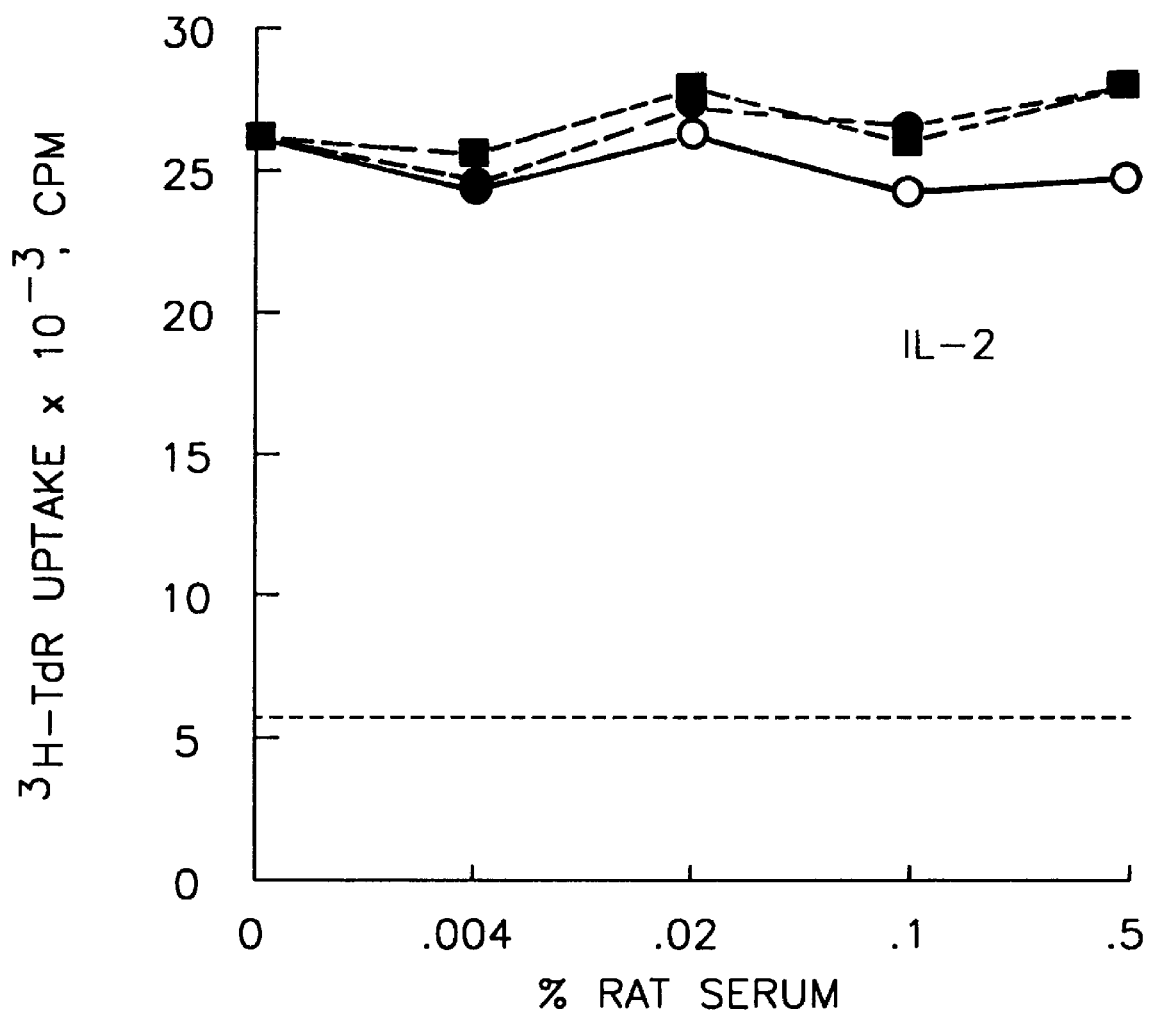
Figure 18D:
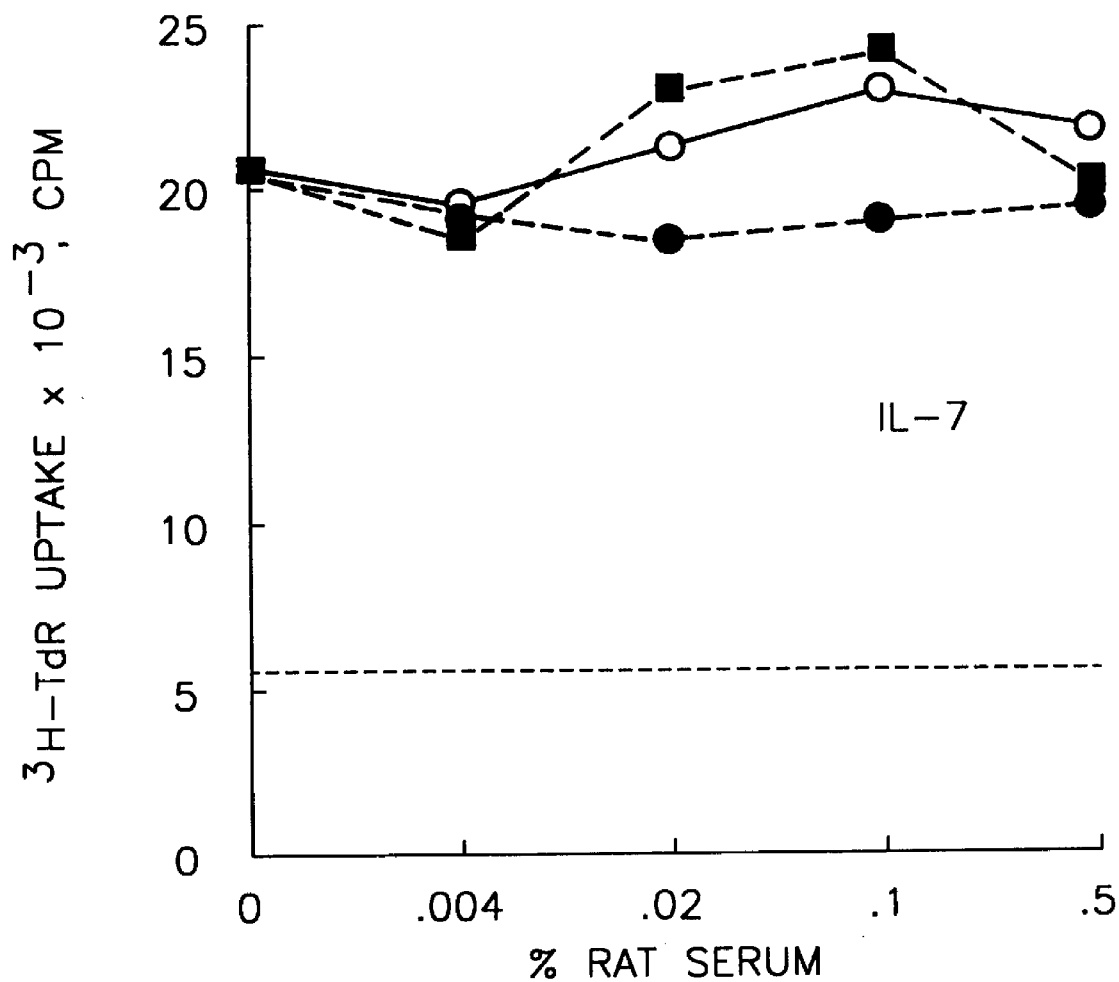

To determine whether the cloned IL-12R subunit plays an essential role in an IL-12-induced biologic response, we examined whether antiserum to the. cloned IL-12R subunit could inhibit IL-12induced proliferation of PHA-activated PBMC. This antiserum was produced by immunizing rats with 2-4E6-transfected COS cells and thus contained anti-COS cell antibodies as well as antibodies to the (putative) IL-12R subunit. For use as a control, we screened several other available rat antisera which had been prepared previously by immunization of rats with COS cells expressing proteins unrelated to the IL-12R. One such antiserum had been raised against COS cells transfected with human type II IL-1R and displayed a titer of anti-COS cell antibodies virtually identical to that of the anti-IL-12R antiserum (FIG. 18A). We then compared the effects of the anti-IL-12R antiserum, the anti-IL-1R antiserum, and preimmune serum (from the rat used to prepare the anti-IL-12R) on lymphoblast proliferation induced by IL-12, IL-2, or IL-7. The concentrations of IL-12, IL-2, and IL-7 were 0.25 ng/ml, 1.25 ng/ml, and 0.4 ng/ml, respectively. These concentrations were chosen because they resulted in similar levels of $^3$H-TdR incorporation and were on the steep portion of the dose-response curves. In this experiment, the maximum levels of $^3$H-TdR incorporation in the presence of saturating amounts of cytokine were 38,820, 111,303, and 89,541 cpm for IL-12, IL-2, and IL-7, respectively. The level of $^3$H-TdR incorporation in the absence of any added cytokine is indicated by the horizontal dotted line. Two experiments were performed with essentially identical results, and one of these is illustrated in FIGS. 18B–D. The anti-IL-12R antiserum caused dose-dependent inhibition of IL-12-induced lymphoblast proliferation but had no effect on proliferation induced by IL-2 or IL-7. In contrast, neither the preimmune serum nor the anti-IL-1R antiserum inhibited lymphoblast proliferation induced by any of the three cytokines tested. These results strongly suggest that the cloned IL-12R subunit plays an essential role in mediating IL-2-induced proliferation of PHA-activated PBMC.

Sequence Analysis of IL-12 receptor cDNA clones

The DNA sequence for the IL-12 receptor cDNA insert from clone No. 5 is shown in FIGS. 1A, 1B and 1C (SEQ ID NO:1). The deduced amino acid sequence for the encoded receptor-protein is shown in FIG. 2. The IL-12 receptor protein is thus composed of 662 amino acids and a calculated molecular weight of 73,112. The IL-12 receptor protein has the following features: N-terminal signal peptide, extracellular domain, transmembrane domain and cytoplasmic tail. The classical hydrophobic N-terminal signal peptide is predicted to be 20–24 amino acids in length. Signal peptide cleavage has been shown to occur mostly after the amino acids Ala, Ser, Gly, Cys, Thr, Gin (G. von Heijne, Nucl. Acids Research, 1986, 14:4683). For the IL-12 receptor, the cleavage could thus take place after Gln20, Ala23 or Cys24 in the sequence shown in FIG. 2, leaving a mature protein of 638 amino acids (calculated molecular weight=70,426) based on cleavage at Cys24. The extracellular domain of the receptor is predicted to encompass the region from the C-terminus of the signal peptide to amino acid No. 540 in the sequence shown in FIG. 2. Hydrophobicity analysis shows the area from amino acid No. 541 to 571 to be hydrophobic, as would be expected for a transmembrane anchor region. Charged transfer stop residues can be found at the N- as well as the C-terminus of this predicted transmembrane area. The extracellular domain of the receptor is thus 516 amino acids long and contains all the 6 predicted N-linked glycosylation sites. The cytoplasmic portion is 91 amino acids long (amino acid residue nos. 572 to 662) and contains 3 potential phosphorylation sites (S/TXXD/E) for casein kinase II.

The cDNA library was rescreened using the insert from clone No. 5 as the probe, and a second independent cDNA was isolated (clone No. 17). This cDNA contained an additional 202 bp of 3' untranslated region. The amino acid sequence (SEQ ID NO:3) deduced from this clone for the IL-12 receptor protein was almost completely identical to the sequence shown in FIG. 2 (SEQ ID NO:2); however, a 13 bp deletion in the cDNA right before the stop codon changes the reading frame at the very C-terminus of the receptor and also gives rise to a protein that is 2 amino acids shorter (SEQ ID NO:3). Cycle sampling PCR was performed on uncloned cDNA using a pair of primers spanning the region that is expected to differ between the mRNAs representing clones 5 and 17. This analysis demonstrated that both transcripts coding for these two membrane-bound variants of the receptor subunit are present in the mRNA population isolated from PHA-activated PBMC at about equal levels (data not shown). The two transcripts are likely to arise from an alternate splicing event.

Further analysis of the amino acid sequence of the IL-12 receptor shows it to be a member of the cytokine receptor superfamily, by virtue of the sequence motifs [Cys52 - - - Cys62SW] and [W222SKWS]. Comparing the IL-12 receptor sequence to all the members of the superfamily by running the ALIGN program shows that the IL-12 receptor has the highest homology to human gp130.

Sequence analysis of the IL-12 receptor extracellular domain demonstrated the presence of the hemopoietin receptor hallmark features: two pairs of conserved cysteine-residues and the WSXWS motif Further comparisons to the hemopoietin receptor superfamily showed the newly isolated. IL-12 receptor component (SEQ: ID NO:5) to be highly related to a subgroup of family members composed of gp130 (SEQ: ID NO:5), G-CSF-receptor (SEQ: ID NO:6) and LIF-receptor (SEQ: ID NO:7) (FIGS. 3A and 3B); align scores were 12.37 (IL-12R/gp130), 7.35 (IL-12R/G-CSF-R) and 6.31 (IL-12R/LIF-Rbeta). Similarities between the IL-12 receptor component and these three proteins extend beyond the hemopoietin receptor domain and include the area from the WSXWS motif to the transmembrane region (FIG. 3). The extracellular portion of gp103 (M. Hibi et al., 1990, Cell, 63: 1149) was shown i) to contain the hemopoietin receptor superfamily domain and ii) to be also composed of 6 type III fibronectin repeats about 90 amino acids long (A. R. Kornblihtt, et al., 1985, EMBO J., 4:1755; L. Patthy, 1990, Cell, 61:13). Similarly, the extracellular domain of the IL-12 receptor can be subdivided into five such fibronectin type III repeats (residues 43–133, 143–236, 237–337, 338–444 and 445–540). The IL-12 receptor extracellular domain lacks the N-terminal Ig domain found in gp130 and therefore only accommodates 5 fibronectin type III repeats. Further sequence similarities between the IL-12 receptor, gpl130 (SEQ: ID NO:5), the G-CSF-receptor (SEQ: ID NO:6) and the LIF-receptor (SEQ: ID NO:7) can be found in the cytoplasmic regions (FIGS. 3A and 3B). A PXXPXP motif within a box of 8 amino acids conserved between a number of different superfamily members and a second, 12 amino acid long conserved box were found to be important for signal transduction mediated by gp130 (M. Murakami, et al., 1991, Proc. Nati. Acad. Sci. (U.S.A.), 88:11349). Both those motifs are also found in conserved areas of the cytoplasmic part of the IL-12 receptor sequence (amino acid residues 577–584 and amino acid residues 618–629).

Analysis of IL-12 Receptor mRNA Expression

Figure 6:
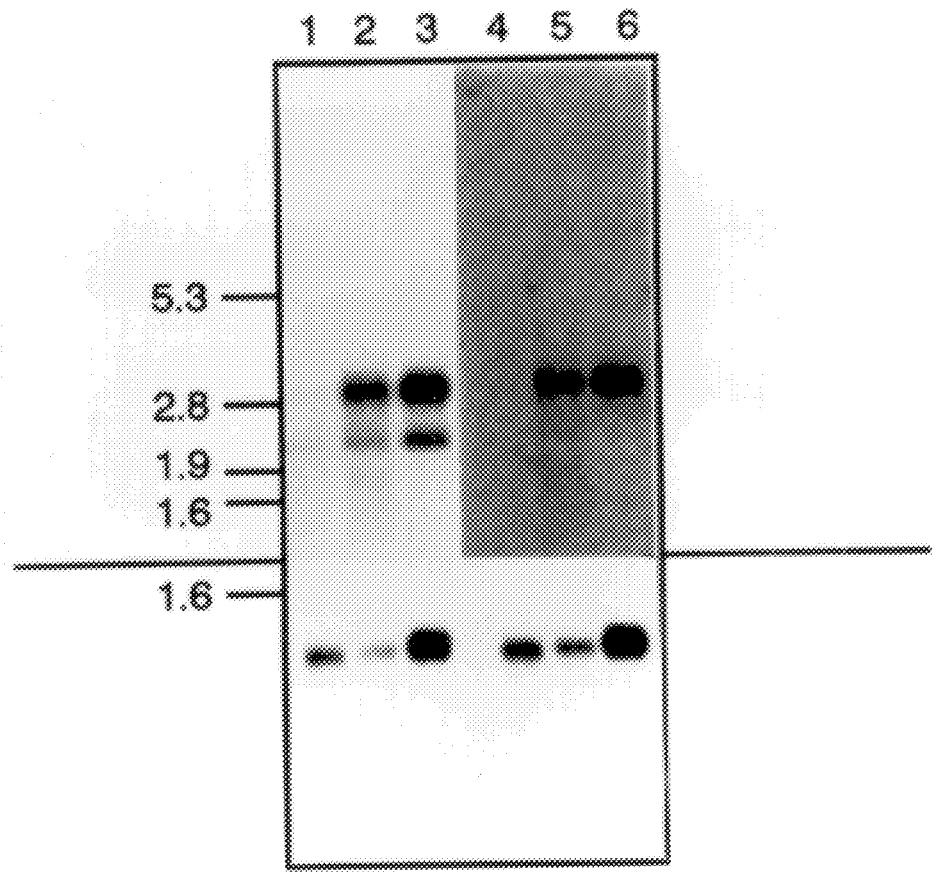
FIG. 6: RNA blot analysis. 2 µg of polyA+ RNA were run per lane. Upper panel: Lanes 1–3 were probed with a full-length receptor cDNA; lanes 4–6 were probed with the cytoplasmic portion only. Unstimulated PBMC: lanes 1,4. PHA-activated PBMC: lanes 2,5.

RNA blots were performed using poly A+ RNA from cells known to respond to IL-12: PHA-stimulated PBMC and the CD4+ T-cell line Kit225. Two RNA transcripts about 3 Kb and 2.3 Kb in size are apparent when blots are probed with the full-length cDNA (FIG. 6, lanes 1–3). Both RNAs are induced from undetectable or very low levels when PBMC are activated by PHA for 3 days (compare lanes 1 and 2); Kit225 cells express both transcripts constitutively (lane 3). Analysis by phosphoimager shows the level of the larger RNA to be about 3 to 5 fold higher than the level of the smaller RNA. Surprisingly, the smaller RNA does not hybridize to a probe derived from the cytoplasmic domain (lanes 4–6). This finding could indicate the presence of an RNA encoding i) a soluble IL-12 receptor protein, ii) a membrane bound IL-12 receptor devoid of a cytoplasmic region altogether or iii) an IL-12 receptor with a cytoplasmic sequence that is completely different from the ones present in clones 5 and 17. Elucidation of this question will have to await the isolation of a cDNA clone derived from the smaller RNA transcript.

Characterization of Recombinant IL-12 Receptor

Figure 19A:
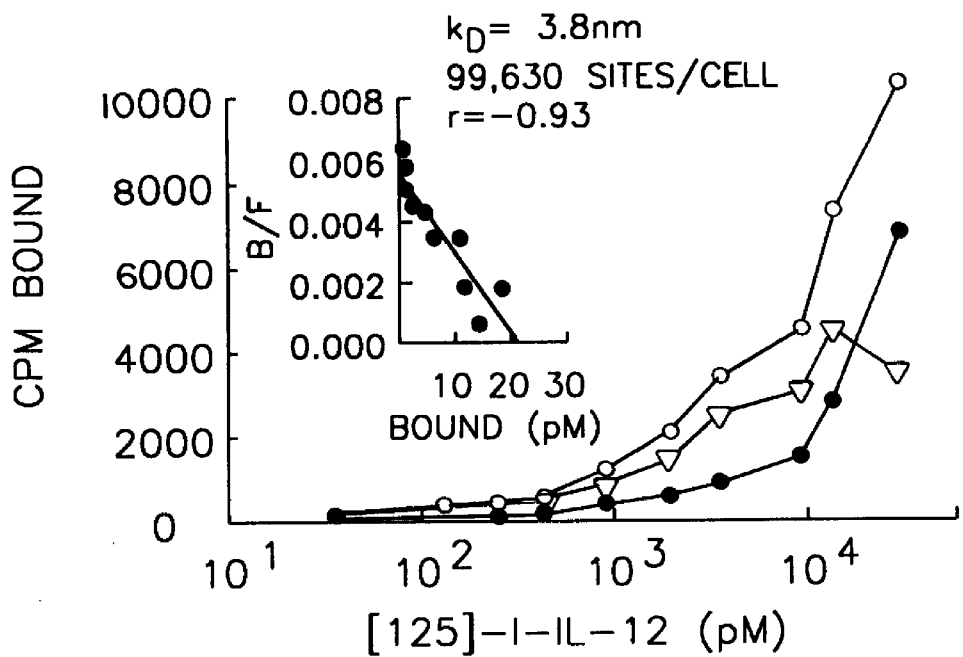
FIGS. 19A and 19B: Equilibrium binding of $^{125}$I-IL-12 to COS cells expressing the IL-12 receptor subunit. 19A) human IL-12 and 19B) murine IL-12. The insets show analysis of the binding data according to the method of Scatchard.
Figure 19B:
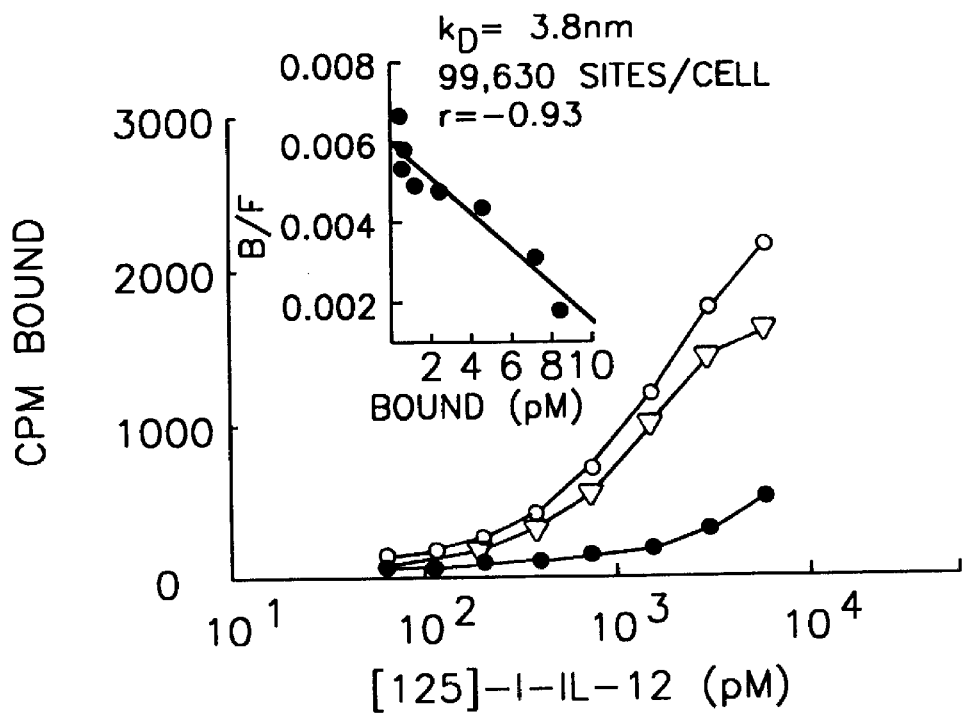

IL-12 receptor cDNA (clone number 5) (SEQ ID NO:1) was electroporated into COS cells and equilibrium binding of labeled human and murine IL-12 to the cells was performed and analyzed as described (R. Chizzonite, et al., 1992, J. Immunol., 148:3117). Results are shown in FIGS. 19A and 19B. humane and murine IL-12 bind to recombinant IL-12 receptor (SEQ ID NO:2) with a single affinity ($K_D$) of 3.4±1.3 nM (n=7) and 2.1±0.5 nM (n=4), respectively, which corresponds to the low affinity component of the functional IL-12 receptor on PHA-activated PBMC. After transformation by the method of Scatchard, the equilibrium binding data was best described by a single receptor site model as determined by the LIGAND program. The site numbers indicated in FIG. 19 are calculated assuming that all cells are expressing receptors. IL-12 receptor protein expressed by clone number 17 (SEQ ID NO:3) gave similar results in these binding assays. SEQ ID NO:3 would also have the same regions as SEQ ID NO:2.

Figure 5:
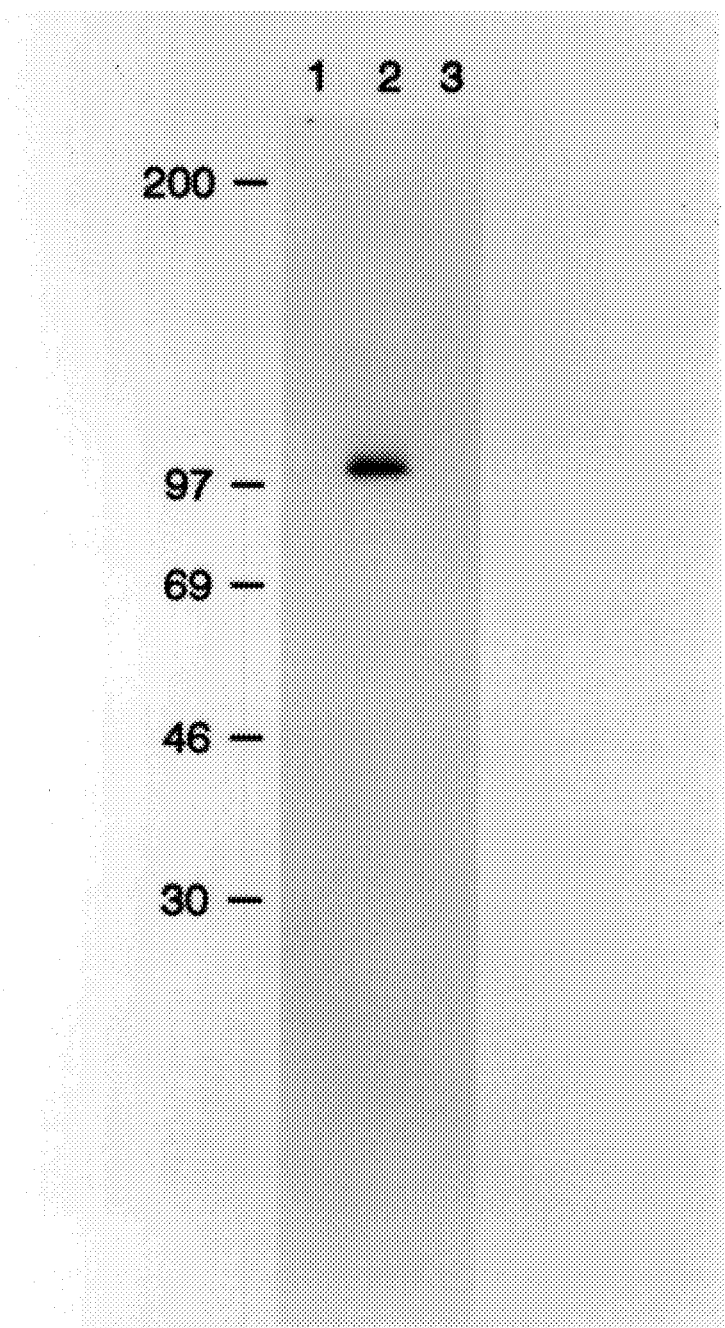
FIG. 5: Analysis of the size of human recombinant IL-12 receptor expressed in COS cells. COS cells transfected with human IL-12 receptor cDNA were labeled and lysed as described herein. Human IL-12 receptor protein was immunoprecipitated and the products were analyzed on a 4–20% gradient gel under reducing conditions. 5 µg of each listed antibody were used. They were Control $I_gG3$=isotype-matched negative control antibody; 2-4E6=anti-human IL-12 receptor antibody: 4D6 =anti human IL-12 negative control antibody. Sizes of marker proteins are indicated in KDa on left.
Figure 17:
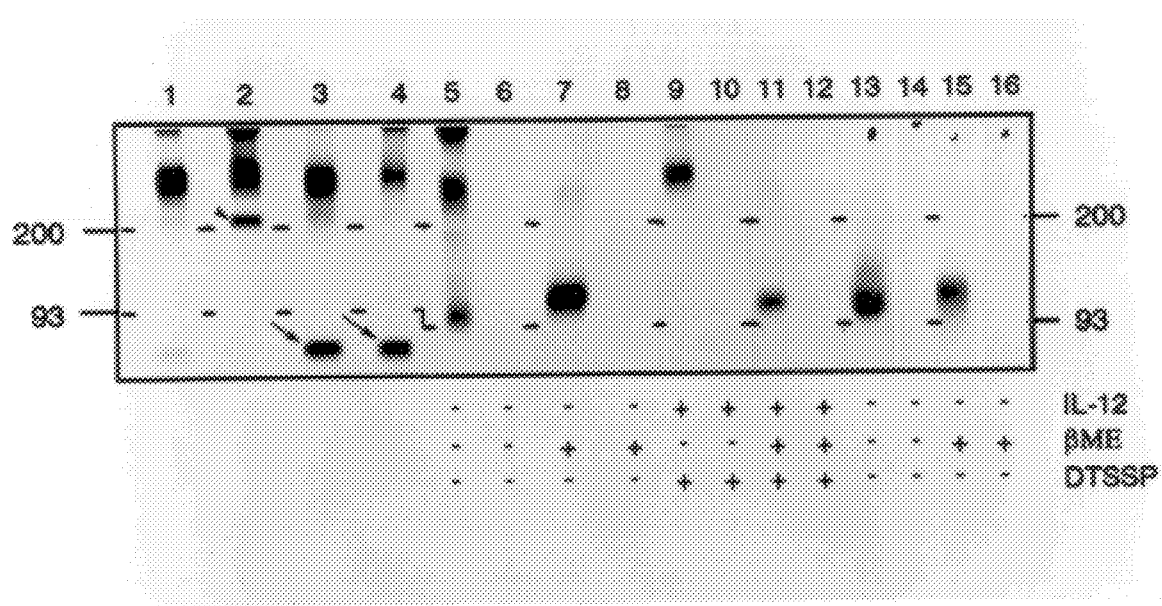
FIG. 17: Size of the IL-12 receptor subunit on the surface of transfected COS and CTLL cells. 8% gels were used and marker sizes in KDa are indicated. Lanes 1–4: Analysis of affinity crosslinked complexes under non-reducing conditions. Arrowhead=labeled, uncrosslinked 2-4E6 antibody. Arrows=labeled, uncrosslinked IL-12. Lanes 5–12: Analysis of $^{125}$I-COS Cell Surface Proteins. Sample reduction, binding of 25 nM unlabeled IL-12 to the cells prior to analysis and use of 1 mM DTSSP crosslinker are indicated below the lanes. Lanes 13–16: Analysis of $^{125}$I-CTLL cell surface proteins.

Metabolic labeling and immunoprecipitation of the IL-12 receptor subunit expressed in COS cells indicated its size to be about 100 KDa as determined by gel analysis under reducing conditions (FIG. 5). To analyze the size of the receptor at the cell surface, affinity crosslinking studies were performed. Unless otherwise stated, characterization of the IL-12 receptor protein was done on SEQ ID NO:2. Crosslinking of 0.2 nM $^{125}$I-labeled IL-12 to either transfected COS cells, PHA-activated PBMC or K6 cells gave rise to complexes that migrate at >200 KDa (FIG. 17, lanes 1,3 and 4; arrow indicates uncrosslinked IL-12). Crosslinking at 2 nM $^{125}$I-IL-12 (a concentration equivalent to the $K_D$) gave identical results (not shown). The size of a complex composed of one receptor subunit and one IL-12 ligand is expected to be about 175 KDa. However, FIG. 17 shows that the 175 KDa complex is present only at very low levels, if at all. Since the 150 kDA Ig and the 200 KDa markers are not separated on the gel system used, the 175 KDa IL-12/IL-12 receptor complex is expected to comigrate with them. For comparison, lane 2 shows transfected COS cells crosslinked to labeled 2-4E6 antibody (arrowhead=uncrosslinked 2-4E6). Crosslinking labeled IL-12 to i) cells that do not bind IL-12 (e.g. Raji cells), ii) mock-transfected COS cells or iii) transfected COS cells in the presence of an excess of cold IL-12 did not yield any products (not shown). For FIG. 17, labeled IL-12 (0.2 nM) was bound and crosslinked with BS3 (0.4 mM) to transfected COS cells (lane 1), PHA-activated PBMC (lane 3) or K6 cells (lane 4). Labeled 2-4E6 antibody (0.5 nM) was bound and crosslinked with BS3 (0.4 mM) to transfected COS cells (lane 2). Anti-IL-12 receptor antibody 2-4E6 (lanes 5,7), anti IL12 antibody 4D6 (lanes 9,11) and control antibody (lanes 6,8,10,12,) were used. Antibody 2-4E6 (lanes 13,15) and control antibody (lanes 14,16,) were used.

Since crosslinking of labeled IL-12 to IL-12 receptor gave rise to products that are larger than what is expected for a complex of one receptor and one IL-12 ligand but whose size is difficult to estimate, cell surface labeling and immunoprecipitation experiments of transfected COS cells were performed. Samples were analyzed under reducing and nonreducing conditions (FIG. 17, lanes 5–12). The results can be summarized as follows: i) transfected COS cells express the IL-12 receptor subunit both as monomers and as a second, larger product that could be dimers or oligomers. Both these products are present at about depend on IL-12 binding. If IL-12 is prebound to the cells, the resulting banding pattern does not change (not shown); and iii) The dimers/oligomers can be converted to the monomers by reduction and must therefore be disulfide-bonded (lane 7). The data from the crosslinking and surface labeling experiments thus suggested that only the dimeric/oligomeric receptor subunit form binds IL-12 with the 3 nM affinity measured on transfected COS cells. This possibility was further investigated as follows. Complexes produced by binding unlabeled IL-12 to $^{125}$I-surface labeled COS cells and crosslinking with a cleavable crosslinker were immunoprecipitated by an anti-IL-12 antibody and analyzed under non-reducing and reducing conditions (FIG. 17, lanes 9–12). The anti-IL-12 antibody only precipitated a complex corresponding to IL-12 bound to the dimer/oligomer but not the monomer of the IL-12 receptor subunit (lane 9). Analysis of this complex under reducing conditions identified a labeled protein that co-migrated with the IL-12 receptor monomer (lane 11). Experiments with a murine CTLL cell transfectant stably expressing the IL-12 receptor subunit lend further support to our findings. These cells express about 3000 to 5000 receptor subunits per cell, as measured by 2-4E6 antibody binding; however, the cells bind IL-12 very inefficiently, with an estimated Kd of 50 nM or greater (not shown). The results from surface labeling and immunoprecipitation experiments with the CTLL transfectants clearly indicate that they only express IL-12 receptor subunit monomers (FIG. 17, lanes 13–16). Taken together, the data support the hypothesis that only the receptor subunit dimers/oligomers bind IL-12 with the low affinity (3 nM) measured on transfected COS cells.

Discussion

We report here the isolation of a cDNA (clone no. 5; SEQ ID NO:1) coding for a type I transmembrane protein that represents a low affinity component of the functional IL-12 receptor (SEQ ID NO:2) found on PHA-activated PBMC. Several lines of evidence are available to support this claim. i) When transfected into COS cells, the cDNA confers specific IL-12 binding to the cells. ii) The affinity of this receptor-ligand interaction is about 3 nM, which corresponds to the low affinity IL-12 receptor component observed on PHA blasts. iii) The recombinant IL-12 receptor component expressed in COS cells binds both human and murine IL-12 ligands with comparable affinity. This is expected, since it was shown that similar concentrations of human and murine IL-12 transduce a signal through the human IL-12 receptor (D. S. Schoenhaut, et al., 1992, J. Immunol., 148:3433). iv) The 2-4E6 antibody recognizes both the recombinant receptor component expressed in COS cells and a component of the IL-12 receptor expressed on PHA-activated PBMC and K6 cells. 2-4E6 immunoprecipitates the complex of $^{125}$I-IL-12 affinity crosslinked to the functional IL-12 receptor on activated PBMC and K6 cells. v) Polyclonal antiserum from a rat immunized with whole COS cells transfected with the IL-12 receptor subunit inhibits proliferation of PHA-activated PBMC induced by IL-12, but not IL-2 or IL-7 induced proliferation. Whether it also plays an essential role in other IL-12-induced responses, such as IFN-gamma production by resting PBMC or NK cell activation, remains to be determined. Dual label flow cytometry has shown that the IL-12 receptor subunit is upregulated on NK-cells cultured with IL-2, consistent with our previous observations that IL-2 caused upregulation of IL-12 receptors on NK-cells (B. B. Desai, et al., 1992, J. Immunol., 148:3125). No neutralizing monoclonal antibodies to the IL-12 receptor subunit are currently available.

The size of the IL-12 receptor subunit at the cell surface was estimated by affinity crosslinking of labeled IL-12 as well as cell-surface labeling studies. Transfected COS cells express the IL-12 receptor subunit as a protein of about 100 KDa size. The calculated molecular weight for the mature form of the protein is 70,426; thus, about 25% of the molecular weight of the surface expressed protein is likely to be carbohydrate. Transfected COS cells also express a larger molecular weight form of the IL-12 receptor subunit. Our present working hypothesis, but to which we do not wish to be bound, is that this form is a disulfide-bonded dimer or oligomer of the receptor subunit. In our hands, none of the available gel systems allows the reliable separation of proteins with sizes over 150 KDa. Thus, the exact size of the receptor complexes formed is not known at this time.

The available evidence supports the conclusion that the IL-12 receptor dimerization/oligomerization is independent of IL-12 binding. Similar to these findings, it has been reported for the EPO receptor that disulfide-bonded receptor dimers and oligomers are formed and that EPO stimulation had no detectable effect on receptor dimerization (O. Miura, et al., 1993, Archives Biochem. Biophys., 306:200). Our data also indicate that only the IL-12 receptor dimers/oligomers bind IL-12 with the 2–5 nM affinity observed on intact transfected COS cells. i) An anti-IL-12 antibody only immunoprecipitates an affinity crosslinked complex corresponding to one IL-12 and a receptor dimer/oligomer. ii) Affinity crosslinked complexes of the size expected for one receptor subunit and one IL-12 are formed very inefficiently at IL-12 concentrations corresponding to the KD measured on transfected COS cells. iii) Murine CTLL cells stably expressing the receptor subunit bind IL-12 very inefficiently (estimated KD=50 nM or lower); these cells also do not express subunit dimers/oligomers. It was unexpected to find that COS cells and CTLL cells differ in their ability to express the IL-12 receptor subunit in a way that allows IL-12 binding. This could be due to species specificity: murine CTLL cells are somehow unable to "process" the human IL-12 receptor protein correctly, resulting in inefficient dimerization/oligomerization and IL-12 binding. Conceivably, COS cells could express an endogenous protein that allows the IL-12 receptor dimerization/oligomerization to occur. Since under the experimental conditions used, the number of low-affinity IL-12 receptor sites per transfected COS cell is always greater than $10^5$, it seems unlikely that an endogenous COS cell component forms dimers or oligomers with the receptor subunit, although this possibility cannot be completely ruled out. Further studies will be required to evaluate these possibilities.

The IL-12 receptor subunit that we have isolated is a member of the hemopoietin receptor superfamily. Within that family, it is most closely related over its entire length to gp130 and the receptors for G-CSF and LIF. The extracellular portion of the IL-12 receptor subunit can also be divided into five fibronectin type III repeats, similar to what was reported for gp130 (M. Hibi, et al., 1990, Cell, 63:1149). It is interesting to note that the ligands for IL-12 receptor and gp130, i.e. IL-12 p40 and IL-6 receptor, both also contain such fibronectin type III repeats (M. Hibi, et al., 1990, Cell, 63:1149; D. S. Schoenhaut, et al., 1992, J. Immunol., 148:3433). Some features of the cytoplasmic portion of the IL-12 receptor subunit merit further comment. Compared to the corresponding areas in gp130 (276 AA) and the receptor for LIF (237 AA), it is rather short. However, mutagenesis studies have shown that for gp130, only about 100 amino acids in the cytoplasmic region are sufficient to transduce a signal (M. Murakami, et al., 1991, Proc. Natl. Acad. Sci. (U.S.A.), 88:11349). The potential functionality of the IL-12 receptor cytoplasmic portion appears to be borne out further by the presence of a number of features conserved in other functional hemopoietic receptors (among them the receptors for G-CSF, EPO and GM-CSF): conserved areas 1 and 2 (M. Murakami, et al., 1991, Proc. Natl. Acad. Sci. (U.S.A.), 88:11349) are clearly present and thus give the low affinity IL-12 receptor component the makeup of a beta type subunit (N. Stahl, et al., 1993, Cell, 74:587).

Some reports in the past have drawn analogies between the IL-6 and IL-12 systems. Because homologies exist between i) the IL-12 p35 subunit and IL-6 (D. M. Merberg, et al., 1991, Immunology Today, 13:78) and ii) the IL-12 p40 subunit and the extracellular domain of the IL-6 receptor, IL-12 has been viewed as a complex between a soluble receptor (p40) and a cytokine (p35) (D. P. Gearing, et al., 1991, Cell, 66:9). It was predicted that the IL-12 receptor would be homologous to gp130 (D. Cosman, 1993, Cytokine, 5:95). Our results clearly support this prediction; however, they also demonstrate differences between the IL-6/soluble IL-6 receptor/gp130 system and the IL-12/IL-12 receptor system. Expression of gp130 occurs in a wide variety of cells and in an almost constitutive fashion (T. Taga, et al., 1992, FASEB J., 6:3387); the IL-12 receptor subunit and its mRNA are highly inducible in PBMC. Gp130 acts as an affinity converter for the IL-6/IL-6 receptor interaction (T. Taga, et al., 1992, FASEB J., 6:3387); the IL-12 receptor subunit simply binds IL-12 heterodimer composed of covalently bound p35 and p40 chains with low affinity. Upon binding of IL-6/soluble IL-6R, gp130 dimerizes and a signal is transduced (M. Murakami, et al., 1993, Science, 260:1808); IL-1 2 receptor dimerization/oligomerization appears to be ligand independent, and a further receptor subunit is likely to be required to yield a high-affinity, functional IL-12 receptor. In that context, it is interesting to note that a previous analysis of the IL-12 receptor on PHA blasts identified an IL-12 binding protein of about 110 KDa and a receptor associated protein of about 85 KDa (R. Chizzonite, et al., 1992, J. Immunol.,148:3117). It is possible that the 110 KDa protein represents the subunit whose structure is reported here. It will be interesting to characterize the additional IL-12 receptor component and evaluate its effects on IL-12 binding and signal transduction.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. A substantially pure, homogeneous and isolated low affinity human Interleukin-12 receptor protein comprising an amino acid sequence selected from SEQ ID NO:2 or SEQ ID NO:3 and which binds specifically to Interleukin-12.

2. The Interleukin-12 receptor protein of claim 1 having the amino acid sequence SEQ ID NO:2.

3. The low affinity Interleukin-12 receptor protein of claim 1 wherein the Interleukin-12 receptor protein has a $K_D$ of about 2 to about 10 nM.

4. The low affinity Interleukin-12 receptor protein of claim 3 wherein the Interleukin-12 receptor protein has a $K_D$ of about 2 to about 5 nM.

5. The low affinity Interleukin-12 receptor protein of claim 4 wherein the Interleukin-12 receptor protein has the amino acid sequence SEQ ID NO:2.

6. The low affinity Interleukin-12 receptor protein of claim 4 wherein the Interleukin-12 receptor protein has the amino acid sequence SEQ ID NO:3.

7. The Interleukin-12 receptor protein of claim 1 having the amino acid sequence SEQ ID NO:3.

8. A pharmaceutical composition comprising a substantially pure, homogeneous and isolated low affinity human Interleukin-12 receptor protein comprising an amino acid sequence selected from SEQ ID NO:2 or SEQ ID NO:3 and which binds specifically to Interleukin-12 and a suitable diluent or carrier.

9. The pharmaceutical composition of claim 8 wherein the human low affinity Interleukin-12 receptor protein has the amino acid sequence SEQ ID NO:2.

10. The pharmaceutical composition of claim 8 wherein the human low affinity Interleukin-12 receptor protein has the amino acid sequence SEQ ID NO:3.

* * * * *